United States Patent
Watanabe et al.

(10) Patent No.: US 9,840,706 B2
(45) Date of Patent: Dec. 12, 2017

(54) ANTISENSE NUCLEIC ACIDS

(71) Applicants: NIPPON SHINYAKU CO., LTD., Kyoto-shi, Kyoto (JP); NATIONAL CENTER OF NEUROLOGY AND PSYCHIATRY, Tokyo (JP)

(72) Inventors: Naoki Watanabe, Ibaraki (JP); Yuuichirou Tone, Ibaraki (JP); Shin'ichi Takeda, Tokyo (JP); Tetsuya Nagata, Tokyo (JP)

(73) Assignees: NIPPON SHINYAKU CO., LTD., Kyoto-shi, Kyoto (JP); NATIONAL CENTER OF NEUROLOGY AND PSYCHIATRY, Kodaira-shi, Tokyo (JP)

( * ) Notice: Subject to any disclaimer, the term of this patent is extended or adjusted under 35 U.S.C. 154(b) by 0 days.

(21) Appl. No.: 15/314,535

(22) PCT Filed: Jun. 16, 2015

(86) PCT No.: PCT/JP2015/067238
§ 371 (c)(1),
(2) Date: Nov. 29, 2016

(87) PCT Pub. No.: WO2015/194520
PCT Pub. Date: Dec. 23, 2015

(65) Prior Publication Data
US 2017/0204410 A1    Jul. 20, 2017

(30) Foreign Application Priority Data

Jun. 17, 2014  (JP) .................................. 2014-124157

(51) Int. Cl.
*A61K 48/00* (2006.01)
*C07H 21/02* (2006.01)
(Continued)

(52) U.S. Cl.
CPC .......... *C12N 15/113* (2013.01); *C12Q 1/6876* (2013.01); *C12N 2310/11* (2013.01);
(Continued)

(58) Field of Classification Search
USPC .................................. 536/23.1, 24.5; 514/44
See application file for complete search history.

(56) References Cited

U.S. PATENT DOCUMENTS

| 2006/0099616 A1 | 5/2006 | van Ommen et al. |
| 2007/0082861 A1 | 4/2007 | Matsuo et al. |

(Continued)

FOREIGN PATENT DOCUMENTS

| JP | 2008-220311 A | 9/2008 |
| WO | WO-2004/048570 A1 | 6/2004 |

(Continued)

OTHER PUBLICATIONS

Tetsuya Nagata, et al., "Gene Therapy of Muscular Dystrophy," Curr. Insights Nuerol. Sci., 2013, vol. 19/20, pp. 20-21, including English translation.

(Continued)

*Primary Examiner* — Terra C Gibbs
(74) *Attorney, Agent, or Firm* — Drinker Biddle & Reath LLP

(57) ABSTRACT

Provided is a drug that allows highly-efficient skipping of exon. The present invention provides an antisense oligomer wherein two or more unit oligomers targeting sequences that are neither consecutive nor overlap with each other in the same exon are connected.

12 Claims, 25 Drawing Sheets

(51) Int. Cl.
*C07H 21/04* (2006.01)
*C12N 15/11* (2006.01)
*C12N 15/113* (2010.01)
*C12Q 1/68* (2006.01)

(52) U.S. Cl.
CPC .. *C12N 2310/3233* (2013.01); *C12N 2320/10* (2013.01); *C12N 2320/33* (2013.01); *C12N 2330/30* (2013.01); *C12Q 2600/136* (2013.01); *C12Q 2600/178* (2013.01)

(56) References Cited

U.S. PATENT DOCUMENTS

| | | |
|---|---|---|
| 2010/0168212 A1 | 7/2010 | Popplewell et al. |
| 2012/0046342 A1 | 2/2012 | Van Deutekom et al. |
| 2012/0202752 A1 | 8/2012 | Lu |
| 2012/0270925 A1 | 10/2012 | Wilton et al. |
| 2013/0211062 A1 | 8/2013 | Watanabe et al. |
| 2014/0343266 A1 | 11/2014 | Watanabe et al. |
| 2015/0045413 A1 | 2/2015 | De Visser et al. |
| 2015/0191725 A1 | 7/2015 | van Deutekom |

FOREIGN PATENT DOCUMENTS

| | | |
|---|---|---|
| WO | WO-2004/083446 A2 | 9/2004 |
| WO | WO-2006/000057 A1 | 1/2006 |
| WO | WO-2007/135105 A1 | 11/2007 |
| WO | WO-2009/139630 A2 | 11/2009 |
| WO | WO-2010/048586 A1 | 4/2010 |
| WO | WO-2010/123369 A1 | 10/2010 |
| WO | WO-2011/057350 A1 | 5/2011 |
| WO | WO-2012/029986 A1 | 3/2012 |
| WO | WO-2012/109296 A1 | 8/2012 |
| WO | WO-2013/100190 A1 | 7/2013 |
| WO | WO-2013/112053 A1 | 8/2013 |
| WO | WO-2014/007620 A2 | 1/2014 |

OTHER PUBLICATIONS

Shin'Ichi Takeda, "Exon Skipping Approach to Duchenne Muscular Dystrophy," Symposium S-14: Opening Doors to Novel Therapeutics for Muscular Dystrophy, 55th Annual Meeting of the Japanese Society of Neurology, Program and Abstracts, May 2014, vol. 55, p. 269, including English translation.

Annemieke Aartsma-Rus, et al., "Targeted exon skipping as a potential gene correction therapy for Duchenne muscular dystrophy," (2002) Neuromuscular Disorders 12: S71-S77.

Tetsuya Nagata, et al., "Kin Dystorphy no Idenshi Chiryo," Curr. Insights Nuerol. Sci., 2013, vol. 19/20, pp. 20-21.

Shin'Ichi Takeda, "Exon Skipping Approach to Duchenne Muscular Dystrophy," Societas Neurologica Japonica Gakujutsu Taikai Program Shorokushu, May 2014, vol. 55, p. 269.

Steve D. Wilton, et al., "Antisense Oligonucleotide-induced Exon Skipping Across the Human Dystrophin Gene Transcript," Molecular Therapy 2007: 15: pp. 1288-1296.

International Search Report dated Sep. 1, 2015 for PCT/JP2015/067238.

[FIG. 1]
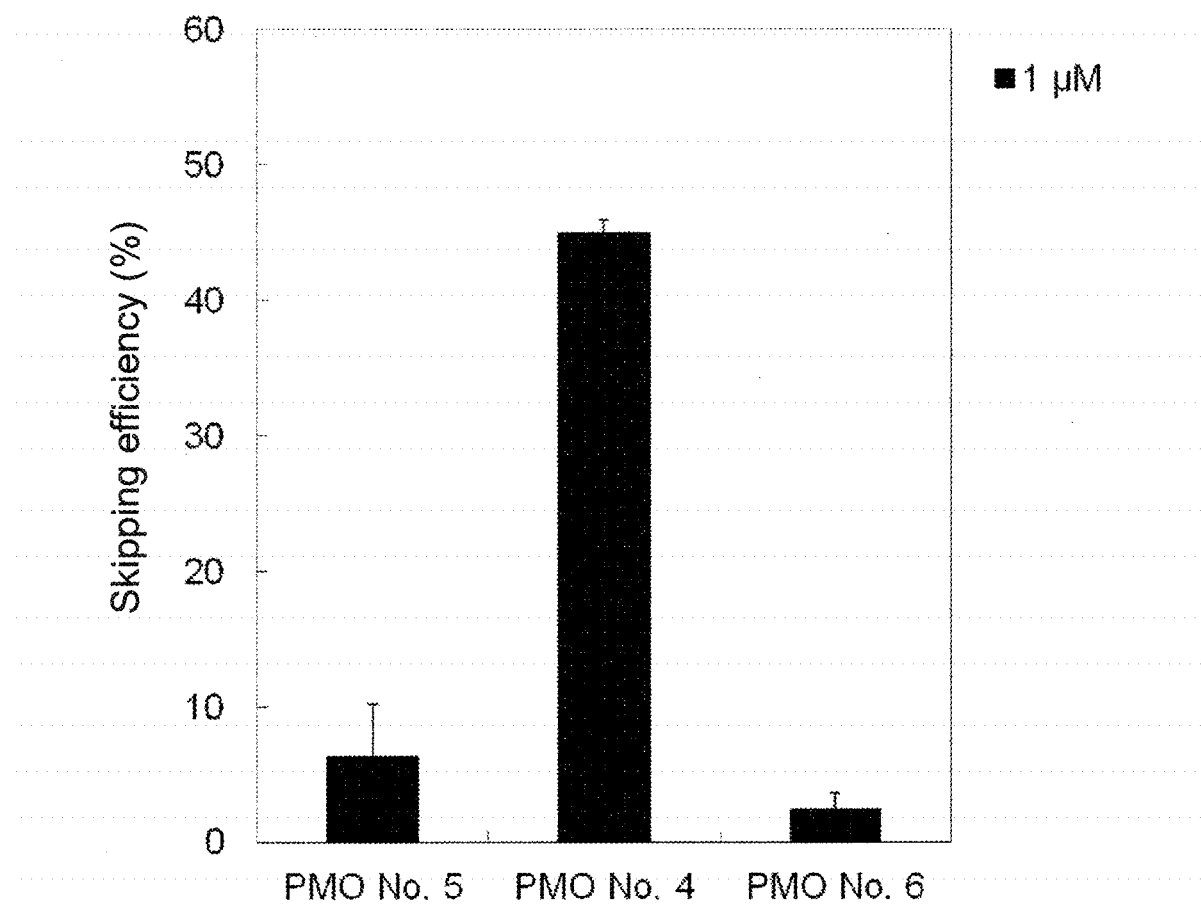

[FIG. 2]
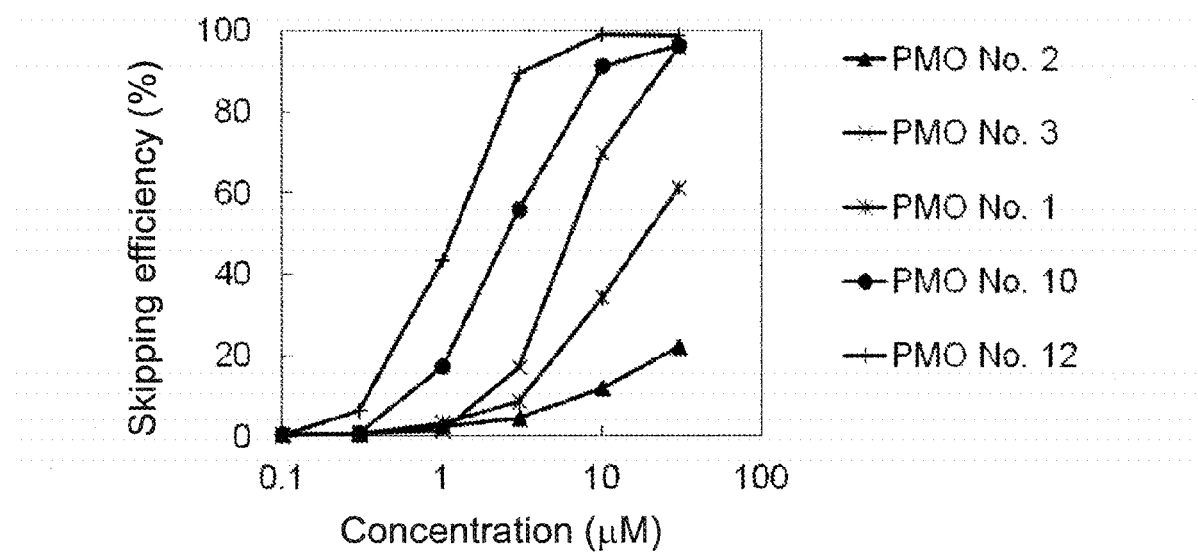
[FIG. 3]
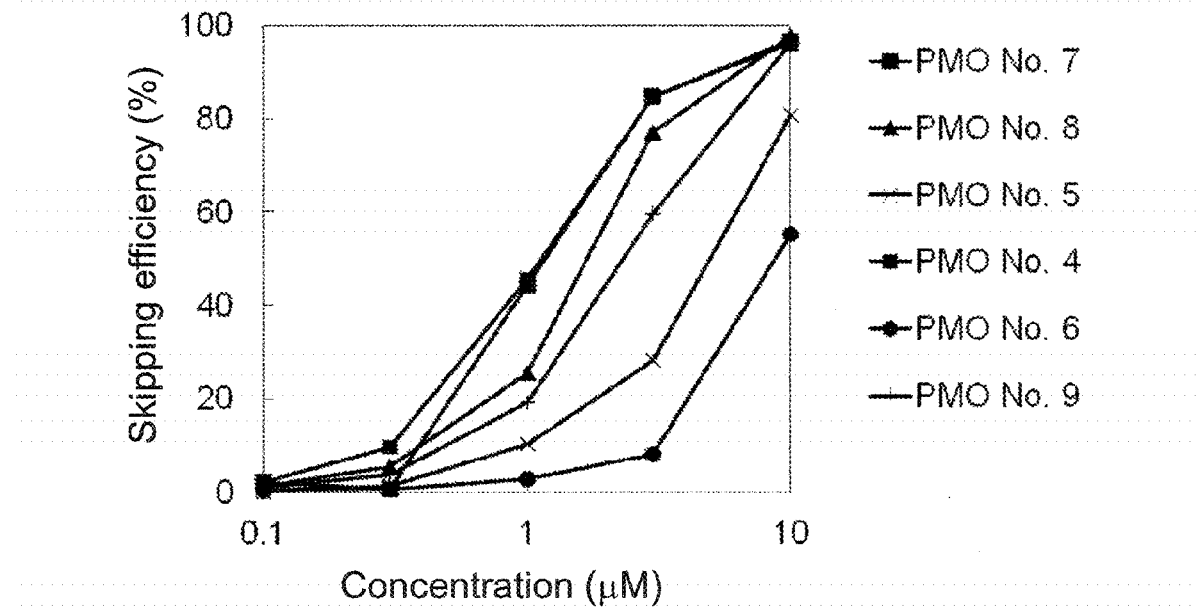

[FIG. 4]
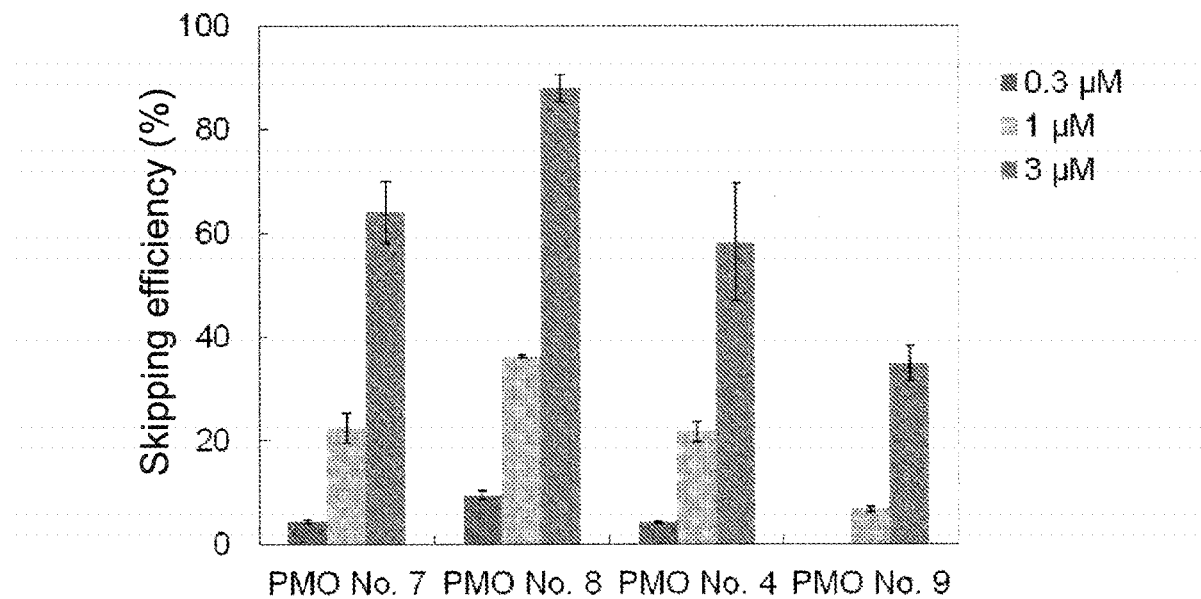
[FIG. 5]
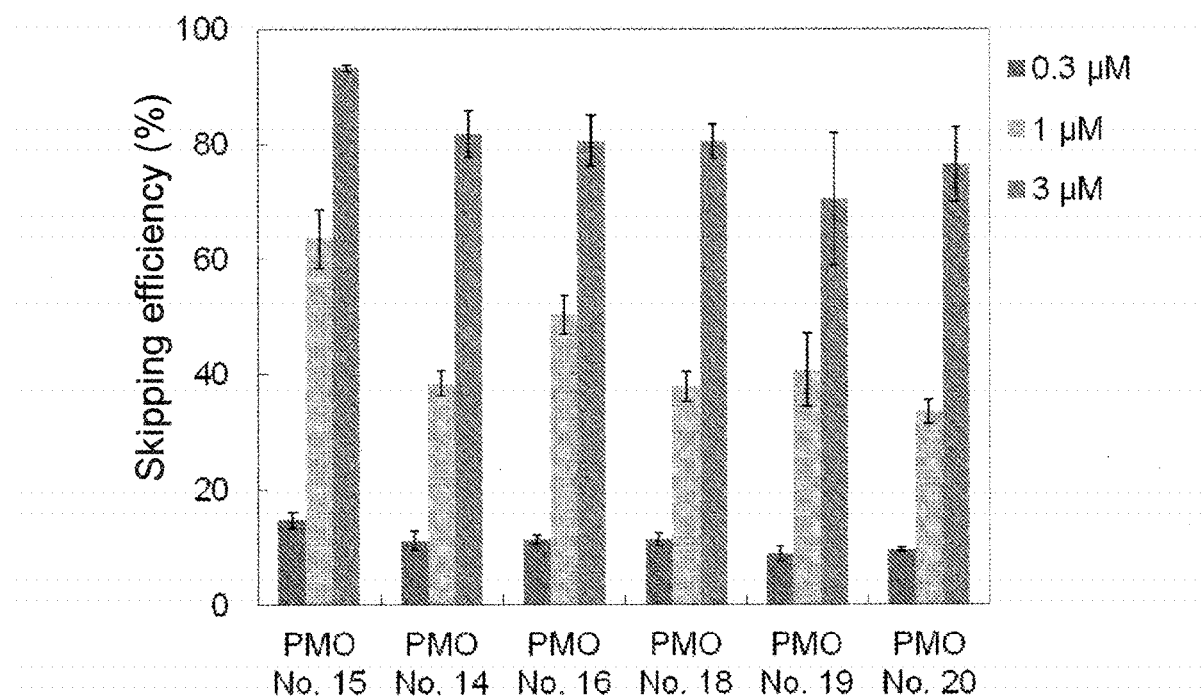

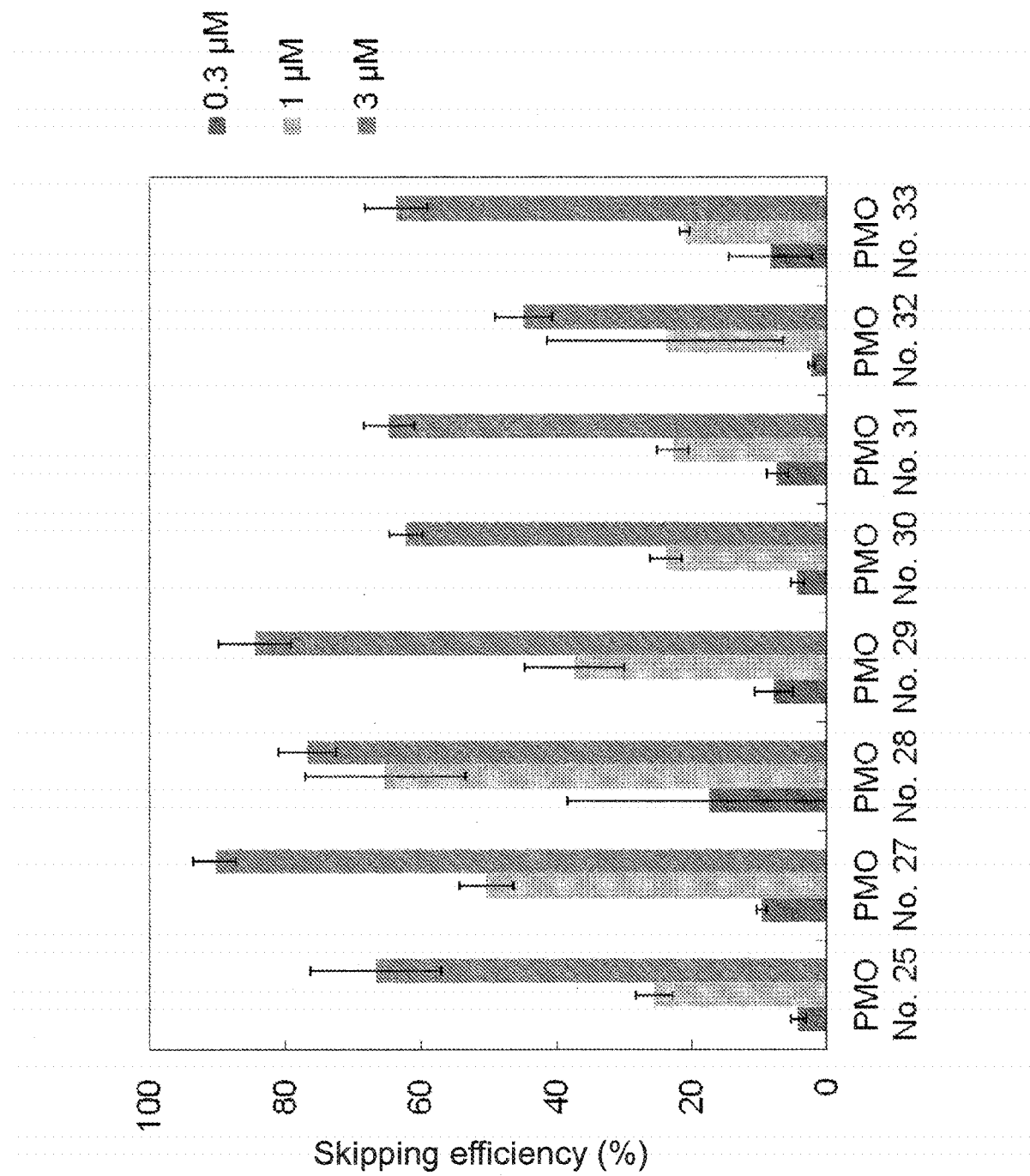
[FIG. 6]

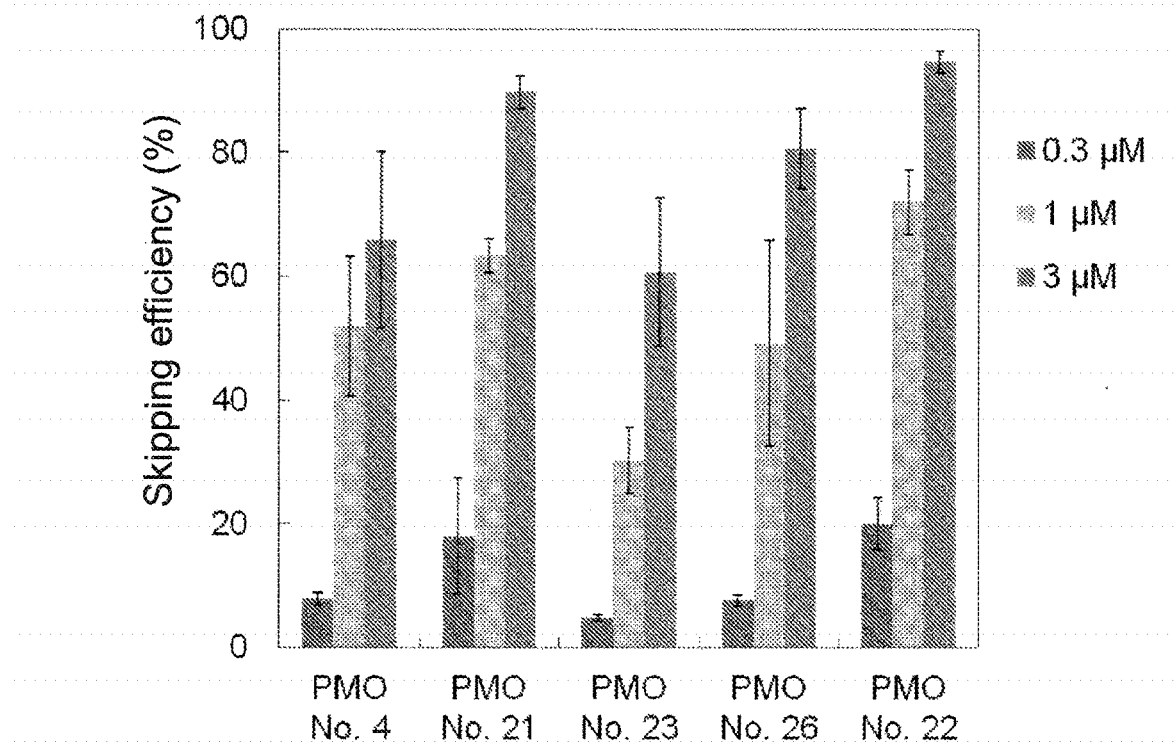
[FIG. 7]

[FIG. 8]
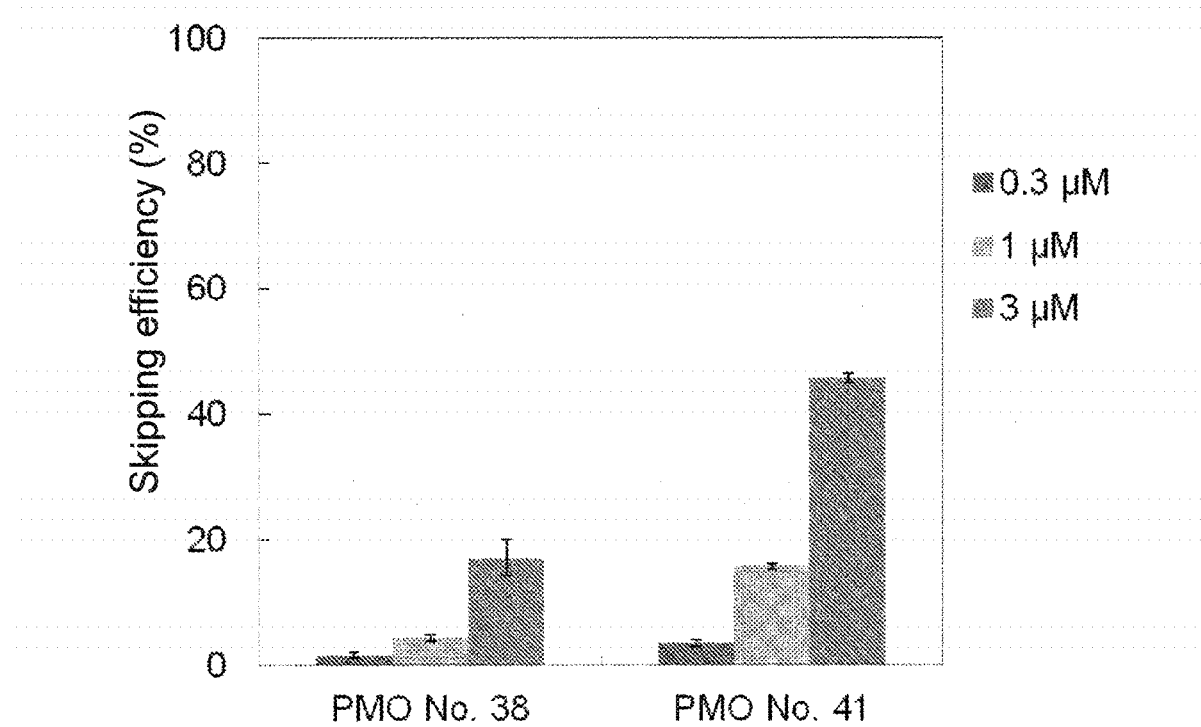

[FIG. 9]
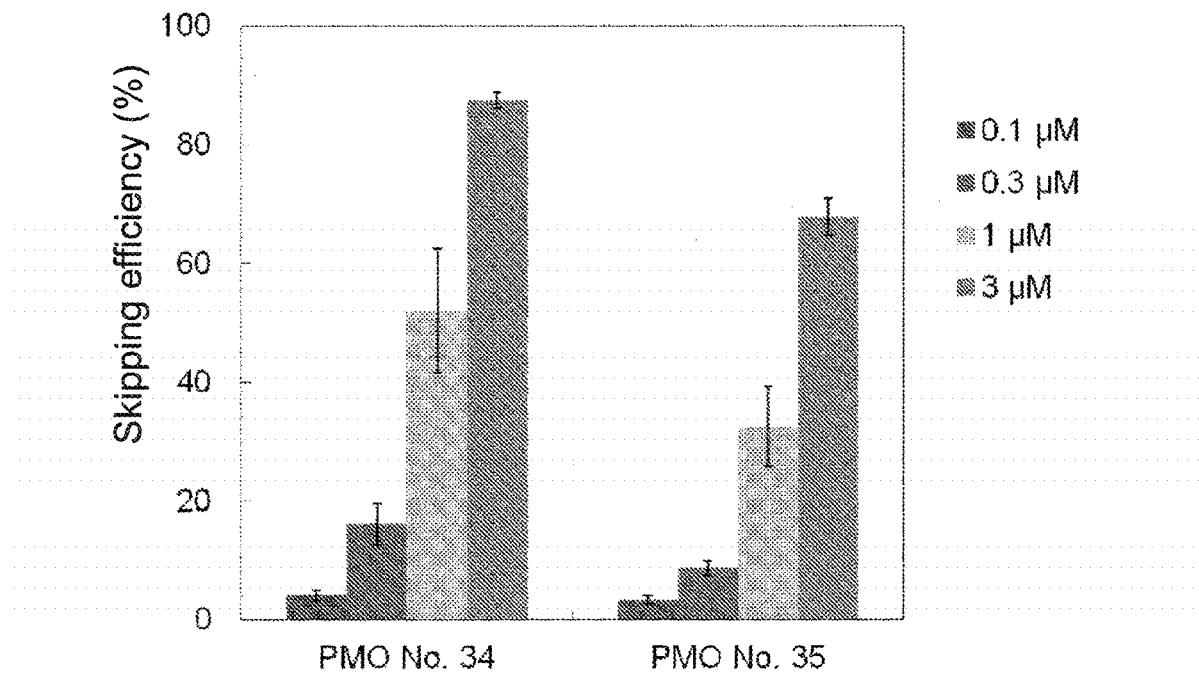
[FIG. 10]
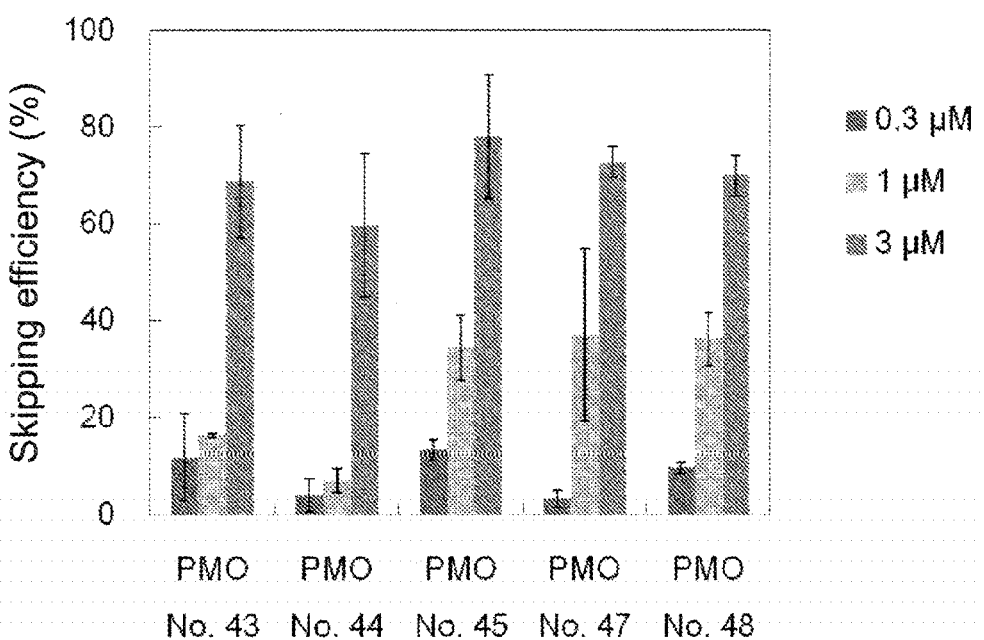

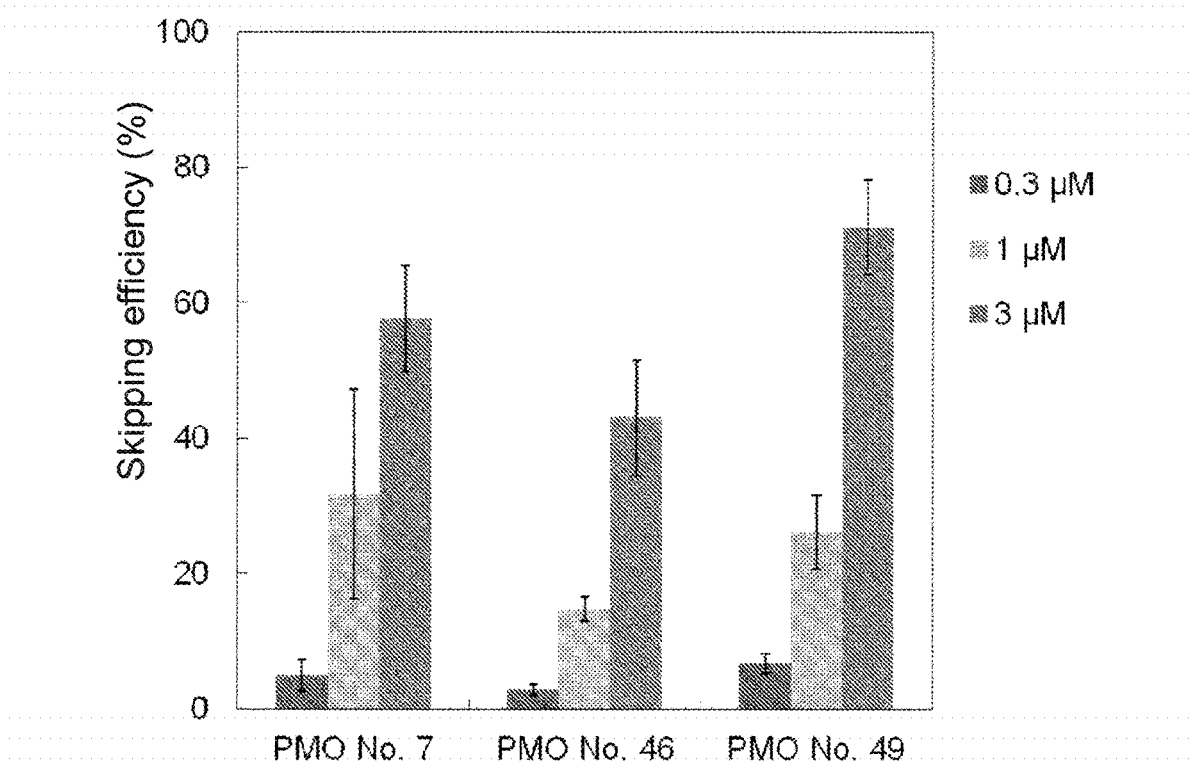
[FIG. 11]

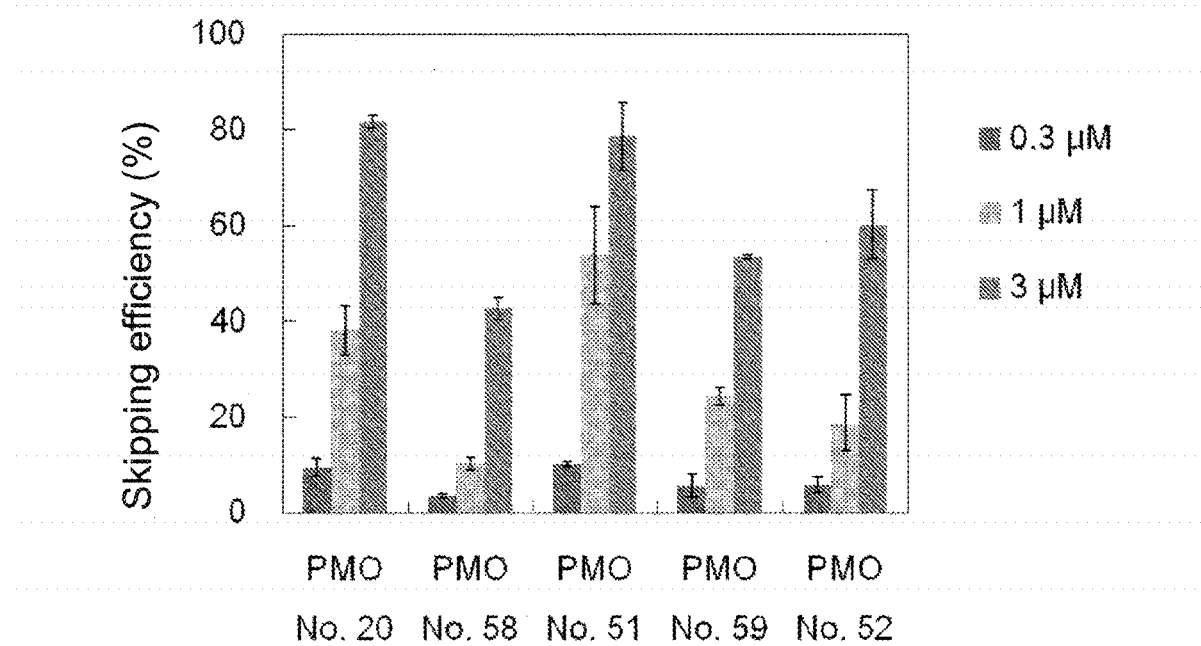

[FIG. 13]
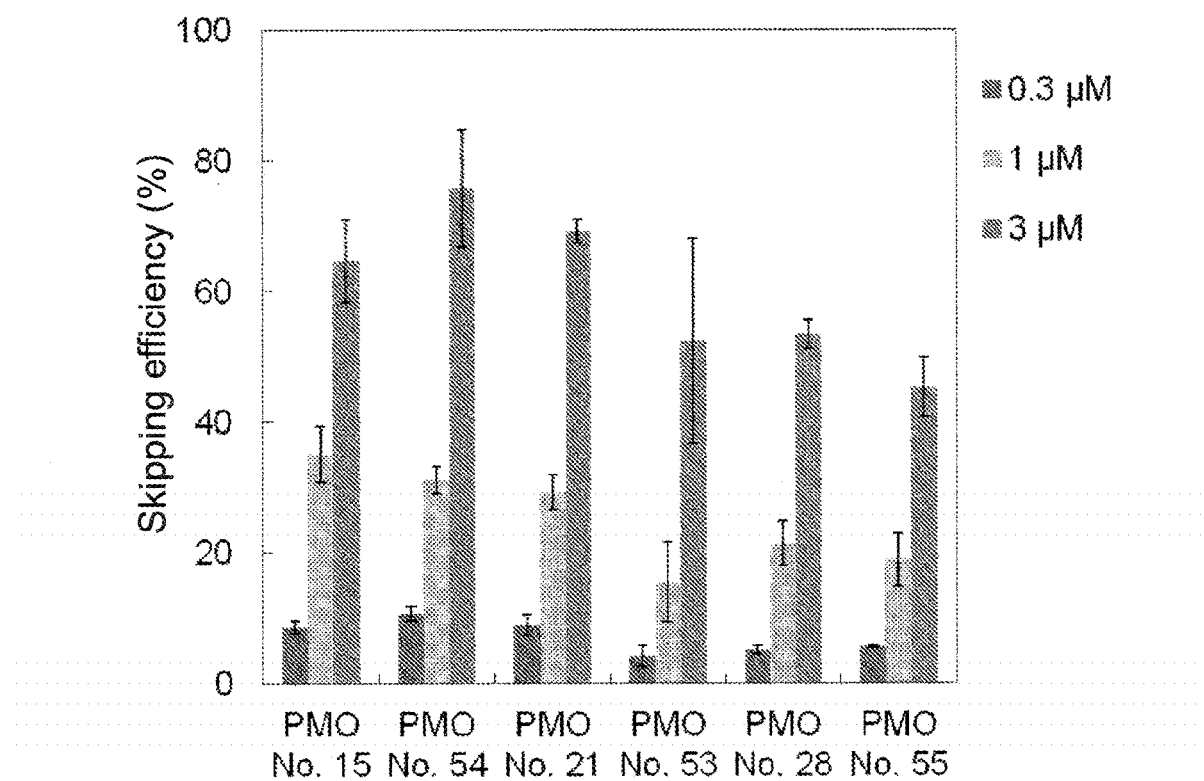

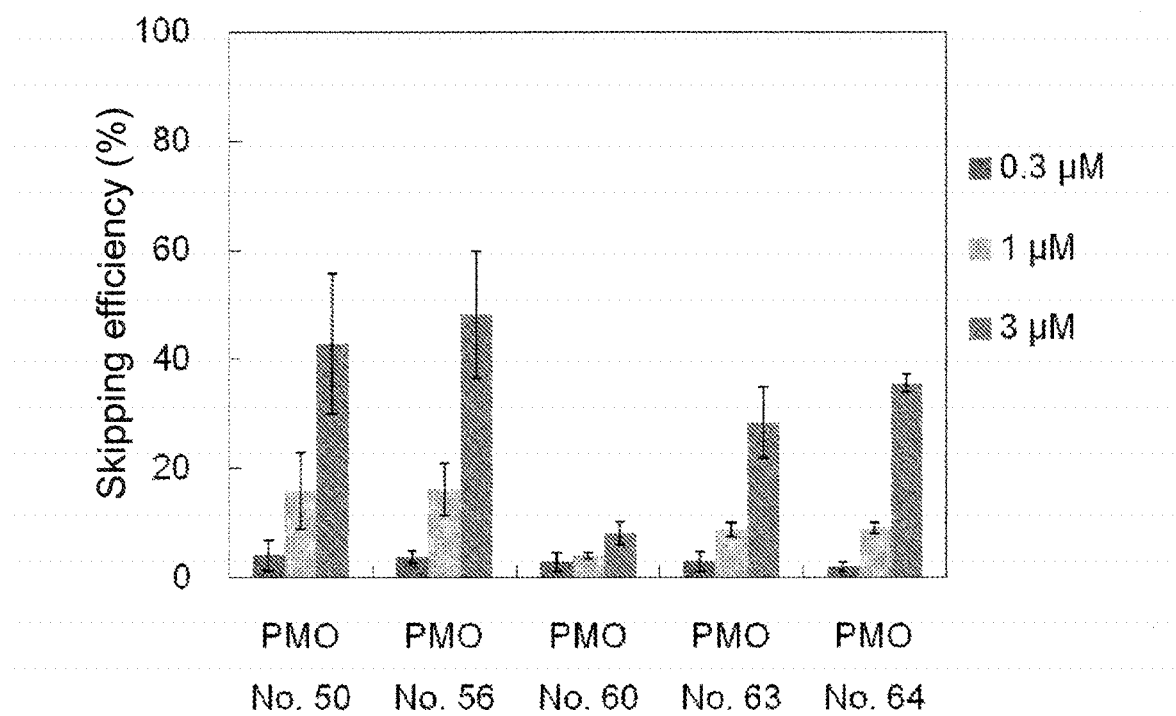

[FIG. 15]
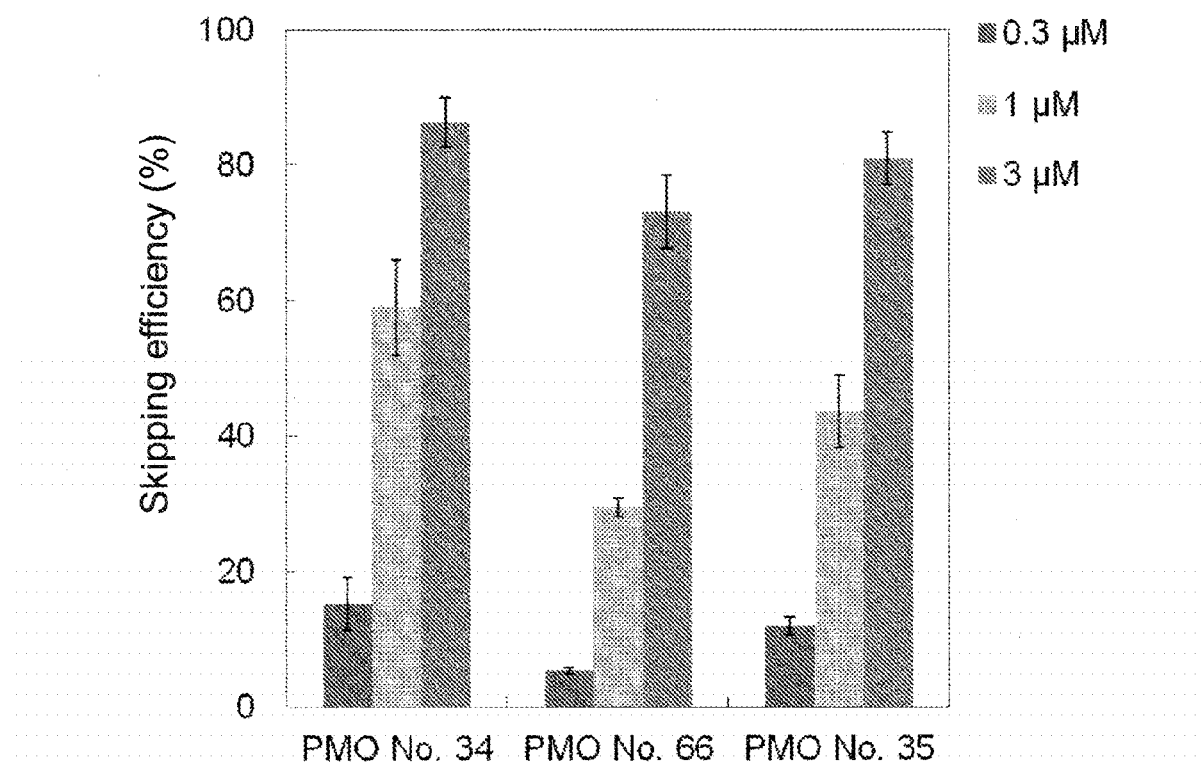

[FIG. 16]
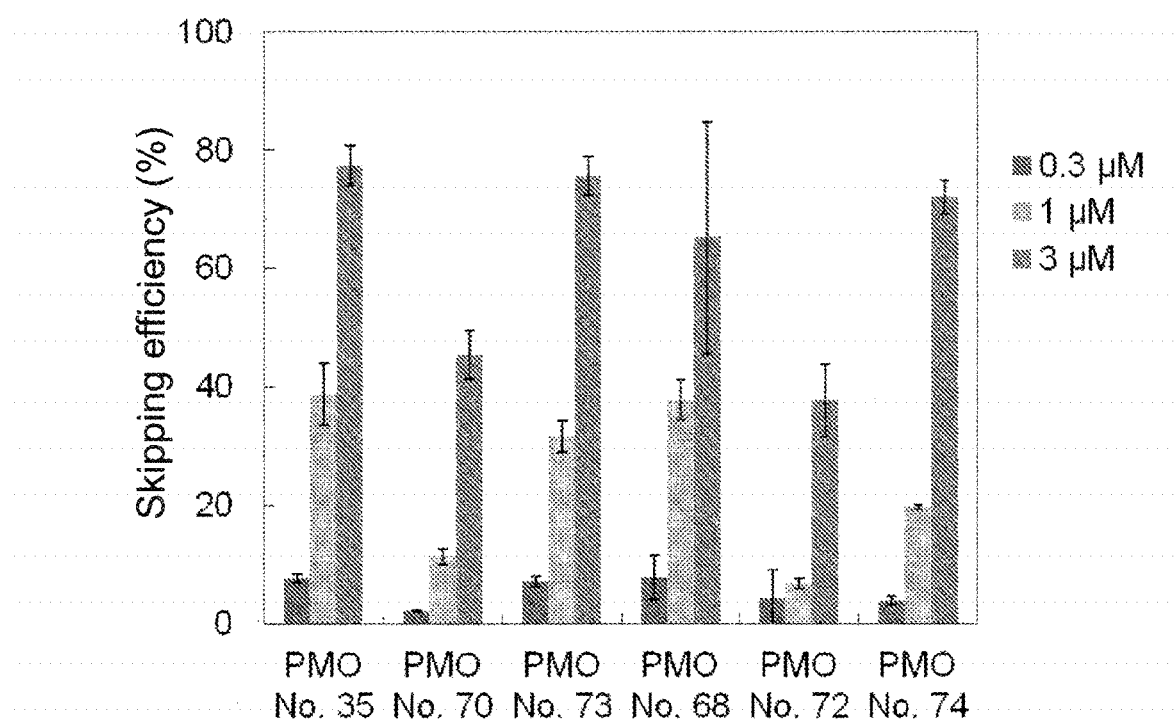

[FIG. 17]
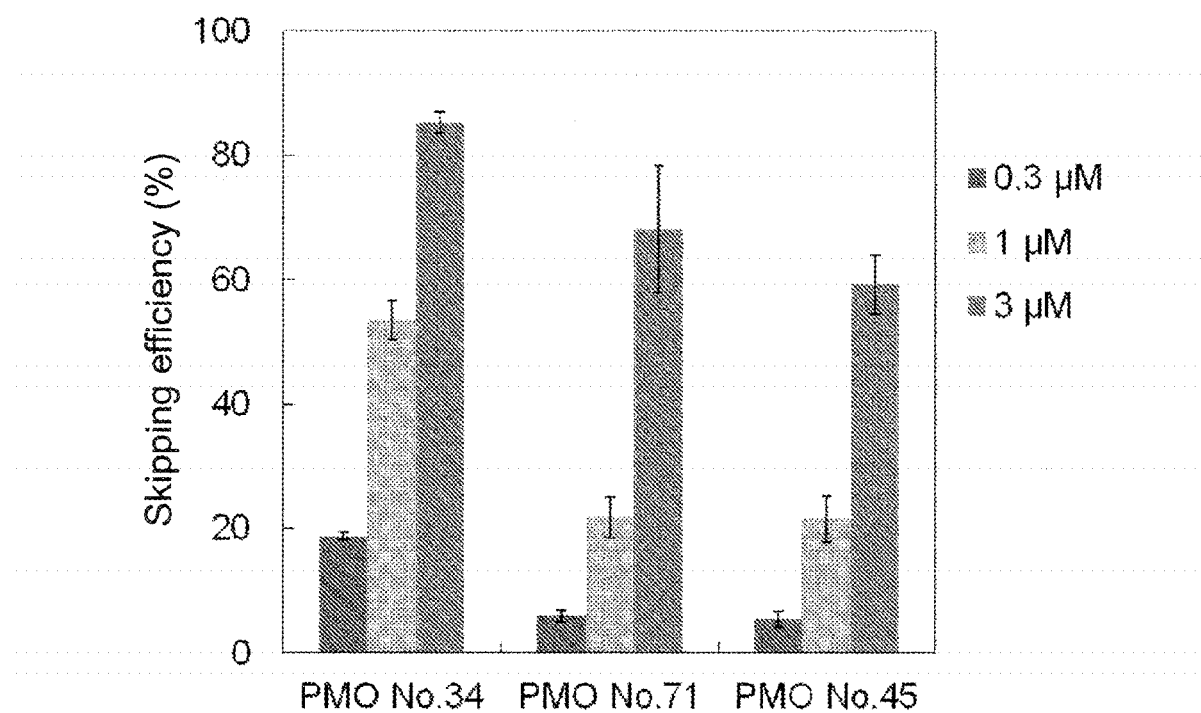

[FIG. 18]
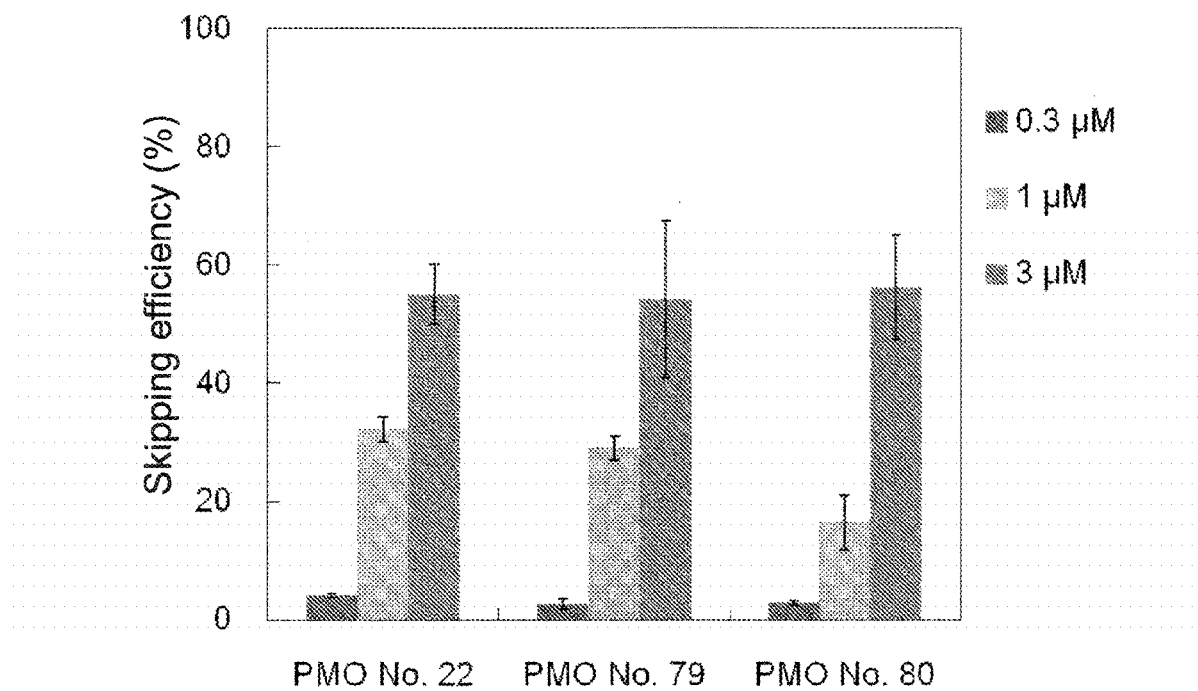
[FIG. 19]
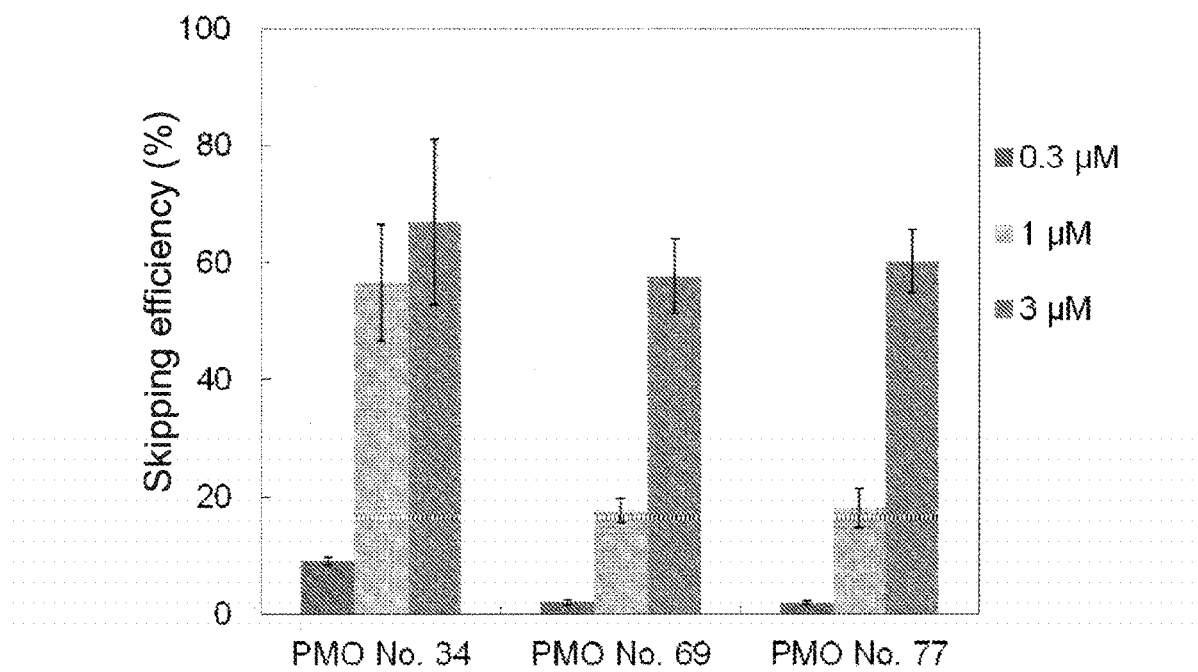

[FIG. 20]
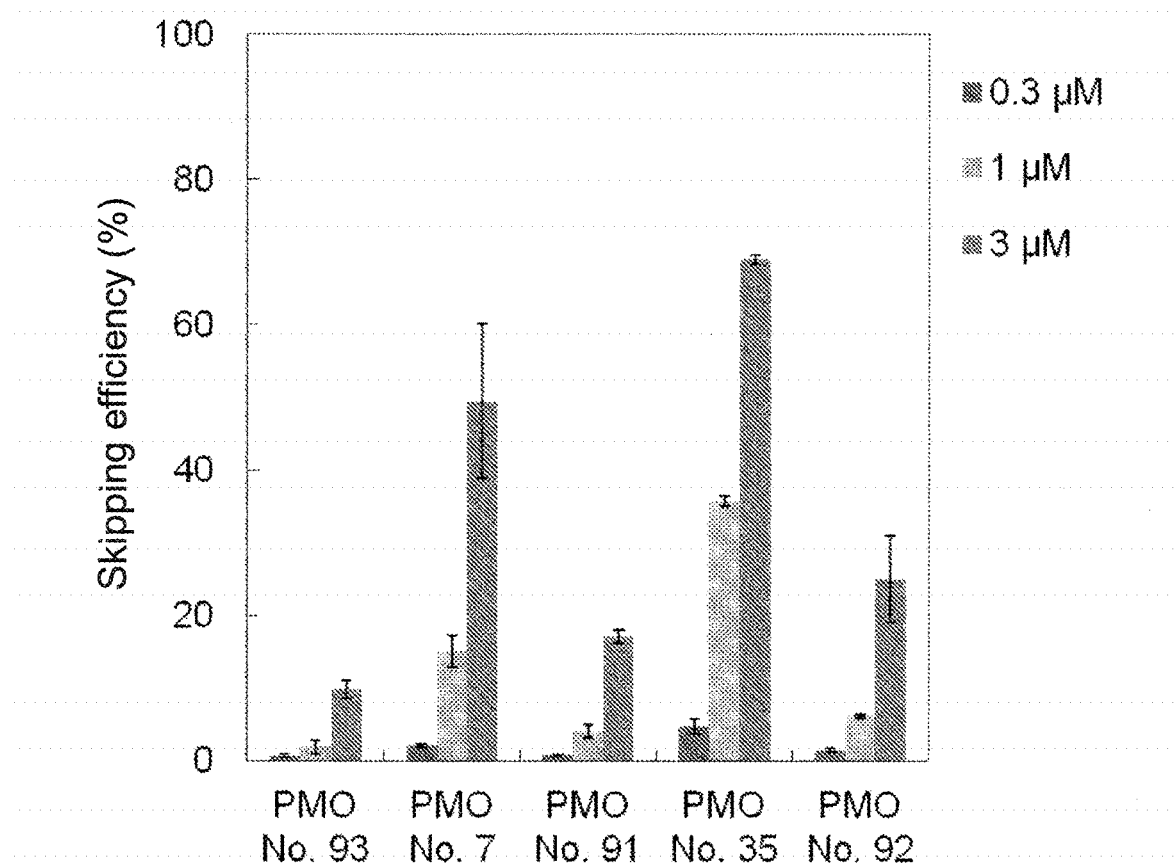

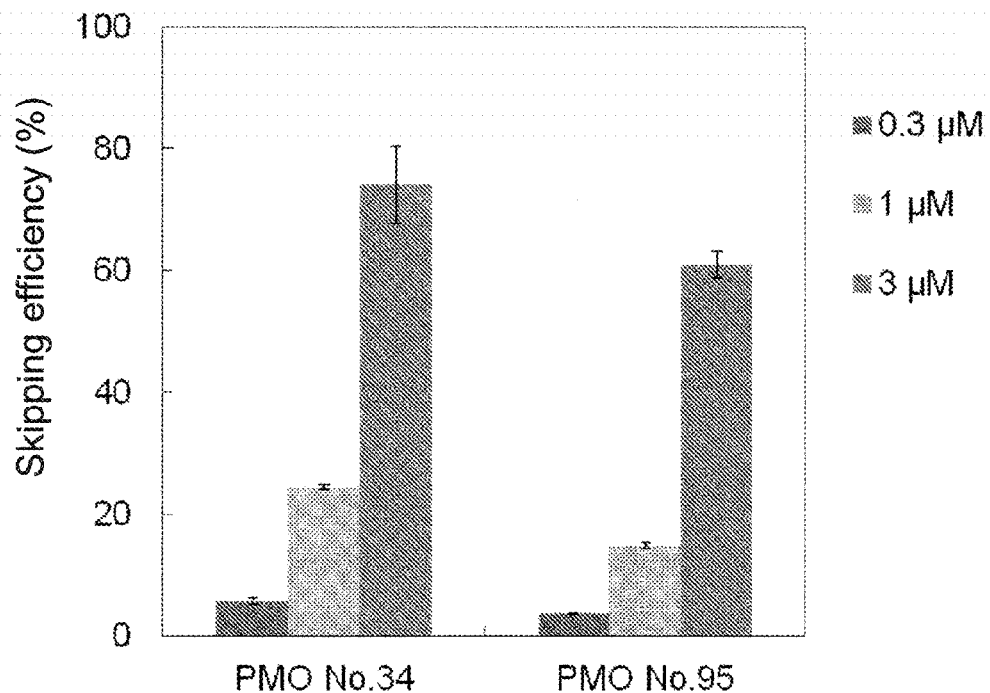
[FIG. 21]
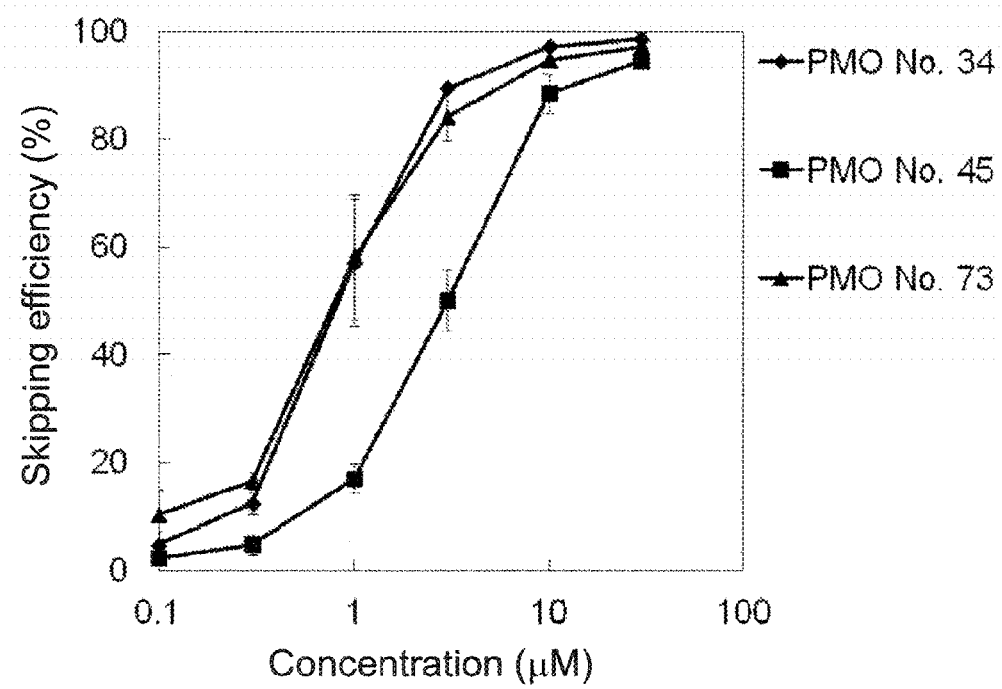
[FIG. 22]

[FIG. 23]
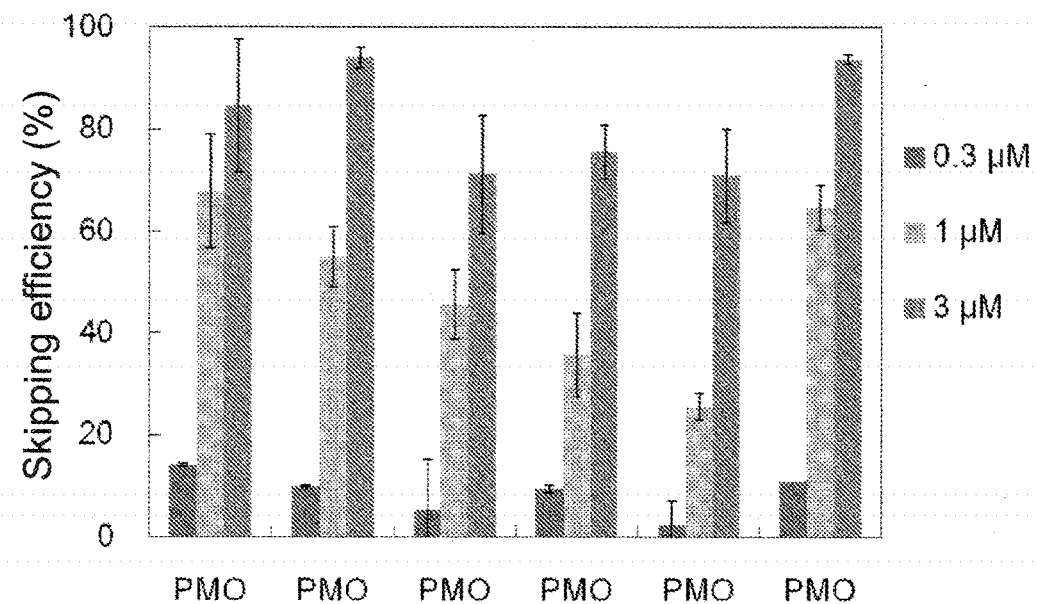
[FIG. 24]
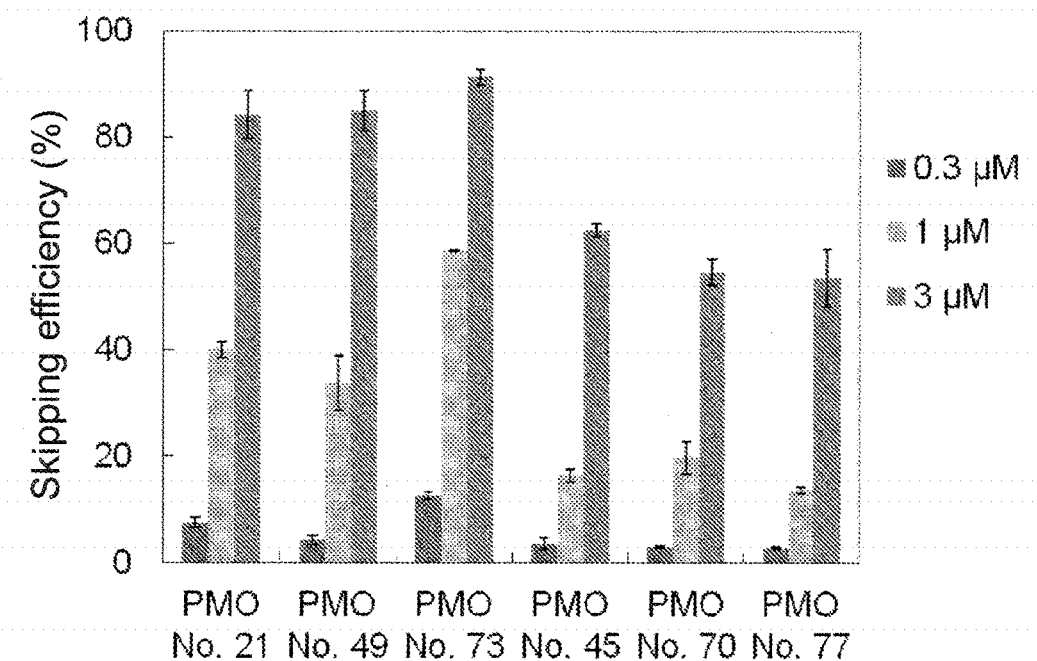

[FIG. 25]
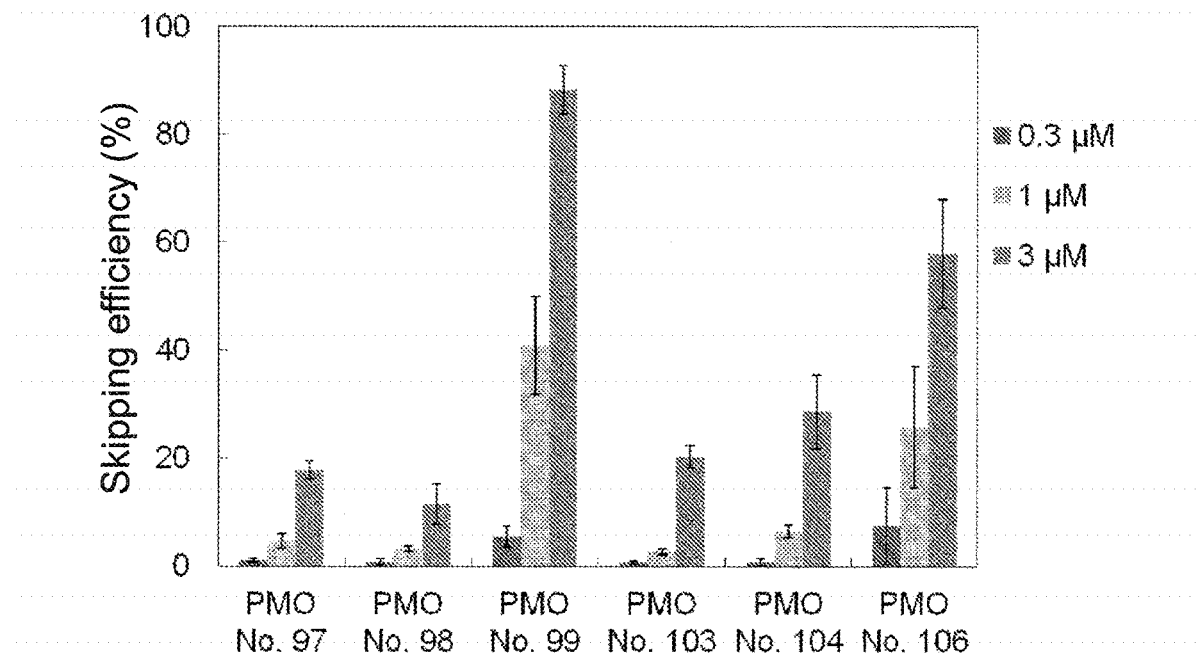
[FIG. 26]
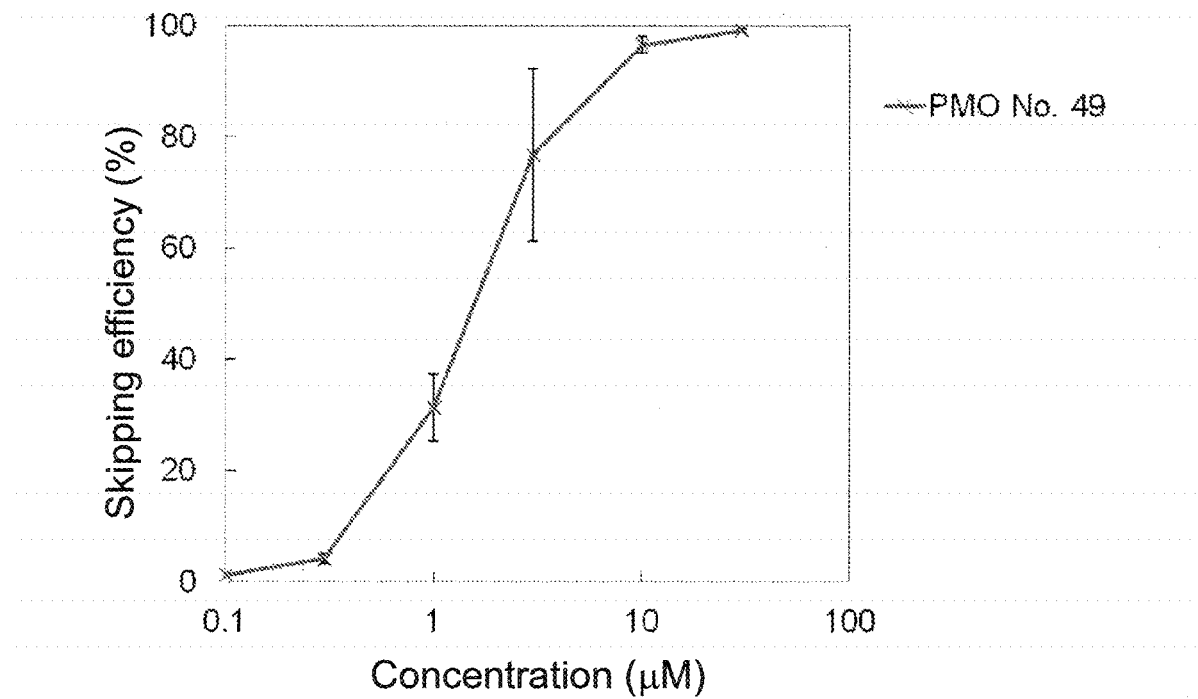

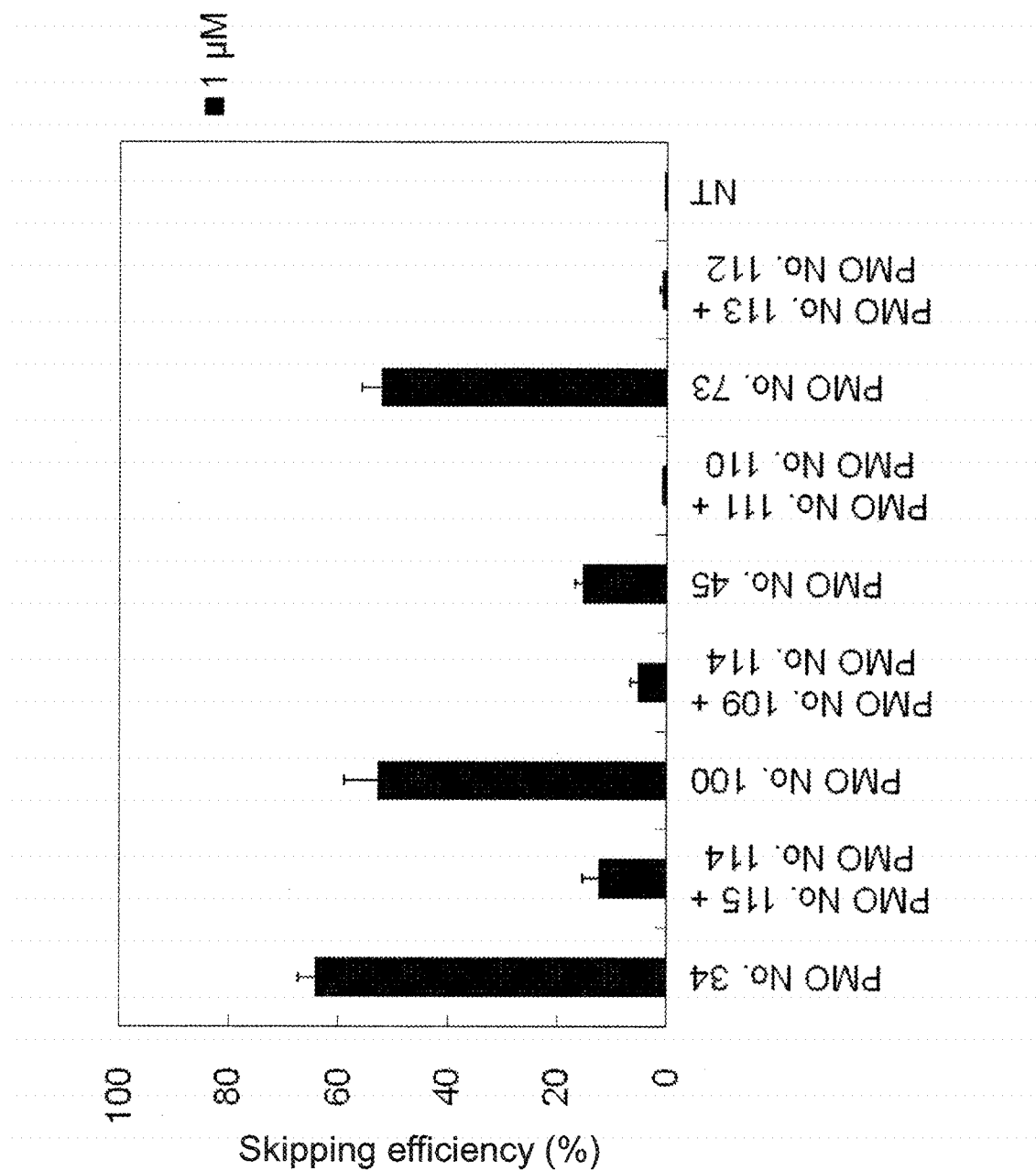
[FIG. 27]

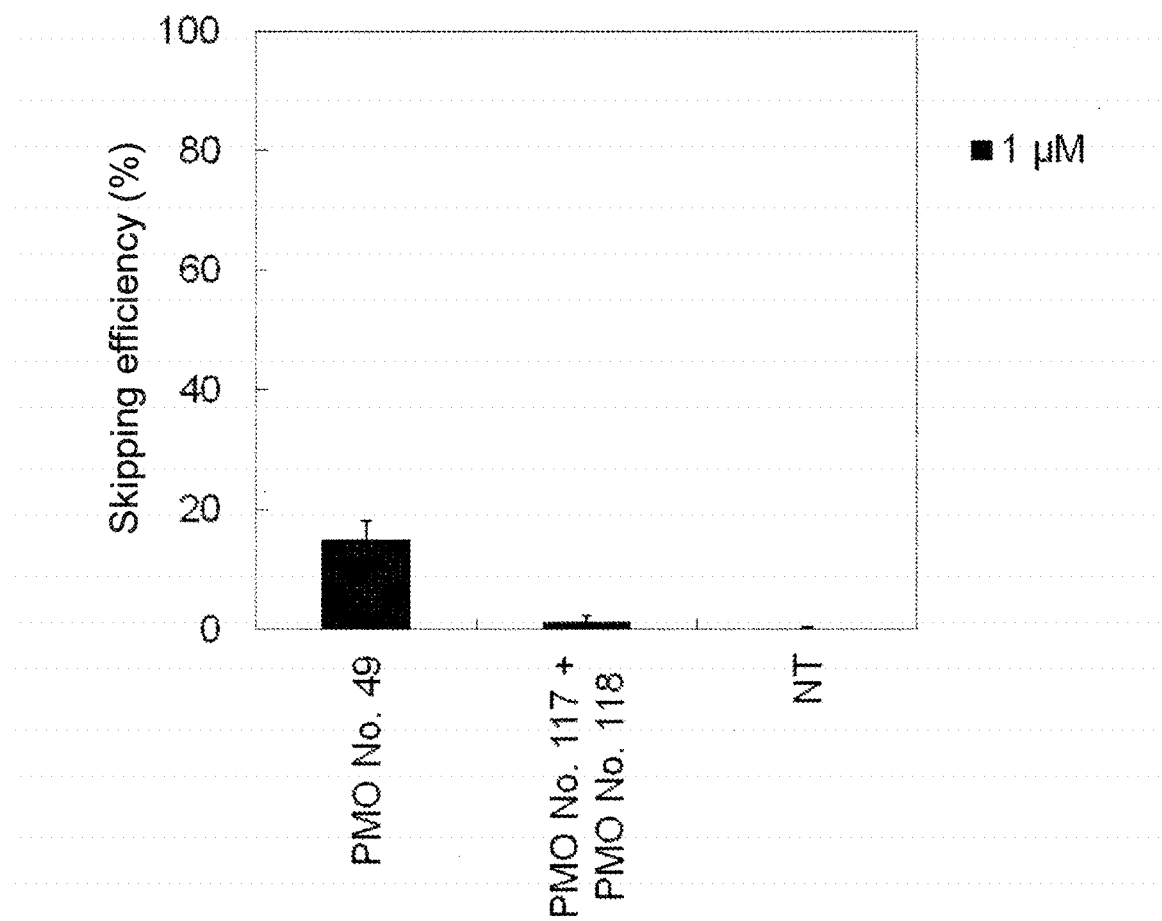
[FIG. 28]

[FIG. 29]
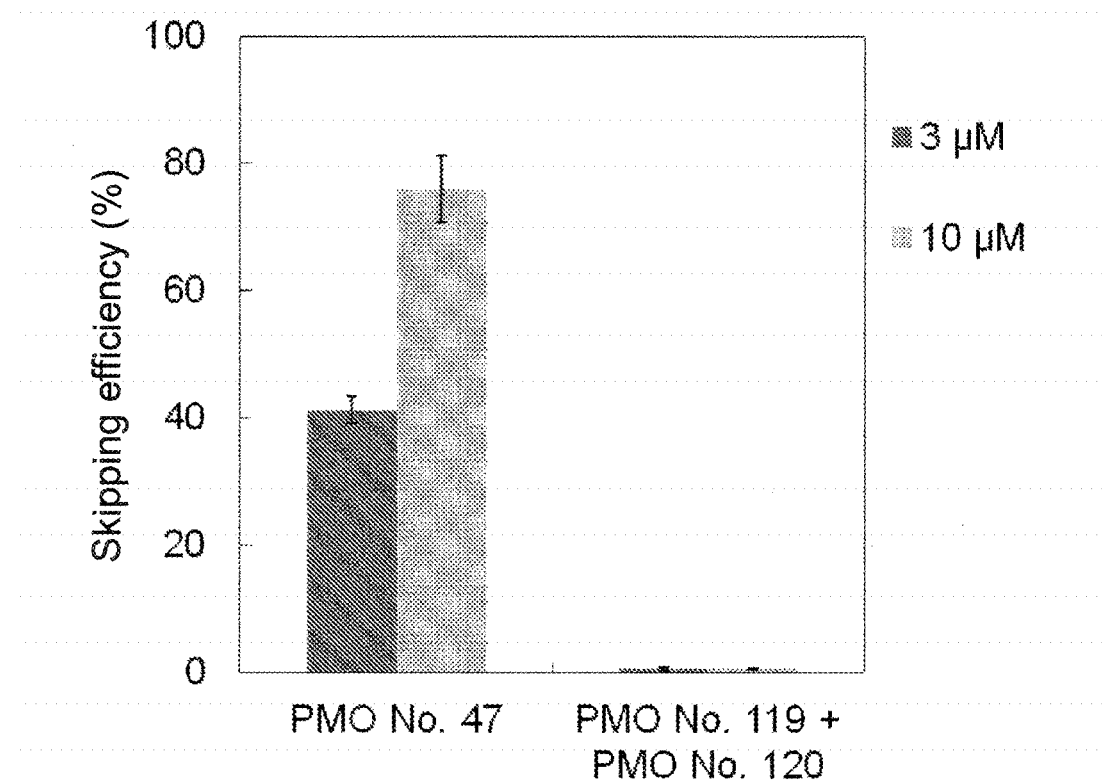

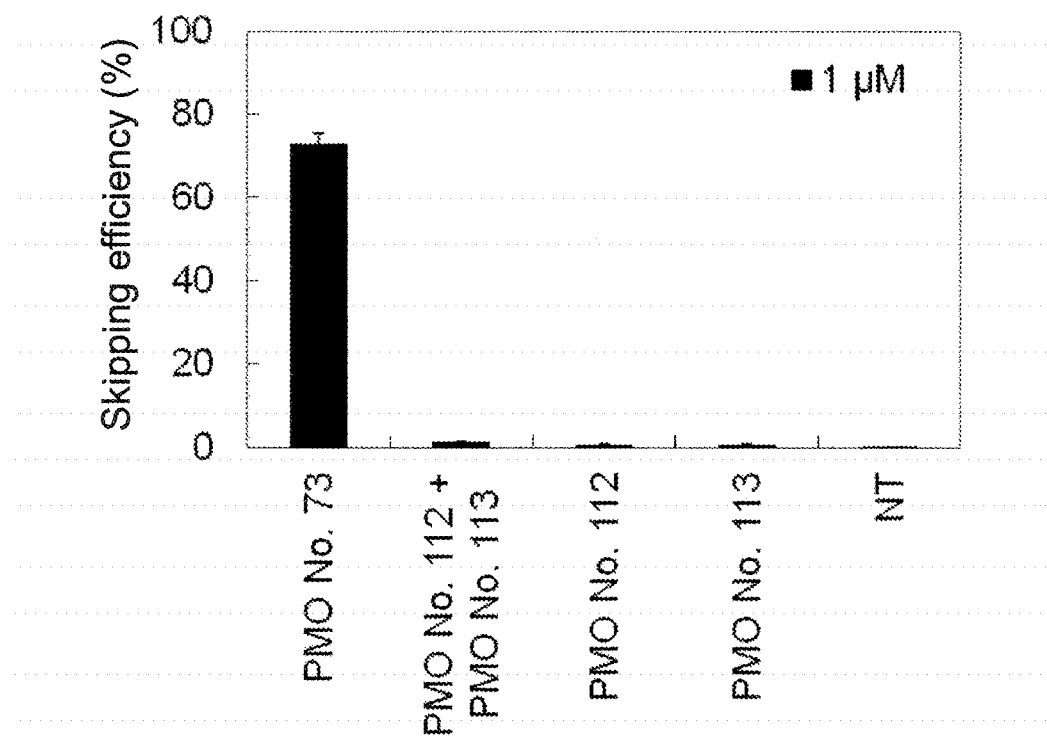
[FIG. 30]

[FIG. 31]
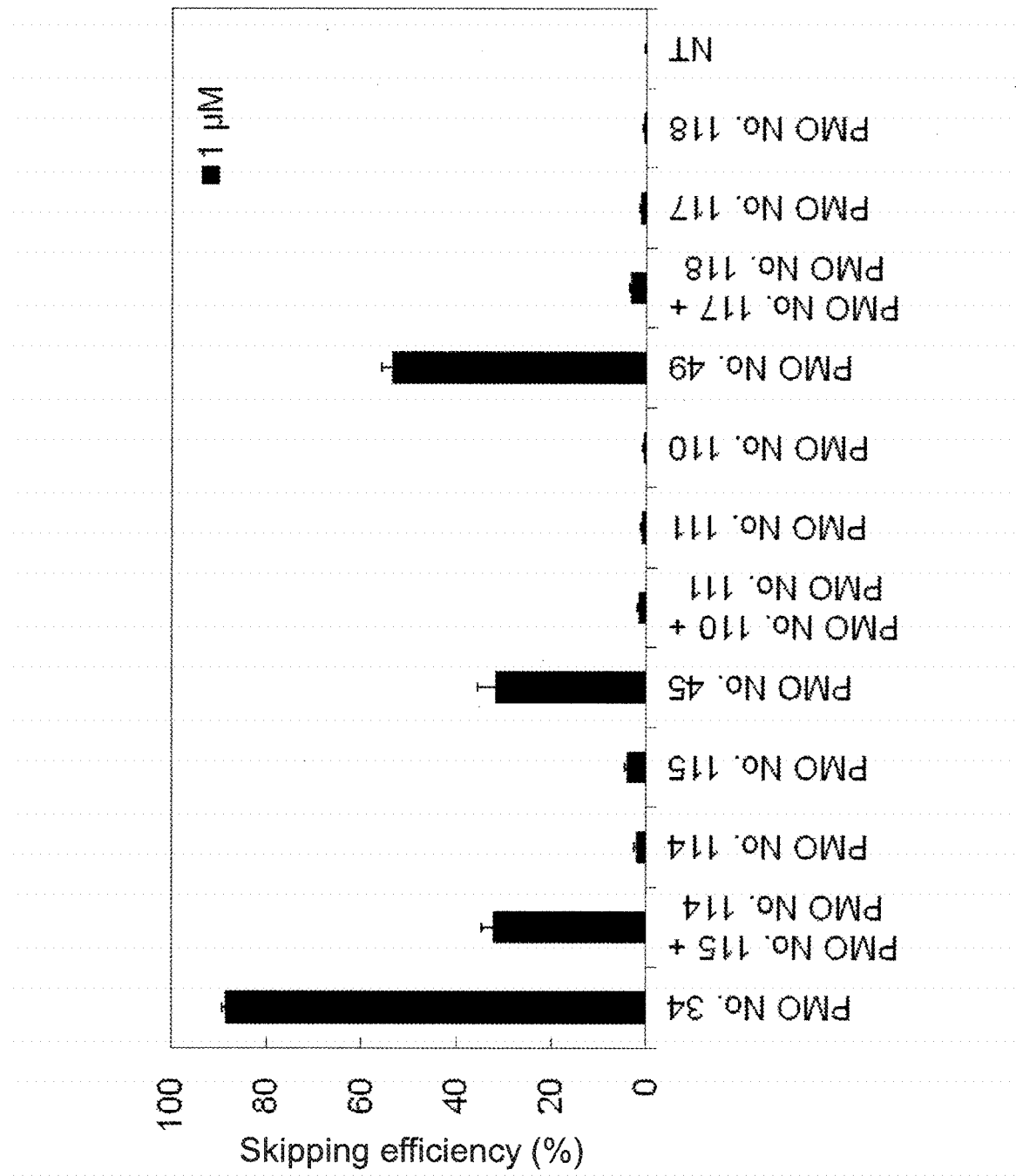

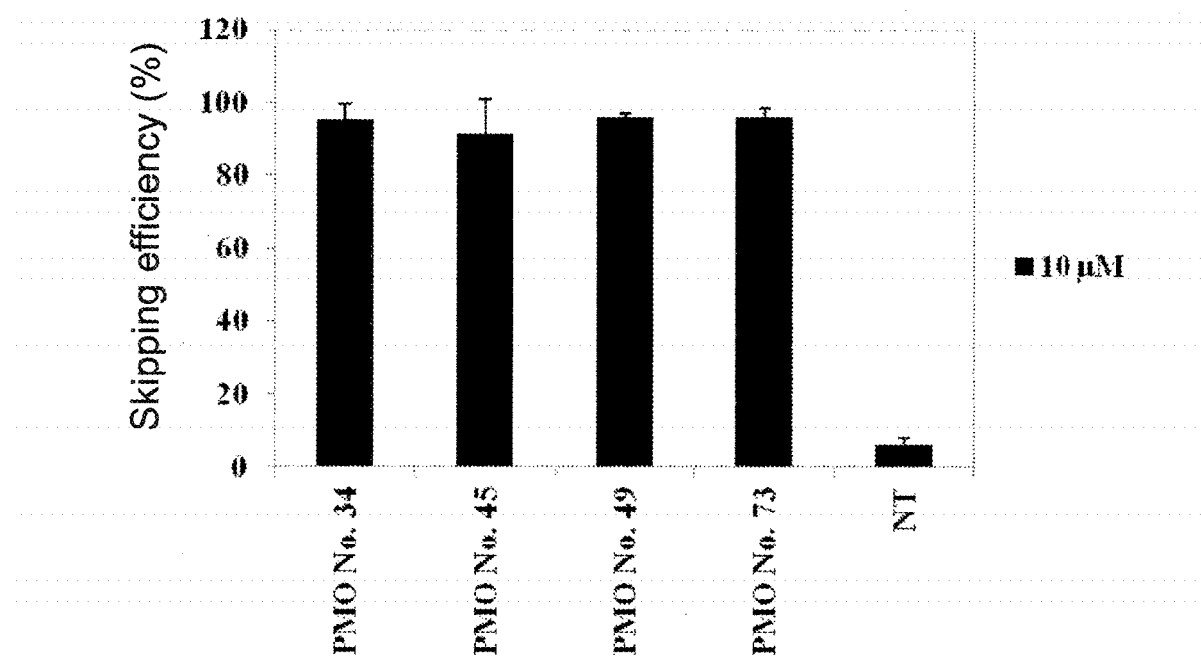
[FIG. 32]

ANTISENSE NUCLEIC ACIDS

CROSS REFERENCE TO RELATED APPLICATIONS

This application is the National Stage of International Application No. PCT/JP2015/067238, filed Jun. 16, 2015, and claims benefit of Japanese Application No. 2014-124157 filed on Jun. 17, 2014.

REFERENCE TO A SEQUENCE LISTING

The instant application contains a sequence listing which has been submitted in ASCII format via EFS-Web and is hereby incorporated by reference in its entirety. Said ASCII copy, created on Nov. 23, 2016, is named G1076WO_ST25.txt and is 31,454 bytes in size.

TECHNICAL FIELD

The present invention relates to an antisense oligomer for exon skipping, comprising a nucleotide sequence complementary to two or more different sequences in a target exon. More specifically, the present invention relates to an antisense oligomer which causes skipping of exon 44 in the human dystrophin gene, and a pharmaceutical composition comprising the oligomer.

Duchenne muscular dystrophy (DMD) is the most frequent form of hereditary progressive muscular dystrophy that affects one in about 3,500 newborn boys. Although the motor functions are rarely different from healthy humans in infancy and childhood, muscle weakness is observed in children from around 4 to 5 years old. Then, muscle weakness progresses to the loss of ambulation by about 12 years old and death due to cardiac or respiratory insufficiency in the twenties. DMD is such a severe disorder. At present, there is no effective therapy for DMD available, and it has been strongly desired to develop a novel therapeutic agent.

DMD is known to be caused by a mutation in the dystrophin gene. The dystrophin gene is located on X chromosome and is a huge gene consisting of 2.2 million DNA nucleotide pairs. DNA is transcribed into mRNA precursors, and introns are removed by splicing to synthesize mRNA of 13,993 bases, in which 79 exons are joined together. This mRNA is translated into 3,685 amino acids to produce the dystrophin protein. The dystrophin protein is associated with the maintenance of membrane stability in muscle cells and necessary to make muscle cells less fragile. The dystrophin gene from patients with DMD contains a mutation and hence, the dystrophin protein, which is functional in muscle cells, is rarely expressed. Therefore, the structure of muscle cells cannot be maintained in the body of the patients with DMD, leading to a large influx of calcium ions into muscle cells. Consequently, an inflammation-like response occurs to promote fibrosis so that muscle cells can be regenerated only with difficulty.

Becker muscular dystrophy (BMD) is also caused by a mutation in the dystrophin gene. The symptoms involve muscle weakness but are typically mild and slow in the progress of muscle weakness, when compared to DMD. In many cases, its onset is in adulthood. Differences in clinical symptoms between DMD and BMD are considered to reside in whether the reading frame for amino acids on the translation of dystrophin mRNA into the dystrophin protein is disrupted by the mutation or not (Non-Patent Document 1). More specifically, in DMD, the presence of mutation shifts the amino acid reading frame so that the expression of functional dystrophin protein is abolished, whereas in BMD the dystrophin protein that functions, though imperfectly, is produced because the amino acid reading frame is preserved, while a part of the exons are deleted by the mutation.

Exon skipping is expected to serve as a method for treating DMD. This method involves modifying splicing to restore the amino acid reading frame of dystrophin mRNA and induce expression of the dystrophin protein having the function partially restored (Non-Patent Document 2). The amino acid sequence part, which is a target for exon skipping, will be lost. For this reason, the dystrophin protein expressed by this treatment becomes shorter than normal one but since the amino acid reading frame is maintained, the function to stabilize muscle cells is partially retained. Consequently, it is expected that exon skipping will lead DMD to the similar symptoms to that of BMD which is milder. The exon skipping approach has passed the animal tests using mice or dogs and now is currently assessed in clinical trials on human DMD patients.

The skipping of an exon can be induced by binding of antisense nucleic acids targeting either 5' or 3' splice site or both sites, or exon-internal sites. An exon will only be included in the mRNA when both splice sites thereof are recognized by the spliceosome complex. Thus, exon skipping can be induced by targeting the splice sites with antisense nucleic acids. Furthermore, the binding of an SR protein, which is rich in serine and arginine, to an exonic splicing enhancer (ESE) is considered necessary for an exon to be recognized by the splicing mechanism. Accordingly, exon skipping can also be induced by targeting ESE.

Since a mutation of the dystrophin gene may vary depending on DMD patients, antisense nucleic acids need to be designed based on the site or type of respective genetic mutation. There are several reports on antisense nucleic acids that induce exon skipping with one consecutive sequence as a target for a single exon in the dystrophin gene (Patent Documents 1 to 6 and Non-Patent Documents 1 and 2). Also, it has been reported that when two types of antisense nucleic acids targeting the same exon in the dystrophin gene are mixed and allowed to act (dual targeting), skipping activity may be enhanced as compared with use of each antisense nucleic acid alone (Patent Document 7).

However, none of the previous reports show that a connected single strand antisense nucleic acid (connected type) targeting two or more sites in the same exon exhibits skipping activity (Patent Document 1).

PRIOR ART DOCUMENT

Patent Document

Patent Document 1: International Publication WO 2004/048570
Patent Document 2: International Publication WO 2009/139630
Patent Document 3: International Publication WO 2010/048586
Patent Document 4: US 2010/0168212
Patent Document 5: International Publication WO 2011/057350
Patent Document 6: International Publication WO 2006/000057
Patent Document 7: International Publication WO 2007/135105

Non-Patent Document

Non-Patent Document 1: Annemieke Aartsma-Rus et al., (2002) Neuromuscular Disorders 12: S71-S77

Non-Patent Document 2: Wilton S. D., et al., Molecular Therapy 2007: 15: p. 1288-96

DISCLOSURE OF THE INVENTION

Problems to be Solved by the Invention

Under these circumstances, a main object of the present invention is to provide a novel connected type antisense oligomer which induces exon skipping by targeting two different nucleotide sequences in the same exon in the dystrophin gene, and a therapeutic agent for muscular dystrophy comprising the oligomer.

Means for Solving the Problem

The present inventors have conducted extensive studies on the contents of the techniques described in the documents described above and the structure of the dystrophin gene, etc., and consequently found that an antisense oligomer obtained by connecting oligomers targeting two different sites in exon 44 in the human dystrophin gene can induce skipping of this exon. Based on this finding, the present inventors have accomplished the present invention.

That is, the present invention is as follows.

[1]
An antisense oligomer having a length of 15 to 30 bases wherein (a) a first unit oligomer comprising a nucleotide sequence complementary to a first nucleotide sequence of 7 to 15 consecutive bases in a target exon; and (b) a second unit oligomer comprising a nucleotide sequence complementary to a second nucleotide sequence of 7 to 15 consecutive bases in the target exon are connected, wherein the first nucleotide sequence and the second nucleotide sequence are neither consecutive nor overlap with each other, and the antisense oligomer induces skipping of the target exon, or a pharmaceutically acceptable salt or hydrate thereof.

[2]
The antisense oligomer according to [1], wherein the first and/or second unit oligomer comprises a nucleotide sequence complementary to a partial nucleotide sequence of an intron adjacent to the target exon, or a pharmaceutically acceptable salt or hydrate thereof.

[3]
The antisense oligomer according to [1] or [2], wherein the target exon is an exon in human dystrophin gene, or a pharmaceutically acceptable salt or hydrate thereof.

[4]
The antisense oligomer according to [1] or [2], wherein the first nucleotide sequence is a nucleotide sequence of 7 to 15 consecutive bases selected from the nucleotide sequence represented by SEQ ID NO: 1, or a pharmaceutically acceptable salt or hydrate thereof.

[5]
The antisense oligomer according to any one of [1] to [3], wherein the second nucleotide sequence is a nucleotide sequence of 7 to 15 consecutive bases selected from the nucleotide sequence represented by SEQ ID NO: 2, or a pharmaceutically acceptable salt or hydrate thereof.

[6]
The antisense oligomer according to [1] or [2], wherein two unit oligomers selected from the group consisting of the following (c) to (e) are connected:

(c) a unit oligomer consisting of a nucleotide sequence complementary to a nucleotide sequence of 7 to 15 consecutive bases selected from the nucleotide sequence represented by SEQ ID NO: 3;

(d) a unit oligomer consisting of a nucleotide sequence complementary to a nucleotide sequence of 7 to 15 consecutive bases selected from the nucleotide sequence represented by SEQ ID NO: 4; and (e) a unit oligomer consisting of a nucleotide sequence complementary to a nucleotide sequence of 7 to 15 consecutive bases selected from the nucleotide sequence represented by SEQ ID NO: 5, or a pharmaceutically acceptable salt or hydrate thereof.

[7]
The antisense oligomer according to [1] or [2], which consists of a nucleotide sequence selected from a group consisting of SEQ ID Nos: 6 to 9, or a pharmaceutically acceptable salt or hydrate thereof.

[8]
The antisense oligomer according to any one of [1] to [7], which is an oligonucleotide, or a pharmaceutically acceptable salt or hydrate thereof.

[9]
The antisense oligomer according to [8], wherein the sugar moiety and/or the phosphate-binding region of at least one nucleotide constituting the oligonucleotide is modified, or a pharmaceutically acceptable salt or hydrate thereof.

[10]
The antisense oligomer according to [8] or [9], wherein the sugar moiety of at least one nucleotide constituting the oligonucleotide is a ribose in which the 2'-OH group is replaced by any one selected from the group consisting of OR, R, R'OR, SH, SR, $NH_2$, NHR, $NR_2$, $N_3$, CN, F, Cl, Br and I (wherein R is an alkyl or an aryl and R' is an alkylene), or a pharmaceutically acceptable salt or hydrate thereof.

[11]
The antisense oligomer according to any one of [8] to [10], wherein the phosphate-binding region of at least one nucleotide constituting the oligonucleotide is any one selected from the group consisting of a phosphorothioate bond, a phosphorodithioate bond, an alkylphosphonate bond, a phosphoramidate bond and a boranophosphate bond, or a pharmaceutically acceptable salt or hydrate thereof.

[12]
The antisense oligomer according to any one of [1] to [7], which is a morpholino oligomer, or a pharmaceutically acceptable salt or hydrate thereof.

[13]
The antisense oligomer according to claim [12], which is a morpholino oligomer, or a pharmaceutically acceptable salt or hydrate thereof.

[14]
The antisense oligomer according to [12] or [13], wherein the 5' end is any one of chemical formulae (1) to (3) below, or a pharmaceutically acceptable salt or hydrate thereof.

[Formula 1]

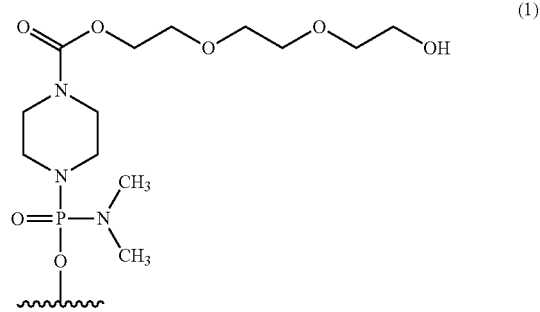

(1)

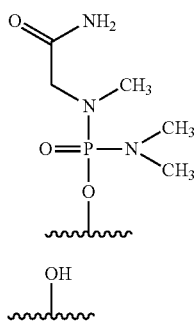

A pharmaceutical composition for the treatment of muscular dystrophy, comprising as an active ingredient the antisense oligomer according to any one of [1] to [14], or a pharmaceutically acceptable salt or hydrate thereof.

[16]

The pharmaceutical composition according to [15], comprising a pharmaceutically acceptable carrier.

[17]

A method for treatment of muscular dystrophy, which comprises providing to a patient with muscular dystrophy the antisense oligomer or a pharmaceutically acceptable salt or hydrate thereof according to any one of [1] to [12] or the pharmaceutical composition according to [1] or [16].

[18]

The method for treatment according to [17], wherein the patient with muscular dystrophy has a mutation(s) which is to be targeted for exon 44 skipping in gystrophin gene.

[19]

The method for treatment according to [17] or [18], wherein the patient is a human.

[20]

The use of the antisense oligomer or a pharmaceutically acceptable salt or hydrate thereof according to any one of [1] to [14] in manufacturing of the pharmaceutical composition for the treatment of muscular dystrophy.

[21]

The antisense oligomer, or a pharmaceutically acceptable salt or hydrate thereof according to any one of [1] to [14], that is applied for the treatment of muscular dystrophy.

[22]

The antisense oligomer, or a pharmaceutically acceptable salt or hydrate thereof according to [21] wherein the patient with muscular dystrophy in the said treatment has a mutation(s) which is to be targeted for exon 44 skipping in gystrophin gene.

[23]

The antisense oligomer according to [21] or [22], or a pharmaceutically acceptable salt or hydrate thereof, wherein the patient is a human.

[24]

A method for manufacturing of the antisense oligomer according to [1], which comprises connecting (a) a first unit oligomer comprising a nucleotide sequence complementary to a first nucleotide sequence of 7 to 15 consecutive bases in a target exon; and (b) a second unit oligomer comprising a nucleotide sequence complementary to a second nucleotide sequence of 7 to 15 consecutive bases in the target exon to produce an antisense oligomer having a length of 15 to 30 bases, wherein the first nucleotide sequence and the second nucleotide sequence are neither consecutive nor overlap with each other.

The method according to [24], which further comprises: measuring the efficiency of skipping by the obtained antisense oligomer; and selecting an antisense oligomer having the efficiency of skipping that exceeds a reference value.

[26]

A method for screening of an antisense oligomer, which comprises:

(a) selecting (i) a first unit oligomer comprising a nucleotide sequence complementary to a first nucleotide sequence of 7 to 15 consecutive bases in a target exon; and (ii) a second unit oligomer comprising a nucleotide sequence complementary to a second nucleotide sequence of 7 to 15 consecutive bases in the target exon, wherein the first nucleotide sequence and the second nucleotide sequence are neither consecutive nor overlap with each other;

(b) connecting the first and second unit oligomers to produce an antisense oligomer having a length of 15 to 30 bases;

(c) measuring the efficiency of skipping by the antisense oligomer obtained in the step (b); and (d) selecting an antisense oligomer having the efficiency of skipping that exceeds a reference value.

Effects of the Invention

The antisense oligomer of the present invention can induce skipping of exon 44 in the human dystrophin gene with a high efficiency. Also, the symptoms of Duchenne muscular dystrophy can be effectively alleviated by administering the pharmaceutical composition of the present invention.

BRIEF DESCRIPTION OF DRAWINGS

FIG. 1 shows the efficiency of exon 44 skipping in the human dystrophin gene in human rhabdomyosarcoma cell line (RD cells).

FIG. 2 shows the efficiency of exon 44 skipping in the human dystrophin gene in human rhabdomyosarcoma cells (RD cells) at the respective concentrations of the oligomers.

FIG. 3 shows the efficiency of exon 44 skipping in the human dystrophin gene in human rhabdomyosarcoma cells (RD cells) at the respective concentrations of the oligomers.

FIG. 4 shows the efficiency of exon 44 skipping in the human dystrophin gene in human rhabdomyosarcoma cells (RD cells) at the respective concentrations of the oligomers.

FIG. 5 shows the efficiency of exon 44 skipping in the human dystrophin gene in human rhabdomyosarcoma cells (RD cells) at the respective concentrations of the oligomers.

FIG. 6 shows the efficiency of exon 44 skipping in the human dystrophin gene in human rhabdomyosarcoma cells (RD cells) at the respective concentrations of the oligomers.

FIG. 7 shows the efficiency of exon 44 skipping in the human dystrophin gene in human rhabdomyosarcoma cells (RD cells) at the respective concentrations of the oligomers.

FIG. 8 shows the efficiency of exon 44 skipping in the human dystrophin gene in human rhabdomyosarcoma cells (RD cells) at the respective concentrations of the oligomers.

FIG. 9 shows the efficiency of exon 44 skipping in the human dystrophin gene in human rhabdomyosarcoma cells (RD cells) at the respective concentrations of the oligomers.

FIG. 10 shows the efficiency of exon 44 skipping in the human dystrophin gene in human rhabdomyosarcoma cells (RD cells) at the respective concentrations of the oligomers.

FIG. 11 shows the efficiency of exon 44 skipping in the human dystrophin gene in human rhabdomyosarcoma cells (RD cells) at the respective concentrations of the oligomers.

FIG. 12 shows the efficiency of exon 44 skipping in the human dystrophin gene in human rhabdomyosarcoma cells (RD cells) at the respective concentrations of the oligomers.

FIG. 13 shows the efficiency of exon 44 skipping in the human dystrophin gene in human rhabdomyosarcoma cells (RD cells) at the respective concentrations of the oligomers.

FIG. 14 shows the efficiency of exon 44 skipping in the human dystrophin gene in human rhabdomyosarcoma cells (RD cells) at the respective concentrations of the oligomers.

FIG. 15 shows the efficiency of exon 44 skipping in the human dystrophin gene in human rhabdomyosarcoma cells (RD cells) at the respective concentrations of the oligomers.

FIG. 16 shows the efficiency of exon 44 skipping in the human dystrophin gene in human rhabdomyosarcoma cells (RD cells) at the respective concentrations of the oligomers.

FIG. 17 shows the efficiency of exon 44 skipping in the human dystrophin gene in human rhabdomyosarcoma cells (RD cells) at the respective concentrations of the oligomers.

FIG. 18 shows the efficiency of exon 44 skipping in the human dystrophin gene in human rhabdomyosarcoma cells (RD cells) at the respective concentrations of the oligomers.

FIG. 19 shows the efficiency of exon 44 skipping in the human dystrophin gene in human rhabdomyosarcoma cells (RD cells) at the respective concentrations of the oligomers.

FIG. 20 shows the efficiency of exon 44 skipping in the human dystrophin gene in human rhabdomyosarcoma cells (RD cells) at the respective concentrations of the oligomers.

FIG. 21 shows the efficiency of exon 44 skipping in the human dystrophin gene in human rhabdomyosarcoma cells (RD cells) at the respective concentrations of the oligomers.

FIG. 22 shows the efficiency of exon 44 skipping in the human dystrophin gene in human rhabdomyosarcoma cells (RD cells) at the respective concentrations of the oligomers.

FIG. 23 shows the efficiency of exon 44 skipping in the human dystrophin gene in human rhabdomyosarcoma cells (RD cells) at the respective concentrations of the oligomers.

FIG. 24 shows the efficiency of exon 44 skipping in the human dystrophin gene in human rhabdomyosarcoma cells (RD cells) at the respective concentrations of the oligomers.

FIG. 25 shows the efficiency of exon 44 skipping in the human dystrophin gene in human rhabdomyosarcoma cells (RD cells) at the respective concentrations of the oligomers.

FIG. 26 shows the efficiency of exon 44 skipping in the human dystrophin gene in human rhabdomyosarcoma cells (RD cells) at the respective concentrations of the oligomers.

FIG. 27 shows a comparison of the efficiency of exon 44 skipping in the human dystrophin gene in human rhabdomyosarcoma cells (RD cells) between a connected form and a mixture of two unit oligomers targeting different sites.

FIG. 28 shows a comparison of the efficiency of exon 44 skipping in the human dystrophin gene in human rhabdomyosarcoma cells (RD cells) between a connected form and a mixture of two unit oligomers targeting different sites.

FIG. 29 shows a comparison of the efficiency of exon 44 skipping in the human dystrophin gene in human rhabdomyosarcoma cells (RD cells) between a connected form and a mixture of two unit oligomers targeting different sites.

FIG. 30 shows a comparison of the efficiency of exon 44 skipping in the human dystrophin gene in human rhabdomyosarcoma cells (RD cells) among each alone, a connected form and a mixture of two unit oligomers targeting different sites.

FIG. 31 shows a comparison of the efficiency of exon 44 skipping in the human dystrophin gene in human rhabdomyosarcoma cells (RD cells) among each alone, a connected form and a mixture of two unit oligomers targeting different sites.

FIG. 32 shows the efficiency of exon 44 skipping in the human dystrophin gene in the fibroblasts from human DMD patient with deletion of exon 45.

MODE FOR CARRYING OUT THE INVENTION

Hereinafter, the present invention is described in detail. The embodiments described below are intended to be presented by way of example merely to describe the invention but not limited only to the following embodiments. The present invention may be implemented in various ways without departing from the gist of the invention.

All of the publications, published patent applications, patents and other patent documents cited in the specification are herein incorporated by reference in their entirety. The specification hereby incorporates by reference the contents of the specification and drawings in the Japanese Patent Application (No. 2014-124157) filed Jun. 17, 2014, from which the priority was claimed.

1. Antisense Oligomer

The present invention provides an antisense oligomer having a length of 15 to 30 bases wherein (a) a first unit oligomer comprising a nucleotide sequence complementary to a first nucleotide sequence of 7 to 15 consecutive bases in a target exon; and (b) a second unit oligomer comprising a nucleotide sequence complementary to a second nucleotide sequence of 7 to 15 consecutive bases in the target exon are connected, wherein the first nucleotide sequence and the second nucleotide sequence are neither consecutive nor overlap with each other, and the antisense oligomer induces skipping of the target exon, or a pharmaceutically acceptable salt or hydrate thereof.

Hereinafter, "an antisense oligomer, or a pharmaceutically acceptable salt or hydrate thereof" may be generically called "an antisense oligomer" collectively.

The antisense oligomer described above can be manufactured by a method for manufacturing which comprises connecting (a) a first unit oligomer comprising a nucleotide sequence complementary to a first nucleotide sequence of 7 to 15 consecutive bases in a target exon; and (b) a second unit oligomer comprising a nucleotide sequence complementary to a second nucleotide sequence of 7 to 15 consecutive bases in the target exon to produce an antisense oligomer having a length of 15 to 30 bases, wherein the first nucleotide sequence and second nucleotide sequence are neither consecutive nor overlap with each other.

The method for manufacturing may further comprise the step of measuring the efficiency of skipping by the obtained antisense oligomer, and a secondary step of selecting an antisense oligomer having the efficiency of skipping that exceeds a reference value.

In the secondary step of the manufacturing method described above, the skipping efficiency can be determined as follows. The mRNA for the gene comprising the targeted exon is collected from test cells; in the mRNA, the polynucleotide level "A" of the band where the targeted exon is skipped and the polynucleotide level "B" of the band where the targeted exon is not skipped are measured. Using these measurement values of "A" and "B," the efficiency is calculated by the following equation:

Skipping efficiency (%)=$A/(A+B) \times 100$

Alternatively, for calculation of the efficiency of skipping, International Publication WO2012/029986 may be referred.

In the secondary step, the efficiency of skipping used as the reference value is 10% or more, 20% or more, 30% or more, 40% or more, 50% or more, 60% or more, 70% or more, 80% or more or 90% or more.

By connecting a plurality of unit oligomers as mentioned above, an antisense oligomer having improved skipping activity can be obtained even if each of the unit oligomers has low skipping activity (or no skipping activity).

The present invention also provides a method for screening of an antisense oligomer, which comprises:

(a) selecting
(i) a first unit oligomer comprising a nucleotide sequence complementary to a first nucleotide sequence of 7 to 15 consecutive bases in a target exon; and
(ii) a second unit oligomer comprising a nucleotide sequence complementary to a second nucleotide sequence of 7 to 15 consecutive bases in the target exon, wherein the first nucleotide sequence and the second nucleotide sequence are neither consecutive nor overlap with each other;
(b) connecting the first and second unit oligomers to produce an antisense oligomer having a length of 15 to 30 bases;
(c) measuring the efficiency of skipping by the antisense oligomer obtained in the step (b); and
(d) selecting an antisense oligomer having the efficiency of skipping that exceeds a reference value.

In the antisense oligomer described above, the first and second unit oligomers can be connected in a manner where either one of the first and second unit oligomers is positioned on the 5' or 3' side of the other. In an embodiment, the first unit oligomer is positioned on the 5' side, and the second unit oligomer is positioned on the 3' side for the connection.

Also, the antisense oligomer may comprise a third unit oligomer comprising a nucleotide sequence complementary to a third nucleotide sequence of 7 to 15 consecutive bases in the target exon.

As used herein, the term "connect" refers to one where the two unit oligomers are directly bound to each other or one where the two unit oligomers are bound to each other via a linker. When the two unit oligomers are directly bound to each other, then the 3' end of the unit oligomer positioned on the 5' side and the 5' end of the other unit oligomer positioned on the 3' side form a phosphate bond or a group shown below. Example of the linker include a nucleic acid (chain) of 1 to 5 residues as well as a known linker usually used for connecting nucleic acids or morpholino nucleic acid derivatives, such as 3-aminopropyl, succinyl, 2,2'-diethanolsulfonyl and long chain alkylamino (LCAA).

[Formula 2]

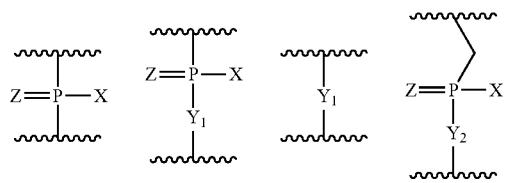

wherein X represents —OH, —$CH_2R^1$, —O—$CH_2R^1$, —S—$CH_2R^1$, —$NR^2R^3$ or F;

$R^1$ represents H or an alkyl;
$R^2$ and $R^3$, which may be the same or different, each represents H, an alkyl, a cycloalkyl or an aryl;
$Y_1$ represents O, S, $CH_2$ or $NR^1$;
$Y_2$ represents O, S or $NR^1$;
Z represents O or S.

The first and/or second unit oligomer may comprise a nucleotide sequence complementary to a partial nucleotide sequence of an intron adjacent to the target exon. In an embodiment in which, for example, the first and second unit oligomers are connected with each other in a way where the first unit oligomer is positioned on the 5' side and the second unit oligomer are positioned on the 3' side, the 5' side of the first unit oligomer may comprise a nucleotide sequence complementary to a nucleotide sequence residing in the proximity to the 3' end of an intron adjacent on the 5' side of the target exon, and/or the 3' side of the second unit oligomer may comprise a nucleotide sequence complementary to a nucleotide sequence residing in the proximity to the 5' end of an intron adjacent on the 3' side of the target exon.

The first and/or second unit oligomer may comprise a nucleotide sequence complementary to a partial nucleotide sequence of an exonic splicing enhancer (ESE) of the target exon.

The target exon is not particularly limited. In an embodiment, the target exon is an exon in a human gene and is further an exon in human dystrophin gene.

More specifically, the target exon is exon 44 in the human dystrophin gene.

Thus, in an embodiment, the present invention provides an antisense oligomer which causes skipping of exon 44 in the human dystrophin gene (hereinafter, referred to as "the oligomer of the present invention"). Hereinafter, the structure of the antisense oligomer of the present invention will be described in detail.

[Exon 44 in Human Dystrophin Gene]

In the present invention, the term "gene" is intended to mean a genomic gene and also include cDNA, mRNA precursor and mRNA. Preferably, the gene is mRNA precursor, i.e. pre-mRNA.

In the human genome, the human dystrophin gene locates at locus Xp21.2. The human dystrophin gene has a size of 3.0 Mbp and is the largest gene among known human genes. However, the coding regions of the human dystrophin gene are only 14 kb, distributed as 79 exons throughout the human dystrophin gene (Roberts, R G, et al., Genomics, 16: 536-538 (1993)). The pre-mRNA, which is the transcript of the human dystrophin gene, undergoes splicing to generate mature mRNA of 14 kb. The nucleotide sequence of human wild-type dystrophin gene is known (GenBank Accession No. NM_004006).

The nucleotide sequence of exon 44 in the human wild-type dystrophin gene is represented by SEQ ID NO; 10.

In an embodiment, the oligomer of the present invention is designed to cause skipping of exon 44 in the human dystrophin gene, thereby modifying the protein encoded by DMD type of dystrophin gene into the BMD type of dystrophin protein. Accordingly, exon 44 in the dystrophin gene that is the target of exon skipping by the antisense oligomer of the present invention includes both wild and mutant types.

Specifically, exon 44 mutants of the human dystrophin gene include the polynucleotides defined in (I) or (II) below.

(I) A polynucleotide that hybridizes under stringent conditions to a polynucleotide consisting of a nucleotide sequence complementary to the nucleotide sequence of SEQ ID NO: 10; and, (II) A polynucleotide consisting of a nucleotide sequence having at least 90% identity with the nucleotide sequence of SEQ ID NO: 10.

As used herein, the term "polynucleotide" is intended to mean DNA or RNA.

As used herein, the term "polynucleotide that hybridizes under stringent conditions" refers to, for example, a polynucleotide obtained by colony hybridization, plaque hybridization, Southern hybridization or the like, using as a probe all or part of a polynucleotide consisting of a nucleotide sequence complementary to the nucleotide sequence of, e.g., SEQ ID NO: 10. The hybridization method which may be used includes methods described in, for example, "Sambrook & Russell, Molecular Cloning: A Laboratory Manual Vol. 3, Cold Spring Harbor, Laboratory Press 2001," "Ausubel, Current Protocols in Molecular Biology, John Wiley & Sons 1987-1997," etc.

As used herein, the term "complementary nucleotide sequence" is not limited only to nucleotide sequences that form Watson-Crick pairs with target nucleotide sequences, but is intended to also include nucleotide sequences which form Wobble base pairs. As used herein, the term Watson-Crick pair refers to a pair of nucleobases in which hydrogen bonds are formed between adenine-thymine, adenine-uracil or guanine-cytosine, and the term Wobble base pair refers to a pair of nucleobases in which hydrogen bonds are formed between guanine-uracil, inosine-uracil, inosine-adenine or inosine-cytosine. As used herein, the term "complementary nucleotide sequence" does not only refers to a nucleotide sequence 100% complementary to the target nucleotide sequence but also refers to a complementary nucleotide sequence that may contain, for example, 1 to 3, 1 or 2, or one nucleotide non-complementary to the target nucleotide sequence.

As used herein, the term "stringent conditions" may be any of low stringent conditions, moderate stringent conditions or high stringent conditions. The term "low stringent conditions" are, for example, 5×SSC, 5×Denhardt's solution, 0.5% SDS, 50% formamide at 32° C. The term "moderate stringent conditions" are, for example, 5×SSC, 5×Denhardt's solution, 0.5% SDS, 50% formamide at 42° C., or 5×SSC, 1% SDS, 50 mM Tris-HCl (pH 7.5), 50% formamide at 42° C. The term "high stringent conditions" are, for example, 5×SSC, 5×Denhardt's solution, 0.5% SDS, 50% formamide at 50° C. or 0.2×SSC, 0.1% SDS at 65° C. Under these conditions, polynucleotides with higher homology are expected to be obtained efficiently at higher temperatures, although multiple factors are involved in hybridization stringency including temperature, probe concentration, probe length, ionic strength, time, salt concentration and others, and those skilled in the art may appropriately select these factors to achieve similar stringency.

When commercially available kits are used for hybridization, for example, an Alkphos Direct Labeling and Detection System (GE Healthcare) may be used. In this case, according to the attached protocol, after cultivation with a labeled probe overnight, the membrane is washed with a primary wash buffer containing 0.1% (w/v) SDS at 55° C., thereby detecting hybridized polynucleotides. Alternatively, in producing a probe based on the entire or part of the nucleotide sequence complementary to the nucleotide sequence of SEQ ID NO: 10, hybridization can be detected with a DIG Nucleic Acid Detection Kit (Roche Diagnostics) when the probe is labeled with digoxigenin (DIG) using a commercially available reagent (e.g., a PCR Labeling Mix (Roche Diagnostics), etc.).

In addition to the polynucleotides described above, other polynucleotides that can be hybridized include polynucleotides having 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity with the polynucleotide of SEQ ID NO: 10, as calculated by homology search software BLAST using the default parameters.

The identity between nucleotide sequences may be determined using algorithm BLAST (Basic Local Alignment Search Tool) by Karlin and Altschul (Proc. Natl. Acad. Sci. USA 872264-2268, 1990; Proc. Natl. Acad. Sci. USA 90: 5873, 1993). Programs called BLASTN and BLASTX based on the BLAST algorithm have been developed (Altschul S F, et al; J. Mol. Biol. 215: 403, 1990). When a nucleotide sequence is sequenced using BLASTN, the parameters are, for example, score=100 and wordlength=12. When BLAST and Gapped BLAST programs are used, the default parameters for each program are employed.

The oligomer of the present invention is specifically an antisense oligomer having a length of 15 to 30 bases wherein two unit oligomers selected from the group consisting of the following (a) and (b) are connected;

(a) a unit oligomer consisting of a nucleotide sequence complementary to a nucleotide sequence of 7 to 15 consecutive bases selected from the nucleotide sequence represented by SEQ ID NO: 1; and (b) a unit oligomer consisting of a nucleotide sequence complementary to a nucleotide sequence of 7 to 15 consecutive bases selected from the nucleotide sequence represented by SEQ ID NO: 2.

For example, the first nucleotide sequence may be a nucleotide sequence of 7 to 15 consecutive bases selected from the nucleotide sequence represented by SEQ ID NO: 1, and/or the second nucleotide sequence may be a nucleotide sequence of 7 to 15 consecutive bases selected from the nucleotide sequence represented by SEQ ID NO: 2.

Preferably, the oligomer of the present invention is an antisense oligomer having a length of 15 to 30 bases in which two unit oligomers selected from the group consisting of the following (c) to (e) are connected:

(c) a unit oligomer consisting of a sequence complementary to a nucleotide sequence of 7 to 15 consecutive bases selected from the nucleotide sequence represented by SEQ ID NO: 3;

(d) a unit oligomer consisting of a sequence complementary to a nucleotide sequence of 7 to 15 consecutive bases selected from the nucleotide sequence represented by SEQ ID NO: 4; and (e) a unit oligomer consisting of a sequence complementary to a nucleotide sequence of 7 to 15 consecutive bases selected from the nucleotide sequence represented by SEQ ID NO: 5.

Herein, the nucleotide sequences represented by SEQ ID NOs: 1 and 2 are the sequences consisting of the −1st to the 44th bases and the 58th to the 115th bases, respectively, from the 5' end of the nucleotide sequence of exon 44 (SEQ ID NO: 10) in the human wild-type dystrophin gene.

The nucleotide sequence represented by SEQ ID NO: 3 is the sequence consisting of the 18th to the 34th bases from the 5' end of the nucleotide sequence of exon 44 (SEQ ID NO: 10) in the human wild-type dystrophin gene. Similarly, the nucleotide sequences represented by SEQ ID NOs: 4 and 5 are the sequences consisting of the 61st to 77th bases and the 88th to the 104th bases, respectively.

The size of each of the unit oligomers (a) to (e) (hereinafter, also simply referred to as "the units") is a length of 7 to 15 bases and is preferably a length of 8 to 15 bases, a length of 9 to 15 bases, a length of 10 to 15 bases, a length of 10 to 14 bases, a length of 10 to 13 bases or a length of 11 to 13 bases. The units (a) to (e) may have the same size or may have different sizes.

For selecting two unit oligomers from the group consisting of (a) and (b), the two unit oligomers may be a combination of the same unit oligomers or may be a combination of different unit oligomers. Specifically, the two unit oligomers may be a combination of (a) and (a) or a combination of (b) and (b) or may be a combination of (a) and (b).

For selecting two unit oligomers from the group consisting of (c) to (e), the two unit oligomers may be a combination of the same unit oligomers or may be a combination of different unit oligomers. Preferably, the two units are respectively selected from different types. When, for example, (c) is selected as one unit, the other unit is preferably (d) or (e). Likewise, when (d) is selected as one unit, the other unit is preferably (c) or (e). Also, when (e) is selected as one unit, the other unit is preferably (c) or (d).

When the units (a) and (b) are selected, either of the selected two units may be located on the 5' side. When the units (a) and (b) are selected, the unit (a) is preferably connected on the 3' side.

When two units are selected from (c) to (e), either of the selected two units may be located on the 5' side. When the units (c) and (d) are selected, the unit (c) is preferably connected on the 3' side. When the units (d) and (e) are selected, the unit (d) is preferably connected on the 3' side. When the units (c) and (e) are selected, the unit (c) is preferably connected on the 3' side.

As used herein, the term "connect" refers to direct binding of two units selected from (a) and (b) or two units selected from (c) to (e). Specifically, the term "when two units are connected" means that the 3' end of the unit positioned on the 5' side and the 5' end of the unit positioned on the 3' side form a phosphate bond or a group shown below.

[Formula 3]

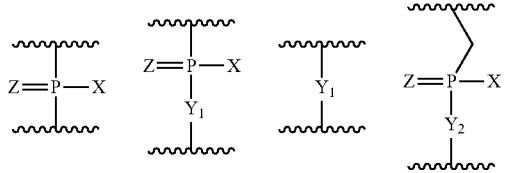

wherein X represents —OH, —CH$_2$R$^1$, —O—CH$_2$R$^1$, —S—CH$_2$R$^1$, —NR$^2$R$^3$ or F;

R$^1$ represents H or an alkyl;

R$^2$ and R$^3$, which may be the same or different, each represents H, an alkyl, a cycloalkyl or an aryl;

Y$_1$ represents O, S, CH$_2$ or NR$^1$;

Y$_2$ represents O, S or NR$^1$;

Z represents O or S.

The term "cause skipping of the exon 44 in the human dystrophin gene" is intended to mean that by binding of the oligomer of the present invention to the site corresponding to exon 44 of the transcript (e.g., pre-mRNA) of the human dystrophin gene, for example, thus resulting in formation of mature mRNA which is free of codon frame shift, the nucleotide sequence corresponding to the 5' end of exon 46 is spliced at the nucleotide sequence corresponding to the 3' end of exon 43 in DMD patients with deletion of exon 45 when the transcript undergoes splicing.

Herein, the term "binding" described above is intended to mean that when the oligomer of the present invention is mixed with the transcript of human dystrophin gene, both are hybridized under physiological conditions to form a double strand nucleic acid. The term "under physiological conditions" refers to conditions set to mimic the in vivo environment in terms of pH, salt composition and temperature. The conditions are, for example, 25 to 40° C., preferably 37° C., pH 5 to 8, preferably pH 7.4 and 150 mM of sodium chloride concentration.

Whether the skipping of exon 44 in the human dystrophin gene is caused or not can be confirmed by introducing the oligomer of the present invention into a dystrophin expression cell (e.g., human rhabdomyosarcoma cells), amplifying the region surrounding exon 44 of mRNA of the human dystrophin gene from the total RNA of the dystrophin expression cell by RT-PCR and performing nested PCR or sequence analysis on the PCR amplified product.

The skipping efficiency can be determined as follows. The mRNA for the human dystrophin gene is collected from test cells; in the mRNA, the polynucleotide level "A" of the band where exon 44 is skipped and the polynucleotide level "B" of the band where exon 44 is not skipped are measured. Using these measurement values of "A" and "B," the efficiency is calculated by the following equation:

Skipping efficiency (%)=$A/(A+B)\times 100$

Alternatively, for calculation of the efficiency of skipping, International Publication WO2012/029986 may be referred.

Preferably, the antisense oligomer of the present invention cause skipping of the targeted exon (e.g., exon 44) with the efficiency of 10% or higher, 20% or higher, 30% or higher, 40% or higher, 50% or higher, 60% or higher, 70% or higher, 80% or higher, or 90% or higher.

The antisense oligomer of the present invention includes, for example, an oligonucleotide, morpholino oligomer or peptide nucleic acid (PNA) oligomer, having a length of 15 to 30 bases. The length is preferably from 16 to 30, from 17 to 30, from 18 to 30, from 19 to 30, from 20 to 30, from 20 to 29, from 20 to 28, from 20 to 27, from 20 to 26, from 21 to 26, or from 22 to 26 bases and morpholino oligomers are preferred.

The oligonucleotide described above (hereinafter referred to as "the oligonucleotide of the present invention") is the oligomer of the present invention composed of nucleotides as constituent units. Such nucleotides may be any of ribonucleotides, deoxyribonucleotides and modified nucleotides.

The modified nucleotide refers to one having fully or partly modified nucleobases, sugar moieties and/or phosphate-binding regions, which constitute the ribonucleotide or deoxyribonucleotide.

The nucleobase includes, for example, adenine, guanine, hypoxanthine, cytosine, thymine, uracil, and modified bases thereof. Examples of such modified bases include, but not limited to, pseudouracil, 3-methyluracil, dihydrouracil, 5-alkylcytosines (e.g., 5-methylcytosine), 5-alkyluracils (e.g., 5-ethyluracil), 5-halouracils (5-bromouracil), 6-azapyrimidine, 6-alkylpyrimidines (6-methyluracil), 2-thiouracil, 4-thiouracil, 4-acetylcytosine, 5-(carboxyhydroxymethyl) uracil, 5-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, N6-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-N6-isopentenyladenine, uracil-5-oxyacetic acid, 2-thiocytosine, purine, 2,6-diaminopurine, 2-aminopurine, isoguanine, indole, imidazole, xanthine, etc.

Modification of the sugar moiety may include, for example, modifications at the 2'-position of ribose and modifications of the other positions of the sugar. The modification at the 2'-position of ribose includes replacement of the 2'-OH of ribose with OR, R, R'OR, SH, SR, NH$_2$, NHR, NR$_2$, N$_3$, CN, F, Cl, Br or I, wherein R represents an alkyl or an aryl and R' represents an alkylene.

The modification for the other positions of the sugar includes, for example, replacement of O at the 4' position of ribose or deoxyribose with S, bridging between 2' and 4' positions of the sugar, e.g., LNA (Locked Nucleic Acid) or ENA (2'-O,4'-C-Ethylene-bridged Nucleic Acids), but is not limited thereto.

A modification of the phosphate-binding region includes, for example, a modification of replacing phosphodiester bond with phosphorothioate bond, phosphorodithioate bond, alkyl phosphonate bond, phosphoroamidate bond or boranophosphate bond (Enya et al: Bioorganic & Medicinal Chemistry, 2008, 18, 9154-9160) (cf., e.g., Japan Domestic Re-Publications of PCT Application Nos. 2006/129594 and 2006/038608).

The alkyl is preferably a straight or branched alkyl having 1 to 6 carbon atoms. Specific examples include methyl, ethyl, n-propyl, isopropyl, n-butyl, isobutyl, sec-butyl, tert-butyl, n-pentyl, isopentyl, neopentyl, tert-pentyl, n-hexyl and isohexyl. The alkyl may optionally be substituted. Examples of such substituents are a halogen, an alkoxy, cyano and nitro. The alkyl may be substituted with one to three of such substituents.

The cycloalkyl is preferably a cycloalkyl having 5 to 12 carbon atoms. Specific examples include cyclopentyl, cyclohexyl, cycloheptyl, cyclooctyl, cyclodecyl and cyclododecyl.

The halogen includes fluorine, chlorine, bromine and iodine.

The alkoxy is a straight or branched alkoxy having 1 to 6 carbon atoms such as methoxy, ethoxy, n-propoxy, isopropoxy, n-butoxy, isobutoxy, sec-butoxy, tert-butoxy, n-pentyloxy, isopentyloxy, n-hexyloxy, isohexyloxy, etc. Among others, an alkoxy having 1 to 3 carbon atoms is preferred.

The aryl is preferably an aryl having 6 to 10 carbon atoms. Specific examples include phenyl, α-naphthyl and 6-naphthyl. Among others, phenyl is preferred. The aryl may optionally be substituted. Examples of such substituents are an alkyl, a halogen, an alkoxy, cyano and nitro. The aryl may be substituted with one to three of such substituents.

In this invention, the alkylene is preferably a straight or branched alkylene having 1 to 6 carbon atoms. Specific examples include methylene, ethylene, trimethylene, tetramethylene, pentamethylene, hexamethylene, 2-(ethyl) trimethylene and 1-(methyl) tetramethylene.

The acyl includes a straight or branched alkanoyl or aroyl. Examples of the alkanoyl include formyl, acetyl, 2-methylacetyl, 2,2-dimethylacetyl, propionyl, butyryl, isobutyryl, pentanoyl, 2,2-dimethylpropionyl, hexanoyl, etc. Examples of the aroyl include benzoyl, toluoyl and naphthoyl. The aroyl may optionally be substituted at substitutable positions and may be substituted with an alkyl(s).

Preferably, the oligonucleotide of the present invention is the oligomer of the present invention containing a constituent unit represented by general formula below wherein the —OH group at position 2' of ribose is substituted with methoxy and the phosphate-binding region is a phosphorothioate bond:

[Formula 4]

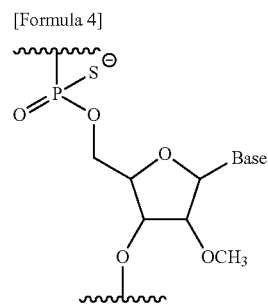

wherein Base represents a nucleobase.

The oligonucleotide of the present invention may be easily synthesized using various automated synthesizer (e.g., AKTA oligopilot plus 10/100 (GE Healthcare)). Alternatively, the synthesis may also be entrusted to a third-party organization (e.g., Promega Inc. or Takara Co.), etc.

The morpholino oligomer described above is the oligomer of the present invention comprising the constituent unit represented by general formula below:

[Formula 5]

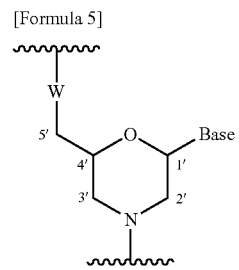

wherein Base has the same significance as defined above, and,

W represents a group shown by any one of the following groups:

[Formula 6]

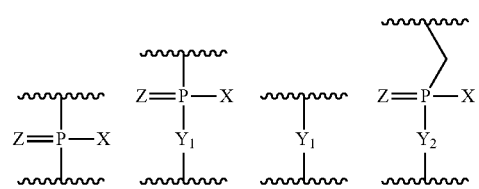

wherein X represents —CH$_2$R$^1$, —O—CH$_2$R$^1$, —S—CH$_2$R$^1$, —NR$^2$R$^3$ or F;

R$^1$ represents H or an alkyl;

R$^2$ and R$^3$, which may be the same or different, each represents H, an alkyl, a cycloalkyl or an aryl;

Y$_1$ represents O, S, CH$_2$ or NR$^1$;

Y$_2$ represents O, S or NR$^1$;

Z represents O or S.

Preferably, the morpholino oligomer is an oligomer comprising a constituent unit represented by general formula below (phosphorodiamidate morpholino oligomer (hereinafter referred to as "PMO")).

[Formula 7]

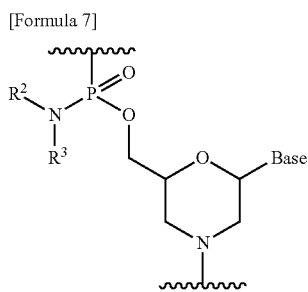

wherein Base, $R^2$ and $R^3$ have the same significance as defined above.

The morpholino oligomer may be produced in accordance with, e.g., WO 1991/009033 or WO 2009/064471. In particular, PMO can be produced by the procedure described in WO 2009/064471 or WO2013/100190.

[Method for Producing PMO]

An embodiment of PMO is, for example, the compound represented by general formula (I) below (hereinafter PMO (I)).

[Formula 8]

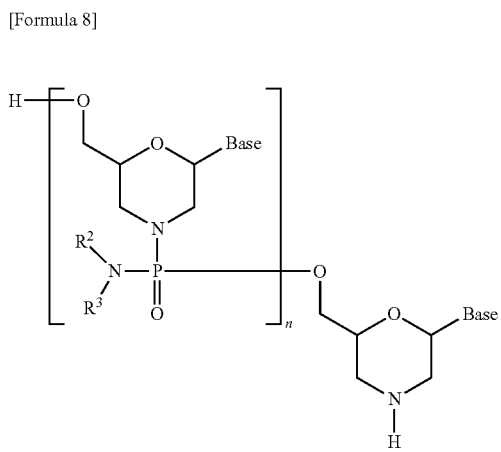

(I)

wherein Base, $R^2$ and $R^3$ have the same significance as defined above; and, n is a given integer of 1 to 99, preferably a given integer of 18 to 28.

PMO (I) can be produced in accordance with a known method, for example, can be produced by performing the procedures in the following steps.

The compounds and reagents used in the steps below are not particularly limited so long as they are commonly used to prepare PMO.

Also, the following steps can all be carried out by the liquid phase method or the solid phase method (using manuals or commercially available solid phase automated synthesizers). In producing PMO by the solid phase method, it is desired to use automated synthesizers in view of simple operation procedures and accurate synthesis.

(1) Step A:

The compound represented by general formula (II) below (hereinafter referred to as Compound (II)) is reacted with an acid to prepare the compound represented by general formula (III) below (hereinafter referred to as Compound (III)):

[Formula 9]

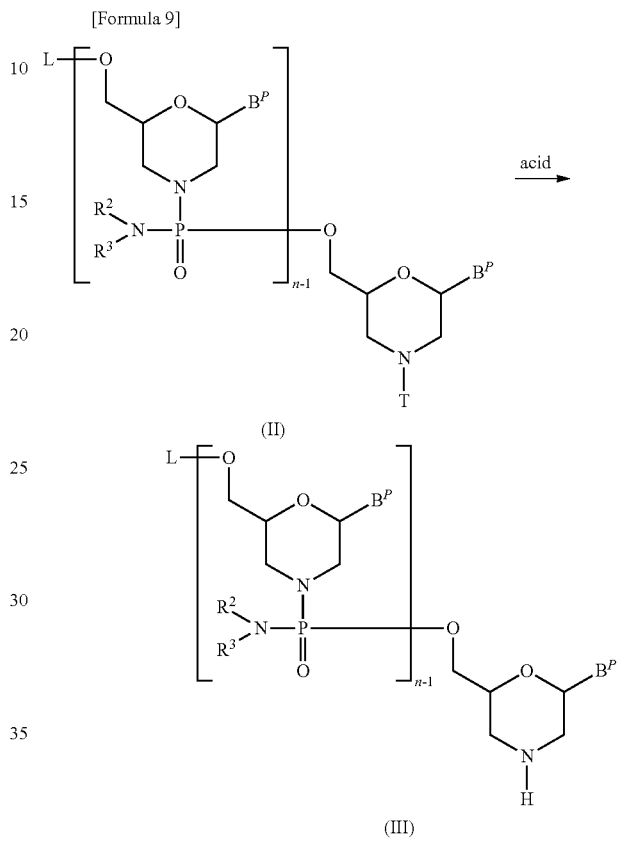

wherein n, $R^2$ and $R^3$ have the same significance as defined above;

each $B^P$ independently represents a nucleobase which may optionally be protected;

T represents trityl, monomethoxytrityl or dimethoxytrityl; and,

L represents hydrogen, an acyl or a group represented by general formula (IV) below (hereinafter referred to as group (IV)).

[Formula 10]

(IV)

The "nucleobase" for $B^P$ includes the same "nucleobase" as in Base, provided that the amino or hydroxy group in the nucleobase shown by $B^P$ may be protected.

Such protective group for amino is not particularly limited so long as it is used as a protective group for nucleic acids. Specific examples include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene. Specific examples of the protective group for the hydroxy group include 2-cyanoethyl, 4-nitrophenethyl, phenylsulfonylethyl, methylsulfonylethyl and trimethylsilylethyl, and phenyl, which may be substituted by 1 to 5 electron-withdrawing group at optional substitutable positions, diphenylcarbamoyl, dimethylcarbamoyl, diethylcarbamoyl, methylphenylcarbamoyl, 1-pyrolidinylcarbamoyl, morpholinocarbamoyl, 4-(tert-butylcarboxy) benzyl, 4-[(dimethylamino)carboxy]benzyl and 4-(phenylcarboxy)benzyl, (cf., e.g., WO 2009/064471).

The "solid carrier" is not particularly limited so long as it is a carrier usable for the solid phase reaction of nucleic acids. It is desired for the solid carrier to have the following properties: e.g., (i) it is sparingly soluble in reagents that can be used for the synthesis of morpholino nucleic acid derivatives (e.g., dichloromethane, acetonitrile, tetrazole, N-methylimidazole, pyridine, acetic anhydride, lutidine, trifluoroacetic acid); (ii) it is chemically stable to the reagents usable for the synthesis of morpholino nucleic acid derivatives; (iii) it can be chemically modified; (iv) it can be charged with desired morpholino nucleic acid derivatives; (v) it has a strength sufficient to withstand high pressure through treatments; and (vi) it has a uniform particle diameter range and distribution. Specifically, swellable polystyrene (e.g., aminomethyl polystyrene resin 1% dibenzylbenzene crosslinked (200-400 mesh) (2.4-3.0 mmol/g) (manufactured by Tokyo Chemical Industry), Aminomethylated Polystyrene Resin HCl [dibenzylbenzene 1%, 100-200 mesh] (manufactured by Peptide Institute, Inc.)), non-swellable polystyrene (e.g., Primer Support (manufactured by GE Healthcare)), PEG chain-attached polystyrene (e.g., NH$_2$-PEG resin (manufactured by Watanabe Chemical Co.), TentaGel resin), controlled pore glass (controlled pore glass; CPG) (manufactured by, e.g., CPG), oxalyl-controlled pore glass (cf., e.g., Alul et al., Nucleic Acids Research, Vol. 19, 1527 (1991)), TentaGel support-aminopolyethylene glycol-derivatized support (e.g., Wright et al., cf., Tetrahedron Letters, Vol. 34, 3373 (1993)), and a copolymer of Poros-polystyrene/divinylbenzene.

A "linker" which can be used is a known linker generally used to connect nucleic acids or morpholino nucleic acid derivatives. Examples include 3-aminopropyl, succinyl, 2,2'-diethanolsulfonyl and a long chain alkyl amino (LCAA).

This step can be performed by reacting Compound (II) with an acid.

The "acid" which can be used in this step includes, for example, trifluoroacetic acid, dichloroacetic acid and trichloroacetic acid. The acid used is appropriately in a range of, for example, 0.1 mol equivalent to 1000 mol equivalents based on 1 mol of Compound (II), preferably in a range of 1 mol equivalent to 100 mol equivalents based on 1 mol of Compound (II).

An organic amine can be used in combination with the acid described above. The organic amine is not particularly limited and includes, for example, triethylamine. The amount of the organic amine used is appropriately in a range of, e.g., 0.01 mol equivalent to 10 mol equivalents, and preferably in a range of 0.1 mol equivalent to 2 mol equivalents, based on 1 mol of the acid.

When a salt or mixture of the acid and the organic amine is used in this step, the salt or mixture includes, for example, a salt or mixture of trifluoroacetic acid and triethylamine, and more specifically, a mixture of 1 equivalent of triethylamine and 2 equivalents of trifluoroacetic acid.

The acid which can be used in this step may also be used in the form of a dilution with an appropriate solvent in a concentration of 0.1% to 30%. The solvent is not particularly limited as far as it is inert to the reaction, and includes, for example, dichloromethane, acetonitrile, an alcohol (ethanol, isopropanol, trifluoroethanol, etc.), water, or a mixture thereof.

The reaction temperature in the reaction described above is preferably in a range of, e.g., 10° C. to 50° C., more preferably, in a range of 20° C. to 40° C., and most preferably, in a range of 25° C. to 35° C.

The reaction time may vary depending upon kind of the acid used and reaction temperature, and is appropriately in a range of 0.1 minute to 24 hours in general, and preferably in a range of 1 minute to 5 hours.

After completion of this step, a base may be added, if necessary, to neutralize the acid remained in the system. The "base" is not particularly limited and includes, for example, diisopropylamine. The base may also be used in the form of a dilution with an appropriate solvent in a concentration of 0.1% (v/v) to 30% (v/v).

The solvent used in this step is not particularly limited so long as it is inert to the reaction, and includes dichloromethane, acetonitrile, an alcohol (ethanol, isopropanol, trifluoroethanol, etc.), water, and a mixture thereof. The reaction temperature is preferably in a range of, e.g., 10° C. to 50° C., more preferably, in a range of 20° C. to 40° C., and most preferably, in a range of 25° C. to 35° C.

The reaction time may vary depending upon kind of the base used and reaction temperature, and is appropriately in a range of 0.1 minute to 24 hours in general, and preferably in a range of 1 minute to 5 hours.

In Compound (II), the compound of general formula (IIa) below (hereinafter Compound (IIa)), wherein n is 1 and L is a group (IV), can be produced by the following procedure.

[Formula 11]

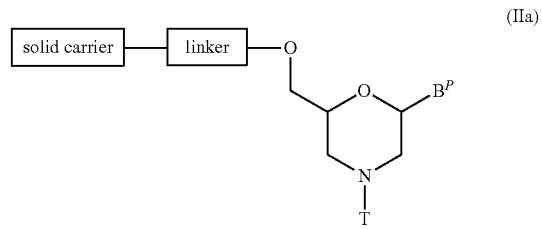

(IIa)

wherein B$^P$, T, linker and solid carrier have the same significance as defined above.

Step 1:

The compound represented by general formula (V) below is reacted with an acylating agent to prepare the compound represented by general formula (VI) below (hereinafter referred to as Compound (VI)).

[Formula 12]

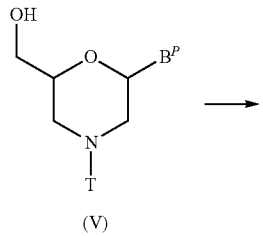

(V)

-continued

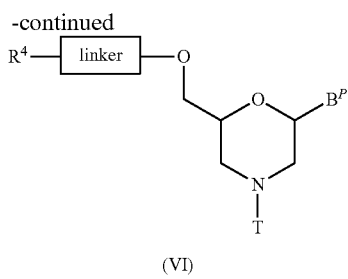

(VI)

wherein $B^P$, T and linker have the same significance as defined above; and, $R^4$ represents hydroxy, a halogen, carboxyl group or amino.

This step can be carried out by known procedures for introducing linkers, using Compound (V) as the starting material.

In particular, the compound represented by general formula (VIa) below can be produced by performing the method known as esterification, using Compound (V) and succinic anhydride.

[Formula 13]

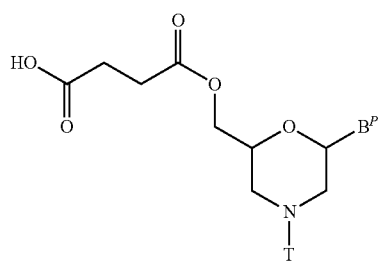

(VIa)

wherein $B^P$ and T have the same significance as defined above.

Step 2:

Compound (VI) is reacted with a solid career by a condensing agent to prepare Compound (IIa).

[Formula 14]

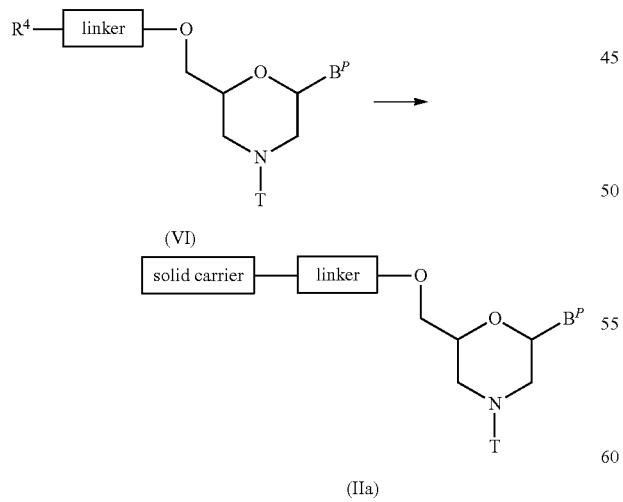

wherein $B^P$, $R^4$, T, linker and solid carrier have the same significance as defined above.

This step can be performed using Compound (VI) and a solid carrier in accordance with a process known as condensation reaction.

In Compound (II), the compound represented by general formula (IIa2) below wherein n is 2 to 99 and L is a group represented by general formula (IV) can be produced by using Compound (IIa) as the starting material and repeating step A and step B of the PMO production method described in the specification for a desired number of times.

[Formula 15]

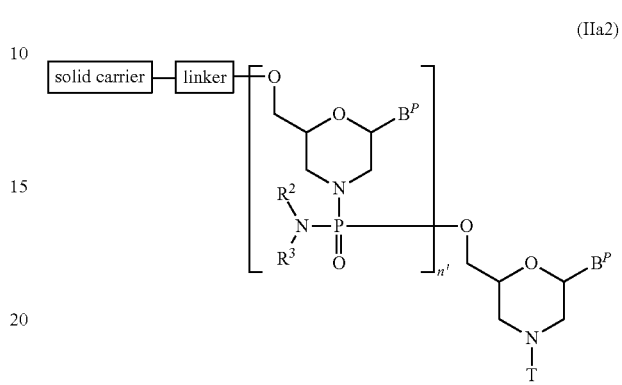

(IIa2)

wherein $B^P$, $R^2$, $R^3$, T, linker and solid carrier have the same significance as defined above; and,
n' represents 1 to 98.

In Compound (II), the compound of general formula (IIb) below wherein n is 1 and L is hydrogen can be produced by the procedure described in, e.g., WO 1991/009033.

[Formula 16]

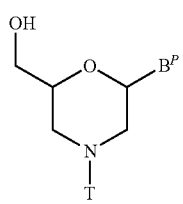

(IIb)

wherein $B^P$ and T have the same significance as defined above.

In Compound (II), the compound represented by general formula (IIb2) below wherein n is 2 to 99 and L is hydrogen can be produced by using Compound (IIb) as the starting material and repeating step A and step B of the PMO production method described in the specification for a desired number of times.

[Formula 17]

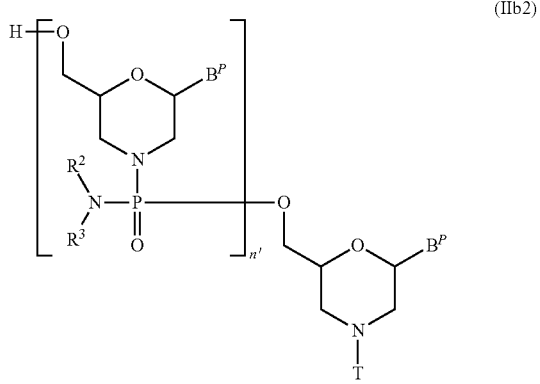

(IIb2)

wherein $B^P$, n', $R^2$, $R^3$ and T have the same significance as defined above.

In Compound (II), the compound represented by general formula (IIc) below wherein n is 1 and L is an acyl can be produced by performing the procedure known as acylation reaction, using Compound (IIb).

[Formula 18]

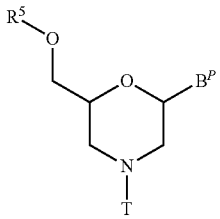

(IIc)

wherein $B^P$ and T have the same significance as defined above; and,
$R^5$ represents an acyl.

In Compound (II), the compound represented by general formula (IIc2) below wherein n is 2 to 99 and L is an acyl can be produced by using Compound (IIc) as the starting material and repeating step A and step B of the PMO production method described in the specification for a desired number of times.

[Formula 19]

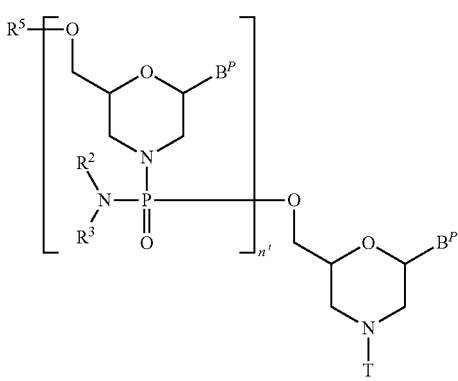

(IIc2)

wherein $B^P$, n', $R^2$, $R^3$, $R^3$ and T have the same significance as defined above.

(2) Step B

Compound (III) is reacted with a morpholino monomer compound in the presence of a base to prepare the compound represented by general formula (VII) below (hereinafter referred to as Compound (VII)):

[Formula 20]

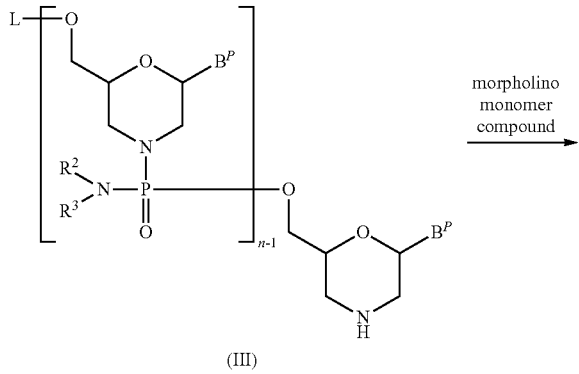

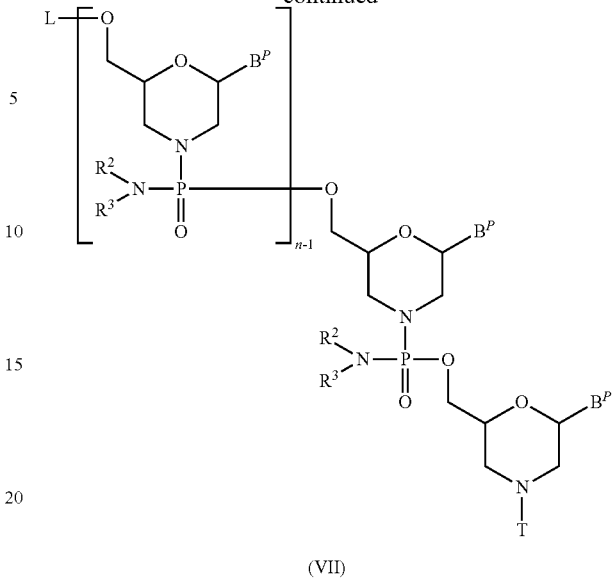

(VII)

wherein $B^P$, L, n, $R^2$, $R^3$ and T have the same significance as defined above.

This step can be performed by reacting Compound (III) with a morpholino monomer compound in the presence of a base.

The morpholino monomer compound includes, for example, compounds represented by general formula (VIII) below:

[Formula 21]

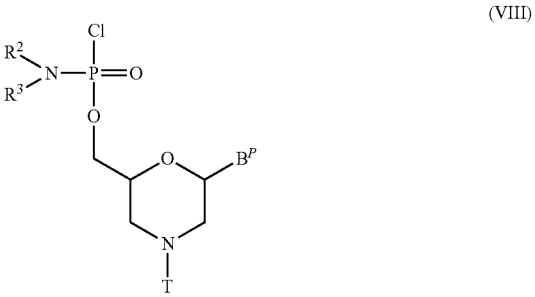

(VIII)

wherein $B^P$, $R^2$, $R^3$ and T have the same significance as defined above.

The "base" which can be used in this step includes, for example, diisopropylamine, triethylamine and N-ethylmorpholine. The amount of the base used is appropriately in a range of 1 mol equivalent to 1000 mol equivalents based on 1 mol of Compound (III), preferably, 10 mol equivalents to 100 mol equivalents based on 1 mol of Compound (III).

The morpholino monomer compound and base which can be used in this step may also be used as a dilution with an appropriate solvent in a concentration of 0.1% to 30%. The solvent is not particularly limited as far as it is inert to the reaction, and includes, for example, N,N-dimethylimidazolidone, N-methylpiperidone, DMF, dichloromethane, acetonitrile, tetrahydrofuran, or a mixture thereof.

The reaction temperature is preferably in a range of, e.g., 0° C. to 100° C., and more preferably, in a range of 10° C. to 50° C.

The reaction time may vary depending upon kind of the base used and reaction temperature, and is appropriately in a range of 1 minute to 48 hours in general, and preferably in a range of 30 minutes to 24 hours.

Furthermore, after completion of this step, an acylating agent can be added, if necessary. The "acylating agent" includes, for example, acetic anhydride, acetyl chloride and phenoxyacetic anhydride. The acylating agent may also be used as a dilution with an appropriate solvent in a concentration of 0.1% to 30%. The solvent is not particularly limited as far as it is inert to the reaction, and includes, for example, dichloromethane, acetonitrile, an alcohol(s) (ethanol, isopropanol, trifluoroethanol, etc.), water, or a mixture thereof.

If necessary, a base such as pyridine, lutidine, collidine, triethylamine, diisopropylethylamine, N-ethylmorpholine, etc. may also be used in combination with the acylating agent. The amount of the acylating agent is appropriately in a range of 0.1 mol equivalent to 10000 mol equivalents, and preferably in a range of 1 mol equivalent to 1000 mol equivalents. The amount of the base is appropriately in a range of, e.g., 0.1 mol equivalent to 100 mol equivalents, and preferably in a range of 1 mol equivalent to 10 mol equivalents, based on 1 mol of the acylating agent.

The reaction temperature in this reaction is preferably in a range of 10° C. to 50° C., more preferably, in a range of 10° C. to 50° C., much more preferably, in a range of 20° C. to 40° C., and most preferably, in a range of 25° C. to 35° C. The reaction time may vary depending upon kind of the acylating agent used and reaction temperature, and is appropriately in a range of 0.1 minute to 24 hours in general, and preferably in a range of 1 minute to 5 hours.

(3) Step C:

In Compound (VII) produced in Step B, the protective group is removed using a deprotecting agent to prepare the compound represented by general formula (IX).

[Formula 22]

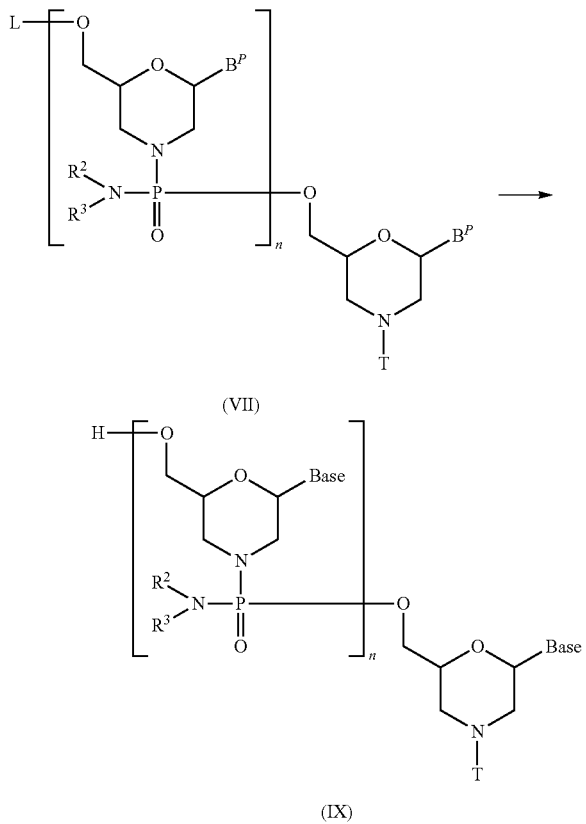

(VII)

(IX)

wherein Base, $B^P$, L, n, $R^2$, $R^3$ and T have the same significance as defined above.

This step can be performed by reacting Compound (VII) with a deprotecting agent.

The "deprotecting agent" includes, e.g., conc. ammonia water and methylamine. The "deprotecting agent" used in this step may also be used as a dilution with, e.g., water, methanol, ethanol, isopropyl alcohol, acetonitrile, tetrahydrofuran, DMF, N,N-dimethylimidazolidone, N-methylpiperidone, or a mixture of these solvents. Among them, ethanol is preferred. The amount of the deprotecting agent used is appropriately in a range of, 1 mol equivalent to 100000 mol equivalents, and preferably in a range of 10 mol equivalents to 1000 mol equivalents, based on 1 mol of Compound (VII).

The reaction temperature is appropriately in a range of 15° C. to 75° C., preferably, in a range of 40° C. to 70° C., and more preferably, in a range of 50° C. to 60° C. The reaction time for deprotection may vary depending upon kind of Compound (VII), reaction temperature, etc., and is appropriately in a range of 10 minutes to 30 hours, preferably 30 minutes to 24 hours, and more preferably in a range of 5 hours to 20 hours.

(4) Step D:

PMO (I) is produced by reacting Compound (IX) produced in step C with an acid:

[Formula 23]

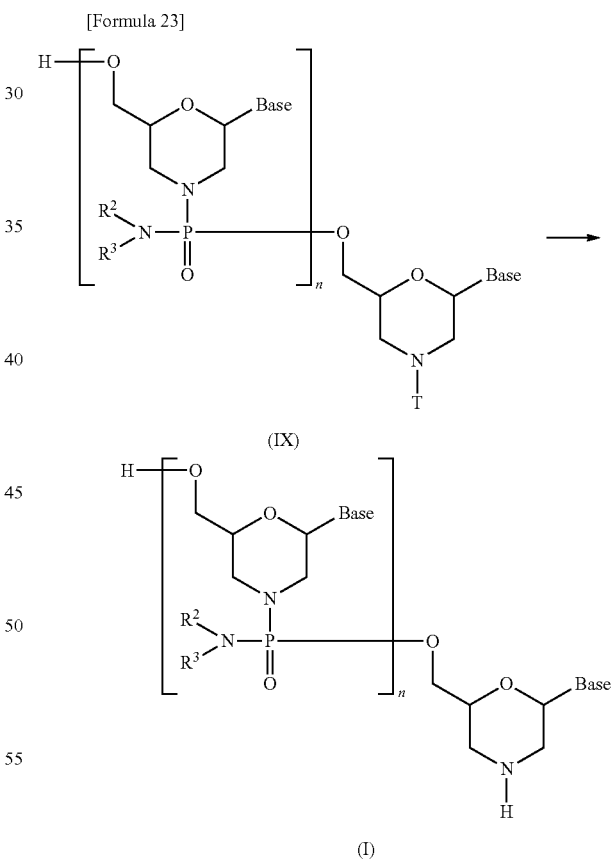

(IX)

(I)

wherein Base, n, $R^2$, $R^3$ and T have the same significance as defined above.

This step can be performed by adding an acid to Compound (IX).

The "acid" which can be used in this step includes, for example, trichloroacetic acid, dichloroacetic acid, acetic acid, phosphoric acid, hydrochloric acid, etc. The acid used is appropriately used to allow the solution to have a pH range of 0.1 to 4.0, and more preferably, in a range of pH 1.0 to 3.0. The solvent is not particularly limited so long as it is inert to the reaction, and includes, for example, acetonitrile, water, or a mixture of these solvents thereof.

The reaction temperature is appropriately in a range of 10° C. to 50° C., preferably, in a range of 20° C. to 40° C., and more preferably, in a range of 25° C. to 35° C. The reaction time for deprotection may vary depending upon kind of Compound (IX), reaction temperature, etc., and is appropriately in a range of 0.1 minute to 5 hours, preferably 1 minute to 1 hour, and more preferably in a range of 1 minute to 30 minutes.

PMO (I) can be obtained by subjecting the reaction mixture obtained in this step to conventional means of separation and purification such as extraction, concentration, neutralization, filtration, centrifugal separation, recrystallization, reversed phase column chromatography $C_8$ to $C_{18}$, cation exchange column chromatography, anion exchange column chromatography, gel filtration column chromatography, high performance liquid chromatography, dialysis, ultrafiltration, etc., alone or in combination thereof. Thus, the desired PMO (I) can be isolated and purified (cf., e.g., WO 1991/09033).

In purification of PMO (I) using reversed phase chromatography, e.g., a solution mixture of 20 mM triethylamine/acetate buffer and acetonitrile can be used as an elution solvent.

In purification of PMO (I) using ion exchange chromatography, e.g., a solution mixture of 1 M saline solution and 10 mM sodium hydroxide aqueous solution can be used as an elution solvent.

The peptide nucleic acid described above is the oligomer of the present invention having a group represented by the following general formula as the constituent unit:

[Formula 24]

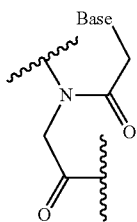

wherein Base has the same significance as defined above.

Peptide nucleic acids can be prepared by referring to, e.g., the following literatures.
1) P. E. Nielsen, M. Egholm, R. H. Berg, O. Buchardt, Science, 254, 1497 (1991)
2) M. Egholm, O. Buchardt, P. E. Nielsen, R. H. Berg, Jacs., 114, 1895 (1992)
3) K. L. Dueholm, M. Egholm, C. Behrens, L. Christensen, H. F. Hansen, T. Vulpius, K. H. Petersen, R. H. Berg, P. E. Nielsen, O. Buchardt, J. Org. Chem., 59, 5767 (1994)
4) L. Christensen, R. Fitzpatrick, B. Gildea, K. H. Petersen, H. F. Hansen, T. Koch, M. Egholm, O. Buchardt, P. E. Nielsen, J. Coull, R. H. Berg, J. Pept. Sci., 1, 175 (1995)
5) T. Koch, H. F. Hansen, P. Andersen, T. Larsen, H. G. Batz, K. Otteson, H. Orum, J. Pept. Res., 49, 80 (1997)

In the oligomer of the present invention, the 5' end may be any of chemical structures (1) to (3) below, and preferably is (3)-OH.

[Formula 25]

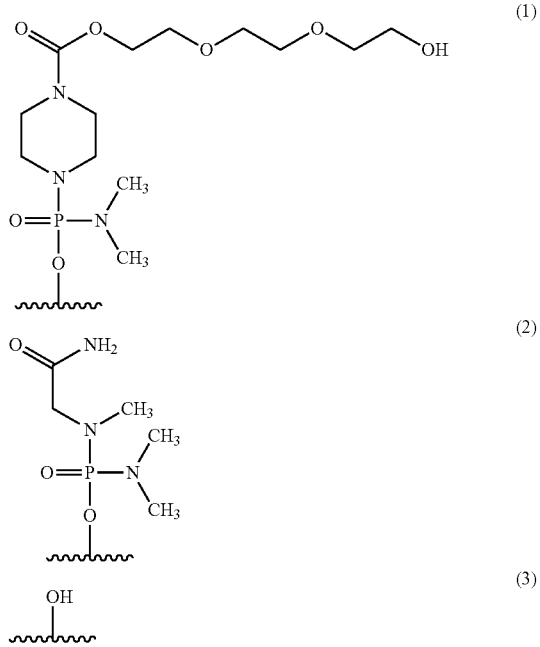

Hereinafter, the groups shown by (1), (2) and (3) above are referred to as "Group (1)," "Group (2)" and "Group (3)," respectively.

2. Pharmaceutical Composition

The oligomer of the present invention causes skipping of exon 44 in the dystrophin gene. It is thus expected that conditions of muscular dystrophy can be relieved by administering the pharmaceutical composition comprising the oligomer of the present invention to DMD patients, who has target mutation of exon 44 skipping, that is mutation converting to in-frame by Exon 44 skipping. Also, the manufacturing process of the oligomer of the present invention, whose chain length is short, is simple and the manufacturing cost of the oligomer of the present invention can be reduced.

In another embodiment, the present invention provides the pharmaceutical composition for the treatment of muscular dystrophy, comprising as an active ingredient the oligomer of the present invention, a pharmaceutically acceptable salt or hydrate thereof (hereinafter referred to as "the composition of the present invention")

Examples of the pharmaceutically acceptable salt of the oligomer of the present invention contained in the composition of the present invention are alkali metal salts such as salts of sodium, potassium and lithium; alkaline earth metal salts such as salts of calcium and magnesium; metal salts such as salts of aluminum, iron, zinc, copper, nickel, cobalt, etc.; ammonium salts; organic amine salts such as salts of t-octylamine, dibenzylamine, morpholine, glucosamine, phenylglycine alkyl ester, ethylenediamine, N-methylglucamine, guanidine, diethylamine, triethylamine, dicyclohexylamine, N, N'-dibenzylethylenediamine, chloroprocaine, procaine, diethanolamine, N-benzylphenethylamine, piperazine, tetramethylammonium, tris(hydroxymethyl)aminomethane; hydrohalide salts such as salts of hydrofluorates, hydrochlorides, hydrobromides and hydroiodides; inorganic acid salts such as nitrates, perchlorates, sulfates, phosphates, etc.; lower alkane sulfonates such as methanesulfonates, trifluoromethanesulfonates and ethanesulfonates; arylsulfonates such as benzenesulfonates and p-toluenesulfonates; organic acid salts such as acetates, malates, fumarates, succinates, citrates, tartarates, oxalates, maleates, etc.; and, amino acid salts such as salts of glycine, lysine, arginine, ornithine, glutamic acid and aspartic acid. These salts may be produced by known methods. Alternatively, the oligomer of the present invention contained in the composition of the present invention may be in the form of a hydrate thereof.

Administration route for the composition of the present invention is not particularly limited so long as it is pharmaceutically acceptable route for administration, and can be chosen depending upon method of treatment. In view of easiness in delivery to muscle tissues, preferred are intravenous administration, intraarterial administration, intramuscular administration, subcutaneous administration, oral administration, tissue administration, transdermal administration, etc. Also, dosage forms which are available for the composition of the present invention are not particularly limited, and include, for example, various injections, oral agents, drips, inhalations, ointments, lotions, etc.

In administration of the oligomer of the present invention to patients with muscular dystrophy, the composition of the present invention preferably contains a carrier to promote delivery of the oligomer to muscle tissues. Such a carrier is not particularly limited as far as it is pharmaceutically acceptable, and examples include cationic carriers such as cationic liposomes, cationic polymers, etc., or carriers using viral envelope. The cationic liposomes are, for example, liposomes composed of 2-O-(2-diethylaminoethyl)carabamoyl-1,3-O-dioleoylglycerol and phospholipids as the essential constituents (hereinafter referred to as "liposome A"), Oligofectamine (registered trademark) (manufactured by Invitrogen Corp.), Lipofectin (registered trademark) (manufactured by Invitrogen Corp.), Lipofectamine (registered trademark) (manufactured by Invitrogen Corp.), Lipofectamine 2000 (registered trademark) (manufactured by Invitrogen Corp.), DMRIE-C (registered trademark) (manufactured by Invitrogen Corp.), GeneSilencer (registered trademark) (manufactured by Gene Therapy Systems), TransMessenger (registered trademark) (manufactured by QIAGEN, Inc.), TransIT TKO (registered trademark) (manufactured by Mirus) and Nucleofector II (Lonza). Among others, liposome A is preferred. Examples of cationic polymers are JetSI (registered trademark) (manufactured by Qbiogene, Inc.) and Jet-PEI (registered trademark) (polyethylenimine, manufactured by Qbiogene, Inc.). An example of carriers using viral envelop is GenomeOne (registered trademark) (HVJ-E liposome, manufactured by Ishihara Sangyo). Alternatively, the medical devices described in Japanese Patent No. 2924179 and the cationic carriers described in Japanese Domestic Re-Publication PCT Nos. 2006/129594 and 2008/096690 may be used as well.

A concentration of the oligomer of the present invention contained in the composition of the present invention may vary depending on kind of the carrier, etc., and is appropriately in a range of 0.1 nM to 100 µM, preferably in a range of 1 nM to 10 µM, and more preferably in a range of 10 nM to 1 µM. A weight ratio of the oligomer of the present invention contained in the composition of the present invention and the carrier (carrier/oligomer of the present invention) may vary depending on property of the oligomer, type of the carrier, etc., and is appropriately in a range of 0.1 to 100, preferably in a range of 1 to 50, and more preferably in a range of 10 to 20.

In addition to the oligomer of the present invention and the carrier described above, pharmaceutically acceptable additives may also be optionally formulated in the composition of the present invention. Examples of such additives are emulsification aids (e.g., fatty acids having 6 to 22 carbon atoms and their pharmaceutically acceptable salts, albumin and dextran), stabilizers (e.g., cholesterol and phosphatidic acid), isotonizing agents (e.g., sodium chloride, glucose, maltose, lactose, sucrose, trehalose), and pH controlling agents (e.g., hydrochloric acid, sulfuric acid, phosphoric acid, acetic acid, sodium hydroxide, potassium hydroxide and triethanolamine). One or more of these additives can be used. The content of the additive in the composition of the present invention is appropriately 90 wt % or less, preferably 70 wt % or less and more preferably, 50 wt % or less.

The composition of the present invention can be prepared by adding the oligomer of the present invention to a carrier dispersion and adequately stirring the mixture. Additives may be added at an appropriate step either before or after addition of the oligomer of the present invention. An aqueous solvent that can be used in adding the oligomer of the present invention is not particularly limited as far as it is pharmaceutically acceptable, and examples are injectable water or injectable distilled water, electrolyte fluid such as physiological saline, etc., and sugar fluid such as glucose fluid, maltose fluid, etc. A person skilled in the art can appropriately choose conditions for pH and temperature for such matter.

The composition of the present invention may be prepared into, e.g., a liquid form and its lyophilized preparation. The lyophilized preparation can be prepared by lyophilizing the composition of the present invention in a liquid form in a conventional manner. The lyophilization can be performed, for example, by appropriately sterilizing the composition of the present invention in a liquid form, dispensing an aliquot into a vial container, performing preliminary freezing for 2 hours at conditions of about −40 to −20° C., performing a primary drying at about 0 to 10° C. under reduced pressure, and then performing a secondary drying at about 15 to 25° C. under reduced pressure. In general, the lyophilized preparation of the composition of the present invention can be obtained by replacing the content of the vial with nitrogen gas and capping.

The lyophilized preparation of the composition of the present invention can be used in general upon reconstitution by adding an optional suitable solution (reconstitution liquid) and redissolving the preparation. Such a reconstitution liquid includes injectable water, physiological saline and other infusion fluids. A volume of the reconstitution liquid may vary depending on the intended use, etc., is not particularly limited, and is suitably 0.5 to 2-fold greater than the volume prior to lyophilization or no more than 500 mL.

It is desired to control a dose of the composition of the present invention to be administered, by taking the following factors into account: the type and dosage form of the oligomer of the present invention contained; patients' conditions including age, body weight, etc.; administration route; and the characteristics and extent of the disease. A daily dose calculated as the amount of the antisense oligomer of the present invention is generally in a range of 0.1 mg to 10 g/human, and preferably 1 mg to 1 g/human. This numerical range may vary occasionally depending on type of the target disease, administration route and target molecule. Therefore, a dose lower than the range may be sufficient in some occasion and conversely, a dose higher than the range may be required occasionally. The composition can be administered from once to several times daily or at intervals from one day to several days.

In still another embodiment of the composition of the present invention, there is provided a pharmaceutical composition comprising a vector capable of expressing the oligonucleotide of the present invention and the carrier described above. Such an expression vector may be a vector capable of expressing a plurality of the oligonucleotides of the present invention. The composition may be formulated with pharmaceutically acceptable additives as in the case with the composition of the present invention containing the oligomer of the present invention. A concentration of the expression vector contained in the composition may vary depending upon type of the career, etc., and is appropriately in a range of 0.1 nM to 100 μM, preferably in a range of 1 nM to 10 μM, and more preferably in a range of 10 nM to 1 μM. A weight ratio of the expression vector contained in the composition and the carrier (carrier/expression vector) may vary depending on property of the expression vector, type of the carrier, etc., and is appropriately in a range of 0.1 to 100, preferably in a range of 1 to 50, and more preferably in a range of 10 to 20. The content of the carrier contained in the composition is the same as in the case with the composition of the present invention containing the oligomer of the present invention, and a method for producing the same is also the same as in the case with the composition of the present invention.

Hereinafter, the present invention will be described in more detail with reference to EXAMPLES and TEST EXAMPLES below, but is not deemed to be limited thereto.

EXAMPLES

Reference Example 1

4-{[(2S,6R)-6-(4-Benzamido-2-oxopyrimidin-1-yl)-4-tritylmorpholin-2-yl] methoxy}-4-oxobutanoic acid loaded onto amino polystyrene resin Step 1: Production of 4-{[(2S,6R)-6-(4-benzamido-2-oxopyrimidin-1(2H)-yl)-4-tritylmorpholin-2-yl] methoxy}-4-oxobutanoic acid Under argon atmosphere, 3.44 g of N-{1-[(2R,6S)-6-(hydroxymethyl)-4-tritylmorpholin-2-yl]-2-oxo-1,2-dihydropyrimidin-4-yl}benzamide and 1.1 g of 4-dimethylaminopyridine (4-DMAP) were suspended in 50 mL of dichloromethane, and 0.90 g of succinic anhydride was added to the suspension, followed by stirring at room temperature for 3 hours. To the reaction mixture was added 10 mL of methanol, and the mixture was concentrated under reduced pressure. The residue was extracted using ethyl acetate and 0.5 M aqueous potassium dihydrogenphosphate solution. The resulting organic layer was washed sequentially with 0.5M aqueous potassium dihydrogenphosphate solution, water and brine in the order mentioned. The resulting organic layer was dried over sodium sulfate and concentrated under reduced pressure to give 4.0 g of the product.

Step 2; Production of 4-{[(2S,6R)-6-(4-benzamido-2-oxopyrimidin-1-yl)-4-tritylmorpholin-2-yl] methoxy}-4-oxobutanoic acid loaded onto amino polystyrene resin After 4.0 g of 4-{[(2S,6R)-6-(4-benzamido-2-oxopyrimidin-1(2H)-yl)-4-tritylmorpholin-2-yl]methoxy}-4-oxobutanoic acid was dissolved in 200 mL of pyridine (dehydrated), 0.73 g of 4-DMAP and 11.5 g of 1-ethyl-3-(3-dimethylaminopropyl)carbodiimide hydrochloride were added to the solution. Then, 25.0 g of amino polystyrene resin Primer support 200 amino (manufactured by GE Healthcare Japan Co., Ltd., 17-5214-97) and 8.5 mL of triethylamine were added to the mixture, followed by shaking at room temperature for 4 days. After completion of the reaction, the resin was taken out by filtration. The resulting resin was washed sequentially with pyridine, methanol and dichloromethane in the order mentioned, and dried under reduced pressure. To the resulting resin were added 200 mL of tetrahydrofuran (dehydrate), 15 mL of acetic anhydride and 15 mL of 2,6-lutidine, and the mixture was shaken at room temperature for 2 hours. The resin was taken out by filtration, washed sequentially with pyridine, methanol and dichloromethane in the order mentioned and dried under reduced pressure to give 26.7 g of the product.

The loading amount of the product was determined from the molar amount of the trityl per g resin by measuring UV absorbance at 409 nm using a known method. The loading amount of the resin was 192.2 μmol/g.

Conditions of UV Measurement

Apparatus: U-2910 (Hitachi, Ltd.)

Solvent: methanesulfonic acid

Wavelength: 265 nm

ε value: 45000

Reference Example 2

4-{[(2S,6R)-6-(5-methyl-2,4-dioxopyrimidine-1-yl)-4-tritylmorpholin-2-yl]methoxy}-4-oxobutanoic aced loaded onto amino polystyrene resin The title compound was produced in a manner similar to REFERENCE EXAMPLE 1, except that 1-[(2R,6S)-6-(hydroxymethyl)-4-tritylmorpholin-2-yl]-5-methylpyrimidine-2,4 (1H,3H)-dione was used in this step, instead of N-{1-[(2R,6S)-6-(hydroxymethyl)-4-tritylmorpholin-2-yl]-2-oxo-1,2-dihydropyrimidin-4-yl}benzamide used in Step 1 of REFERENCE EXAMPLE 1.

The loading amount of the product was determined from the molar amount of the trityl per g resin by measuring UV absorbance at 409 nm using a known method. The loading amount of the resin was 164.0 μmol/g.

Reference Example 3

4-{[(2S,6R)-6-(6-benzamido purine-9-yl)-4-tritylmorpholin-2-yl] methoxy}-4-oxobutanoic aced loaded onto amino polystyrene resin The title compound was produced in a manner similar to REFERENCE EXAMPLE 1, except that N-{9-[(2R,6S)-6-(hydroxymethyl)-4-tritylmorpholin-2-yl] purine-6-yl} benzamido was used in this step, instead of N-{1-[(2R,6S)-6-(hydroxymethyl)-4-tritylmorpholin-2-yl]-2-oxo-1,2-dihydropyrimidin-4-yl}benzamide used in Step 1 of REFERENCE EXAMPLE 1.

The loading amount of the product was determined from the molar amount of the trityl per g resin by measuring UV absorbance at 409 nm using a known method. The loading amount of the resin was 185.7 µmol/g.

Reference Example 4

4-{{(2S,6R)-6-{6-2-cyanoethoxyl-2-[(2-phenoxy-acetyl) amino] purine-9-yl}-4-tritylmorpholin-2-yl}methoxy}-4-oxobutanoic aced loaded onto amino polystyrene resin The title compound was produced in a manner similar to REFERENCE EXAMPLE 1, except that N-{6-(2-cyanoethoxy)-9-[(2R,6S)-6-(hydroxymethyl)-4-tritylmorpholin-2-yl]purine-2-yl}-2-phenoxyacetoamido was used in this step, instead of N-{1[(2R,6S)-6-(hydroxymethyl)-4-tritylmorpholin-2-yl]-2-oxo-1,2-dihydropyrimidin-4-yl} benzamide used in Step 1 of REFERENCE EXAMPLE 1.

The loading amount of the product was determined from the molar amount of the trityl per g resin by measuring UV absorbance at 409 nm using a known method. The loading amount of the resin was 164.8 µmol/g.

According to the descriptions in EXAMPLES 1 below, PMO shown by PMO Nos. 1-118 in TABLE 1 were synthesized. PMO Nos. 119 and 120 were purchased from Gene Tools, LLC. The synthesized PMO was dissolved in water for injection (manufactured by Otsuka Pharmaceutical Factory, Inc.).

TABLE 1

| PMO No. | Target sequence positioned in exon 44 | Note | SEQ ID NO: |
|---|---|---|---|
| 1 | 11-23 & 91-103 | 5' end: group (3) | 11 |
| 2 | 11-23 & 61-73 | 5' end: group (3) | 12 |
| 3 | 11-23 & 71-83 | 5' end: group (3) | 13 |
| 4 | 21-33 & 91-103 | 5' end: group (3) | 14 |
| 5 | 21-33 & 81-93 | 5' end: group (3) | 15 |
| 6 | 21-33 & 101-113 | 5' end: group (3) | 16 |
| 7 | 21-33 & 61-73 | 5' end: group (3) | 17 |
| 8 | 21-33 & 71-83 | 5' end: group (3) | 18 |
| 9 | 21-35 & 101-115 | 5' end: group (3) | 19 |
| 10 | 11-25 & 91-105 | 5' end: group (3) | 20 |
| 11 | 16-25 & 101-115 | 5' end: group (3) | 21 |
| 12 | 21-35 & 91-105 | 5' end: group (3) | 22 |
| 13 | 11-23 & 101-113 | 5' end: group (3) | 23 |
| 14 | 23-35 & 91-103 | 5' end: group (3) | 24 |
| 15 | 19-31 & 91-103 | 5' end: group (3) | 25 |
| 16 | 21-33 & 89-101 | 5' end: group (3) | 26 |
| 17 | 11-23 & 81-93 | 5' end: group (3) | 27 |
| 18 | 19-31 & 93-105 | 5' end: group (3) | 28 |
| 19 | 23-35 & 89-101 | 5' end: group (3) | 29 |
| 20 | 23-35 & 93-105 | 5' end: group (3) | 30 |
| 21 | 22-33 & 92-103 | 5' end: group (3) | 31 |
| 22 | 91-103 & 21-33 | 5' end: group (3) | 32 |
| 23 | 22-32 & 92-102 | 5' end: group (3) | 33 |
| 24 | 22-31 & 93-102 | 5' end: group (3) | 34 |
| 25 | 19-31 & 59-71 | 5' end: group (3) | 35 |
| 26 | 21-33 & 93-105 | 5' end: group (3) | 36 |
| 27 | 21-33 & 63-75 | 5' end: group (3) | 37 |
| 28 | 19-31 & 61-73 | 5' end: group (3) | 38 |
| 29 | 19-31 & 63-75 | 5' end: group (3) | 39 |
| 30 | 21-33 & 59-71 | 5' end: group (3) | 40 |
| 31 | 23-35 & 61-73 | 5' end: group (3) | 41 |
| 32 | 23-35 & 63-75 | 5' end: group (3) | 42 |
| 33 | 23-35 & 59-71 | 5' end: group (3) | 43 |
| 34 | 19-31 & 89-101 | 5' end: group (3) | 6 |
| 35 | 61-73 & 91-103 | 5' end: group (3) | 44 |
| 36 | 61-73 & 72-84 | 5' end: group (3) | 45 |
| 37 | 24-33 & 62-71 | 5' end: group (3) | 46 |
| 38 | 24-33 & 65-74 | 5' end: group (3) | 47 |
| 39 | 61-70 & 75-84 | 5' end: group (3) | 48 |
| 40 | 22-31 & 65-74 | 5' end: group (3) | 49 |
| 41 | 17-29 & 91-103 | 5' end: group (3) | 50 |
| 42 | 33-44 & 62-74 | 5' end: group (3) | 51 |

TABLE 1-continued

| PMO No. | Target sequence positioned in exon 44 | Note | SEQ ID NO: |
|---|---|---|---|
| 43 | 26-37 & 65-76 | 5' end: group (3) | 52 |
| 44 | 23-33 & 61-71 | 5' end: group (3) | 53 |
| 45 | 23-33 & 65-75 | 5' end: group (3) | 7 |
| 46 | 22-32 & 64-74 | 5' end: group (3) | 54 |
| 47 | 59-68 & 77-86 | 5' end: group (3) | 55 |
| 48 | 58-70 & 75-87 | 5' end: group (3) | 56 |
| 49 | 22-33 & 63-74 | 5' end: group (3) | 8 |
| 50 | 61-73 & 81-93 | 5' end: group (3) | 57 |
| 51 | 93-103 & 25-35 | 5' end: group (3) | 58 |
| 52 | 17-29 ATT 91-102 | 5' end: group (3) | 59 |
| 53 | 92-103 & 22-33 | 5' end: group (3) | 60 |
| 54 | 91-103 & 19-31 | 5' end: group (3) | 61 |
| 55 | 61-73 & 19-31 | 5' end: group (3) | 62 |
| 56 | 61-73 & 85-97 | 5' end: group (3) | 63 |
| 57 | 69-81 CTCC 61-68 | 5' end: group (3) | 64 |
| 58 | 93-105 & 23-35 | 5' end: group (3) | 65 |
| 59 | 90-103 & 25-36 | 5' end: group (3) | 66 |
| 60 | CT-[61-76]-AC | 5' end: group (3) | 67 |
| 61 | 84-96 & 21-33 | 5' end: group (3) | 68 |
| 62 | 81-93 & 23-35 | 5' end: group (3) | 69 |
| 63 | CC-[61-80]-CC | 5' end: group (3) | 70 |
| 64 | CTT-[61-78]-CCC | 5' end: group (3) | 71 |
| 65 | 84-93 & 23-33 | 5' end: group (3) | 72 |
| 66 | 89-101 & 19-31 | 5' end: group (3) | 73 |
| 67 | 91-103 & 61-73 | 5' end: group (3) | 74 |
| 68 | 61-71 & 91-105 | 5' end: group (3) | 75 |
| 69 | 20-30 & 89-99 | 5' end: group (3) | 76 |
| 70 | 64-74 & 93-103 | 5' end: group (3) | 77 |
| 71 | 20-31 & 89-100 | 5' end: group (3) | 78 |
| 72 | 1-13 & 76-88 | 5' end: group (3) | 79 |
| 73 | 64-75 & 92-103 | 5' end: group (3) | 9 |
| 74 | 99-108 & 19-34 | 5' end: group (3) | 80 |
| 75 | 58-67 & 76-85 | 5' end: group (3) | 81 |
| 76 | 58-67 & 77-86 | 5' end: group (3) | 82 |
| 77 | 23-33 & 92-102 | 5' end: group (3) | 83 |
| 78 | 20-30 & 90-100 | 5' end: group (3) | 84 |
| 79 | 93-104 & 22-33 | 5' end: group (3) | 85 |
| 80 | 93-103 & 23-33 | 5' end: group (3) | 86 |
| 81 | 64-73 & 76-85 | 5' end: group (3) | 87 |
| 82 | 64-74 & 86-95 | 5' end: group (3) | 88 |
| 83 | 58-66 & 77-85 | 5' end: group (3) | 89 |
| 84 | 64-73 & 84-93 | 5' end: group (3) | 90 |
| 85 | 21-31 & 90-100 | 5' end: group (3) | 91 |
| 86 | 20-30 & 87-97 | 5' end: group (3) | 92 |
| 87 | 27-36 & 89-97 | 5' end: group (3) | 93 |
| 88 | 20-29 ATT 91-100 | 5' end: group (3) | 94 |
| 89 | 20-29 ATT 91-97 | 5' end: group (3) | 95 |
| 90 | 20-29 & 88-97 | 5' end: group (3) | 96 |
| 91 | 22-31 & 63-74 | 5' end: group (3) | 97 |
| 92 | 64-76 & 96-102 +C | 5' end: group (3) | 98 |
| 93 | 58-68 & 77-85 +C | 5' end: group (3) | 99 |
| 94 | 22-36 & 89-97 | 5' end: group (3) | 100 |
| 95 | 19-31 & 89-100 | 5' end: group (3) | 101 |
| 96 | 22-31 & 87-97 | 5' end: group (3) | 102 |
| 97 | -1-11 & 62-73 | 5' end: group (3) | 103 |
| 98 | -1-11 & 89-100 | 5' end: group (3) | 104 |
| 99 | -1-11 & 20-31 | 5' end: group (3) | 105 |
| 100 | 20-31 & 89-101 | 5' end: group (3) | 106 |
| 101 | 19-31 & 90-101 | 5' end: group (3) | 107 |
| 102 | 20-31 & 90-101 | 5' end: group (3) | 108 |
| 103 | -1-13 & 76-82 | 5' end: group (3) | 109 |
| 104 | -1-10 & 63-73 | 5' end: group (3) | 110 |
| 105 | -1-10 & 90-100 | 5' end: group (3) | 111 |
| 106 | -1-10 & 20-30 | 5' end: group (3) | 112 |
| 107 | 20-31 & 91-101 | 5' end: group (3) | 113 |
| 108 | 19-31 & 89-101 | 5' end: group (3) 3' end: acetylation | 6 |
| 109 | 20-31 | 5' end: group (3) | 114 |
| 110 | 65-75 | 5' end: group (3) | 115 |
| 111 | 23-33 | 5' end: group (3) | 116 |
| 112 | 92-103 | 5' end: group (3) | 117 |
| 113 | 64-75 | 5' end: group (3) | 118 |
| 114 | 89-101 | 5' end: group (3) | 119 |
| 115 | 19-31 | 5' end: group (3) | 120 |
| 116 | 20-31 & 89-101 | 5' end: group (3) 3' end: acetylation | 106 |
| 117 | 63-74 | 5' end: group (3) | 121 |

TABLE 1-continued

| PMO No. | Target sequence positioned in exon 44 | Note | SEQ ID NO: |
|---|---|---|---|
| 118 | 22-33 | 5' end: group (3) | 122 |
| 119 | 59-68 | 5' end: group (2) | 123 |
| 120 | 77-86 | 5' end: group (2) | 124 |

Example 1

As a base at 5'-terminus, 0.2 g of 4-{[(2S,6R)-6-(4-benzamide-2-oxopyrimidin-1(2H)-yl)-4-tritylmorpholin-2-yl]methoxyl}4-oxobutanoic acid supported on an aminopolystyrene resin (Reference Example 1), 4-{[(2S,6R)-6-(5-methyl-2,4-dioxopyrimidine-1-yl)-4-tritylmorpholin-2-yl]methoxy}-4-oxobutanoic acid supported on an aminopolystyrene resin (Reference Example 2), 4-{[(2S,6R)-6-(6-benzamido purin-9-yl)-4-tritylmorpholin-2-yl] methoxy}-4-oxobutanoic acid supported on an aminopolystyrene resin (Reference Example 3), or 4-{{(2S,6R)-6-{6-(2-cyanoethoxy)-2-[(2-phenoxyacetyl) amino] purin-9-yl}-4-tritylmorpholin-2-yl}methoxy}-4-oxobutanoic acid supported on an aminopolystyrene resin (Reference Example 4), was filled in a column with a filter. Then, the synthetic cycle shown below was started using an oligonucleotide synthesizer (AKTA Oligopilot 10 plus). The desired morpholino monomer compound was added in each coupling cycle to give the base sequence described in Table 1 (see the Table 2 below).

TABLE 2

| Step | Reagent | Volume (mL) | Time (min)) |
|---|---|---|---|
| 1 | deblocking solution | 18 to 32 | 1.8 to 3.2 |
| 2 | neutralizing and washing solution | 30 | 1.5 |
| 3 | coupling solution B | 5 | 0.5 |
| 4 | coupling solution A | 1.3 | 0.25 |
| 5 | coupling reaction by the reagents added in the steps 3 and 4 | | 120 to 300 |
| 6 | acetonitrile | 20 | 1.0 |
| 7 | capping solution | 9 | 2.0 |
| 8 | acetonitrile | 30 | 2.0 |

Note:
Steps 1, 2, 7 and 8 were performed again after final cycle only in case of acetylation of 3'-terminus.

The deblocking solution used was dichloromethane solution containing 3% (w/v) trifluoroacetic acid. The neutralizing and washing solution used was a solution obtained by dissolving N,N-diisopropylethylamine to be 10% (v/v) and tetrahydrofuran to be 5% (v/v) in dichloromethane containing 35% (v/v) acetonitrile. The coupling solution A used was a solution obtained by dissolving the morpholino monomer compound in tetrahydrofuran to be 0.10 M. The coupling solution B used was a solution obtained by dissolving N,N-diisopropylethylamine to be 20% (v/v) and tetrahydrofuran to be 10% (v/v) in acetonitrile. The capping solution used was a solution obtained by dissolving 20% (v/v) acetic anhydride and 30% (v/v) 2,6-lutidine in acetonitrile.

The aminopolystyrene resin loaded with the PMO synthesized above was recovered from the reaction vessel and dried at room temperature for at least 2 hours under reduced pressure. The dried PMO loaded onto aminopolystyrene resin was charged in a reaction vessel, and 5 mL of 28% ammonia water-ethanol (1/4) was added thereto. The mixture was stirred at 55° C. for 15 hours. The aminopolystyrene resin was separated by filtration and washed with 1 mL of water-ethanol (1/4). The resulting filtrate was concentrated under reduced pressure. The resulting residue was dissolved in 10 mL of a solvent mixture of 20 mM of acetic acid—triethylamine buffer (TEAA buffer) and acetonitrile (4/1) and filtered through a membrane filter. The filtrate obtained was purified by reversed phase HPLC. The conditions used are as shown in Table 3 below.

TABLE 3

| Column | XBridge 5 μm C18 (Waters, ϕ19 × 50 mm, 1 CV = 14 mL) |
|---|---|
| Flow rate | 10 mL/min |
| Column temperature | room temperature |
| Solution A | 20 mM TEAA buffer |
| Solution B | $CH_3CN$ |
| Gradient | (B) conc. 10→70%/15 CV |

CV: column volume

Each fraction was analyzed, and the objective product was recovered and concentrated under reduced pressure. To the concentrated residue was added 0.5 mL of 2 M phosphoric acid aqueous solution, and the mixture was stirred for 15 minutes. Furthermore, 2 mL of 2 M sodium hydroxide aqueous solution was added to make the mixture alkaline, followed by filtration through a membrane filter (0.45 μm).

The resulting aqueous solution containing the objective product was purified by an anionic exchange resin column. The conditions used are as shown in Table 4 below.

TABLE 4

| Column | Source 15Q (GE Healthcare, ϕ10 × 108 mm, 1 CV = 8.5 mL) |
|---|---|
| Flow rate | 8.5 mL/min |
| Column temperature | room temperature |
| Solution A | 10 mM sodium hydroxide aqueous solution |
| Solution B | 10 mM sodium hydroxide aqueous solution, 1M sodium chloride aqueous solution |
| Gradient | (B) conc. 1→50%/40 CV |

Each fraction was analyzed (on HPLC) and the objective product was obtained as an aqueous solution. To the resulting aqueous solution was added 0.1 M phosphate buffer (pH 6.0) for neutralization. Next, the mixture obtained was desalted by reversed phase HPLC under the conditions described in Table 5 below.

TABLE 5

| Column | XBridge 5 μm C8 (Waters, ϕ10 × 50 mm, 1 CV = 4 mL) |
|---|---|
| Flow rate | 4 mL/min |
| Column temperature | 60° C. |
| Solution A | water |
| Solution B | $CH_3CN$ |
| Gradient | (B) conc. 0→50%/20 CV |

The objective product was recovered and the mixture was concentrated under reduced pressure. The resulting residue was dissolved in water. The aqueous solution obtained was freeze-dried to give the objective compound as a white cotton-like solid.

The calculated values and the found values of ESI-TOF-MS are represented in the Table 6 below.

TABLE 6

| PMO No. | Target sequence in exon 44 | Calcd. | Found |
|---|---|---|---|
| 1 | H44_11-23_91-103 | 8539.94 | 8539.52 |
| 2 | H44_11-23_61-73 | 8551.97 | 8552.69 |
| 3 | H44_11-23_71-83 | 8533.95 | 8535.46 |
| 4 | H44_21-33_91-103 | 8507.92 | 8507.71 |
| 5 | H44_21-33_81-93 | 8543.96 | 8543.98 |
| 6 | H44_21-33_101-113 | 8534.95 | 8535.75 |
| 7 | H44_21-33_61-73 | 8519.95 | 8520.14 |
| 8 | H44_21-33_71-83 | 8501.93 | 8501.81 |
| 9 | H44_21-35_101-115 | 9882.42 | 9882.06 |
| 10 | H44_11-25_91-105 | 9869.39 | 9870.94 |
| 11 | H44_16-25_101-115 | 8226.85 | 8227.78 |
| 12 | H44_21-35_91-105 | 9855.39 | 9855.53 |
| 13 | H44_11-23_101-113 | 8566.97 | 8566.58 |
| 14 | H44_23-35_91-103 | 8540.94 | 8541.52 |
| 15 | H44_19-31_91-103 | 8491.92 | 8491.90 |
| 16 | H44_21-33_89-101 | 8541.94 | 8541.87 |
| 17 | H44_11-23_81-93 | 8575.98 | 8576.67 |
| 18 | H44_19-31_93-105 | 8475.92 | 8476.50 |
| 19 | H44_23-35_89-101 | 8574.96 | 8574.70 |
| 20 | H44_23-35_93-105 | 8524.94 | 8524.71 |
| 21 | H44_22-33_92-103 | 7822.69 | 7823.21 |
| 22 | H44_91-103_21-33 | 8507.92 | 8508.59 |
| 23 | H44_22-32_92-102 | 7177.47 | 7177.58 |
| 24 | H44_22-31_93-102 | 6492.24 | 6492.03 |
| 25 | H44_19-31_59-71 | 8478.94 | 8478.90 |
| 26 | H44_21-33_93-105 | 8491.92 | 8492.33 |
| 27 | H44_21-33_63-75 | 8470.93 | 8471.09 |
| 28 | H44_19-31_61-73 | 8503.95 | 8503.87 |
| 29 | H44_19-31_63-75 | 8454.93 | 8454.94 |
| 30 | H44_21-33_59-71 | 8494.94 | 8494.90 |
| 31 | H44_23-35_61-73 | 8552.97 | 8552.40 |
| 32 | H44_23-35_63-75 | 8503.95 | 8504.17 |
| 33 | H44_23-35_59-71 | 8527.96 | 8527.97 |
| 34 | H44_19-31_89-101 | 8525.94 | 8525.93 |
| 35 | H44_61-73_91-103 | 8595.95 | 8595.95 |
| 36 | H44_61-73_72-84 | 8589.96 | 8590.03 |
| 37 | H44_24-33_62-71 | 6520.27 | 6519.69 |
| 38 | H44_24-33_65-74 | 6520.27 | 6520.36 |
| 39 | H44_61-70_75-84 | 6574.28 | 6573.63 |
| 40 | H44_22-31_65-74 | 6495.26 | 6495.21 |
| 41 | H44_17-29_91-103 | 8515.93 | 8515.62 |
| 42 | H44_33-44_62-74 | 8254.88 | 8254.88 |
| 43 | H44_26-37_65-76 | 7876.75 | 7876.96 |
| 44 | H44_23-33_61-71 | 7189.50 | 7189.75 |
| 45 | H44_23-33_65-75 | 7180.49 | 7180.75 |
| 46 | H44_22-32_64-74 | 7165.49 | 7165.64 |
| 47 | H44_59-68_77-86 | 6559.28 | 6559.32 |
| 48 | H44_58-70_75-87 | 8566.97 | 8567.64 |
| 49 | H44_22-33_63-74 | 7810.71 | 7810.77 |
| 50 | H44_61-73_81-93 | 8631.99 | 8632.04 |
| 51 | H44_93-103_25-35 | 7195.49 | 7195.55 |
| 52 | H44_17-29_ATT_91-102 | 9185.16 | 9186.41 |
| 53 | H44_92-103_22-33 | 7822.69 | 7822.17 |
| 54 | H44_91-103_19-31 | 8491.92 | 8491.77 |
| 55 | H44_61-73_19-31 | 8503.95 | 8503.41 |
| 56 | H44_61-73_85-97 | 8591.98 | 8591.55 |
| 57 | H44_69-81_CTCC_61-68 | 8164.83 | 8165.78 |
| 58 | H44_93-105_23-35 | 8524.94 | 8525.05 |
| 59 | H44_90-103_25-36 | 8558.96 | 8558.71 |
| 60 | CT-[H44_61-76]-AC | 6534.27 | 6534.04 |
| 61 | H44_84-96_21-33 | 8518.95 | 8518.86 |
| 62 | H44_81-93_23-35 | 8576.98 | 8577.13 |
| 63 | CC-[H44_61-80]-CC | 7819.72 | 7818.92 |
| 64 | CTT-[H44_61-78]-CCC | 7825.71 | 7825.02 |
| 65 | H44_84-93_23-33 | 6883.40 | 6882.97 |
| 66 | H44_89-101_19-31 | 8525.94 | 8526.46 |
| 67 | H44_91-103_61-73 | 8595.95 | 8595.17 |
| 68 | H44_61-71_91-105 | 8579.95 | 8579.71 |
| 69 | H44_20-30_89-99 | 7186.48 | 7186.30 |
| 70 | H44_64-74_93-103 | 7201.48 | 7202.00 |
| 71 | H44_20-31_89-100 | 7831.70 | 7831.77 |
| 72 | H44_1-13_76-88 | 8551.97 | 8552.42 |
| 73 | H44_64-75_92-103 | 7861.70 | 7861.72 |
| 74 | H44_99-108_19-34 | 8583.97 | 8583.87 |
| 75 | H44_58-67_76-85 | 6534.27 | 6533.87 |
| 76 | H44_58-67_77-86 | 6543.28 | 6542.70 |
| 77 | H44_23-33_92-102 | 7177.47 | 7176.76 |
| 78 | H44_20-30_90-100 | 7161.47 | 7161.32 |
| 79 | H44_93-104_22-33 | 7822.69 | 7823.23 |
| 80 | H44_93-103_23-33 | 7177.47 | 7177.09 |
| 81 | H44_64-73_76-85 | 6550.27 | 6549.41 |
| 82 | H44_64-74_86-95 | 6922.41 | 6921.39 |
| 83 | H44_58-66_77-85 | 5889.05 | 5888.11 |
| 84 | H44_64-73_84-93 | 6592.30 | 6591.14 |
| 85 | H44_21-31_90-100 | 7161.47 | 7160.62 |
| 86 | H44_20-30_87-97 | 7179.49 | 7178.65 |
| 87 | H44_27-36_89-97 | 6214.17 | 6213.81 |
| 88 | H44_20-29_ATT_91-100 | 7506.58 | 7505.79 |
| 89 | H44_20-29_ATT_91-97 | 6491.24 | 6490.34 |
| 90 | H44_20-29_88-97 | 6525.26 | 6523.73 |
| 91 | H44_22-31_63-74 | 7140.48 | 7139.34 |
| 92 | H44_64-76_96-102+C | 6871.37 | 6869.58 |
| 93 | H44_58-68_77-85+C | 6874.39 | 6872.78 |
| 94 | H44_22-36_89-97 | 7858.73 | 7859.53 |
| 95 | H44_19-31_89-100 | 8170.82 | 8171.89 |
| 96 | H44_22-31_87-97 | 6849.38 | 6849.17 |
| 97 | H44_-1-11_62-73 | 7898.74 | 7899.01 |
| 98 | H44_-1-11_89-100 | 7904.73 | 7904.14 |
| 99 | H44_-1-11_20-31 | 7794.71 | 7794.30 |
| 100 | H44_20-31_89-101 | 8186.82 | 8186.63 |
| 101 | H44_19-31_90-101 | 8170.82 | 8170.92 |
| 102 | H44_20-31_90-101 | 7831.70 | 7831.48 |
| 103 | H44_-1-13_76-82 | 6849.38 | 6848.35 |
| 104 | H44_-1-10_63-73 | 7213.51 | 7211.46 |
| 105 | H44_-1-10_90-100 | 7219.50 | 7218.65 |
| 106 | H44_-1-10_20-30 | 7149.49 | 7151.40 |
| 107 | H44_20-31_91-101 | 7492.58 | 7493.67 |
| 108 | H44_19-31_89-101(N—Ac) | 8567.95 | 8568.51 |
| 109 | H44_20-31 | 3816.34 | 3816.82 |
| 110 | H44_65-75 | 3565.25 | 3565.61 |
| 111 | H44_23-33 | 3526.24 | 3526.57 |
| 112 | H44_92-103 | 3892.34 | 3892.71 |
| 113 | H44_64-75 | 3880.36 | 3880.72 |
| 114 | H44_89-101 | 4281.48 | 4282.08 |
| 115 | H44_19-31 | 4155.46 | 4156.03 |
| 116 | H44_20-31_89-101(N—Ac) | 8228.83 | 8229.03 |
| 117 | H44_63-74 | 3880.36 | 3880.21 |
| 118 | H44_22-33 | 3841.35 | 3841.30 |

Test Example 1

In Vitro Assay

Using an Amaxa Cell Line Nucleofector Kit L on Nucleofector II (Lonza), 0.1 to 30 μM of the antisense oligomers in Table 1 were transfected with $3.5 \times 10^5$ of RD cells (human rhabdomyosarcoma cell line). The Program T-030 was used.

After transfection, the cells were cultured for three nights in 2 mL of Eagle's minimal essential medium (EMEM) (manufactured by Sigma, hereinafter the same) containing 10% fetal calf serum (FCS) (manufactured by Invitrogen) under conditions of 37° C. and 5% $CO_2$.

The cells were washed one time with PBS (manufactured by Nissui, hereinafter the same) and 350 μl of Buffer RLT (manufactured by Qiagen) containing 1% 2-mercaptoethanol (manufactured by Nacalai Tesque) was added to the cells. After the cells were allowed to stand at room temperature for a few minutes to lyse the cells, the lysate was collected in a QIAshredder homogenizer (manufactured by Qiagen). Then the lysate was centrifuged at 15,000 rpm for 2 minutes to prepare the homogenate. The total RNA was extracted according to the protocol attached to RNeasy Mini Kit (manufactured by Qiagen). The concentration of the total RNA extracted was determined using a NanoDrop ND-1000 (manufactured by LMS).

One-Step RT-PCR was performed with 400 ng of the extracted total RNA using a QIAGEN OneStep RT-PCR Kit (manufactured by Qiagen). A reaction solution was prepared in accordance with the protocol attached to the kit. PTC-100

(manufactured by MJ Research) or TaKaRa PCR Thermal Cycler Dice Touch (manufactured by Takara Bio) was used as a thermal cycler. The RT-PCR program used is as follows.

50° C., 30 mins: reverse transcription reaction

95° C., 15 mins: activation of polymerase, inactivation of reverse transcriptase, thermal denaturation of cDNA

[94° C., 30 seconds; 60° C., 30 seconds; 72° C., 1 min]×35 cycles: PCR amplification 72° C., 10 mins: final extension The base sequences of the forward primer and reverse primer used for RT-PCR are given below.

```
Forward primer:
                               (SEQ ID NO: 125)
5'-GCTCAGGTCGGATTGACATT-3'

Reverse primer:
                               (SEQ ID NO: 126)
5'-GGGCAACTCTTCCACCAGTA-3'
```

The reaction product, 1 µL of the PCR above was analyzed using a Bioanalyzer (manufactured by Agilent Technologies, Inc.).

The polynucleotide level "A" of the band with exon 44 skipping and the polynucleotide level "B" of the band without exon 44 skipping were measured. Based on these measurement values of "A" and "B", the skipping efficiency was determined by the following equation:

Skipping efficiency (%)=$A/(A+B)\times100$

Experimental Results

The results are shown in FIGS. 1 to 26. This experiment revealed that, the oligomer of the present invention obtained by connecting short unit oligomers selected from the −1st to the 44th bases (SEQ ID NO: 1) and the 58th to the 115th bases (SEQ ID NO: 2), respectively, from the 5' end of the nucleotide sequence of exon 44 (SEQ ID NO: 10) in the human wild-type dystrophin gene effectively cause exon 44 skipping.

Test Example 2

In Vitro Assay

The experiment was performed as in TEST EXAMPLE 1 except for that $3.5\times10^5$ of RD cells (human rhabdomyosarcoma cell line) were transfected with the oligomers of the present invention of PMO Nos. 34, 100, 45, 73, 49 and 47 each being alone or in the form where two unit oligomers constituting each oligomer are contained alone or in mixture, at a concentration of 1, 3 or 10 µM, using an Amaxa Cell Line Nucleofector Kit L on Nucleofector II (Lonza). The Program T-030 was used. The combinations of the sequences for the transfection are as follows.

TABLE 7

Combination of transfected sequences

| | combination of sequences | conc. of transfected oligomer (µM) |
|---|---|---|
| 1 | PMO No. 34 | 1 µM |
| 2 | PMO No. 115 or PMO No. 114 or a mixture | 1 µM each |
| 3 | PMO No. 100 | 1 µM |
| 4 | PMO No. 109 or PMO No. 114 or a mixture | 1 µM each |
| 5 | PMO No. 45 | 1 µM |
| 6 | PMO No. 111 or PMO No. 110 or a mixture | 1 µM each |
| 7 | PMO No. 73 | 1 µM |
| 8 | PMO No. 113 or PMO No. 112 or a mixture | 1 µM each |
| 9 | PMO No. 49 | 1 µM |

TABLE 7-continued

Combination of transfected sequences

| | combination of sequences | conc. of transfected oligomer (µM) |
|---|---|---|
| 10 | PMO No. 117 or PMO No. 118 or a mixture | 1 µM each |
| 11 | PMO No. 47 | 3 or 10 µM |
| 12 | PMO No. 119 or PMO No. 120 or a mixture | 3 or 10 µM each |

Experimental Results

The results are shown in FIGS. 27 to 31. This experiment revealed that, each of PMO Nos. 110 to 115, PMO No. 117 and PMO No. 118 targeting a site in exon 44 could not cause exon 44 skipping by itself. This experiment also revealed that, as compared with mixtures of two antisense nucleic acids targeting different sites in exon 44 (the mixture of PMO No. 114 and PMO No. 115; the mixture of PMO No. 109 and PMO No. 114; the mixture of PMO No. 110 and PMO No. 111; the mixture of PMO No. 112 and PMO No. 113; the mixture of PMO No. 117 and PMO No. 118; and the mixture of PMO No. 119 and PMO No. 120), the oligomers of the present invention of PMO No. 34, PMO No. 100, PMO No. 45, PMO No. 73, PMO No. 49 and PMO No. 47, where each corresponding unit oligomers are connected with each other, cause exon 44 skipping with high efficiencies.

Test Example 3

In Vitro Assay Using Human Fibroblasts

The exon 44 skipping activity was determined using GM05112 cells (human DMD patient-derived fibroblasts with deletion of exon 45, Coriell Institute for Medical Research). As a growth medium, there was used Dulbecco's Modified Eagle Medium: Nutrient Mixture F-12 (DMEM/F-12) (Life Technologies) containing 10% FCS (HyClone Laboratories, Inc.) and 1% Penicillin/Streptmycin (P/S) (Sigma-Aldrich, Inc.) and the cells were cultured under conditions of 37° C. and 5% $CO_2$.

The cells were cultured in T225 flask and the 2.5 mL of retrovirus (ZsGreen1 coexpression) expressing human derived myoD (SEQ ID NO: 127) and a final concentration of 8 µg/mL of polybrene (Sigma-Aldrich, Inc.) were added to 30 mL of the growth medium. After incubation at 32° C. for 2 days, the medium was exchanged to a fresh growth medium and incubation was further continued at 37° C. for 3 days. ZsGreen1-positive MyoD-transformed fibroblasts were collected by BD FACSAria Cell Sorter (BD Bioscience). The collected cells were suspended in a differentiation medium (DMEM/F-12 containing 2% equine serum (LifeTechnologies), 1% P/S and ITS Liquid Media Supplement (Sigma-Aldrich, Inc.)) and plated at $9.4\times10^4$ cells/well into a collagen-coated 24-well plate. The medium was exchanged every 2 to 3 days and incubation was continued to differentiate into myotubes.

On the 7th day after plating on a 24-well plate, the medium was replaced by a differentiation medium, and 10 µM of the oligomers PMO No. 34, 45, 49 and 73 were added thereto at a final concentration. After the cells were incubated for 2 days, the medium was replaced by a differentiation medium without PMO, and the cells were incubated five more days. Then the cells were collected to extract total RNA using RNeasy Mini Kit (QIAGEN). RT-PCR was performed with 50 ng of the extracted total RNA using a QIAGEN OneStep RT-PCR Kit. A reaction solution was prepared in accordance with the protocol attached to the kit.

An iCycler (manufactured by Bio-Rad Laboratories) was used as a thermal cycler. The RT-PCR program used is as follows.

50° C., 30 mins: reverse transcription reaction
95° C., 15 mins: activation of polymerase, inactivation of reverse transcriptase, thermal denaturation of cDNA
[94° C., 1 min; 60° C., 1 min; 72° C., 1 min]×35 cycles: PCR amplification 72° C., 7 mins: final extension The base sequences of the forward primer and reverse primer used for RT-PCR are given below.

```
Forward primer:
                                    (SEQ ID NO: 125)
5'-GCTCAGGTCGGATTGACATT-3'

Reverse primer:
                                    (SEQ ID NO: 126)
5'-GGGCAACTCTTCCACCAGTA-3'
```

1 μL of PCR product was analyzed by Experion DNA 1K Analysis Kits (Bio-Rad Laboratories) using Experion Electrophoresis Station (Bio-Rad Laboratories). DNA 1K assay was selected on Experion Software version 3.2 (Bio-Rad Laboratories) and measured. The level (A) of the band around 317 bp and the level (B) of the band around 465 bp were determined (unit: nmol/L). The skipping efficiency (%) was determined by the following equation using Excel 2007 SP3 (Microsoft).

$$\text{Skipping efficiency (\%)}=A/(A+B)\times 100$$

Experimental Results

The results are shown in FIG. 32. This experiment revealed that, the antisense oligomers of the present invention of PMO Nos. 34, 45, 49 and 73, could cause exon 44 skipping with a high efficiency in cells from a DMD patient with deletion of exon 45.

INDUSTRIAL APPLICABILITY

Experimental results in TEST EXAMPLES demonstrate that the oligomers of the present invention in which short oligomers are connected caused exon 44 skipping in RD cells. Therefore, the oligomers of the present invention are extremely useful for the treatment of DMD.

Sequence Listing Free Text

The invention claimed is:

1. An antisense oligomer consisting of the nucleotide sequence of SEQ ID NO: 6, 7, 8, or 9, or a pharmaceutically acceptable salt or hydrate thereof, wherein the antisense oligomer induces skipping of exon 44 of a human dystrophin gene, and wherein the antisense oligomer is (i) an oligonucleotide comprising at least one nucleotide having the sugar moiety and/or the phosphate-binding region modified, or (ii) a morpholino oligomer.

2. The antisense oligomer according to claim 1, wherein the modified sugar moiety is a ribose in which the 2'-OH group is replaced by any one selected from the group consisting of OR, R, R'OR, SH, SR, $NH_2$, NHR, $NR_2$, $N_3$, CN, F, Cl, Br and I (wherein R is an alkyl or an aryl and R' is an alkylene), or a pharmaceutically acceptable salt or hydrate thereof.

3. The antisense oligomer according to claim 1, wherein the modified phosphate-binding region is any one selected from the group consisting of a phosphorothioate bond, a phosphorodithioate bond, an alkylphosphonate bond, a phosphoramidate bond and a boranophosphate bond, or a pharmaceutically acceptable salt or hydrate thereof.

4. The antisense oligomer according to claim 1, which is a morpholino oligomer, or a pharmaceutically acceptable salt or hydrate thereof.

5. The antisense oligomer according to claim 4, which is a phosphorodiamidate morpholino oligomer, or a pharmaceutically acceptable salt or hydrate thereof.

6. The antisense oligomer according to claim 4, wherein the 5' end is any one of chemical formulae (1) to (3) below, or a pharmaceutically acceptable salt or hydrate thereof.

[Formula 26]

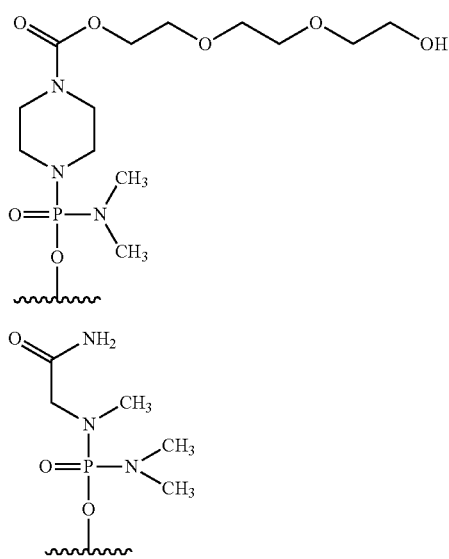

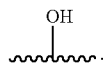

7. A pharmaceutical composition for the treatment of muscular dystrophy, comprising as an active ingredient the antisense oligomer according to claim 1, or a pharmaceutically acceptable salt or hydrate thereof.

8. The pharmaceutical composition according to claim 7, further comprising a pharmaceutically acceptable carrier.

9. A method for treatment of muscular dystrophy, which comprises administering to a patient with muscular dystrophy the antisense oligomer or a pharmaceutically acceptable salt or hydrate thereof according to claim 1 or 2-6.

10. The method for treatment according to claim 9, wherein the patient with muscular dystrophy has a mutation(s) which is to be targeted for exon 44 skipping in dystrophin gene.

11. The method for treatment according to claim 9, wherein the patient is a human.

12. A method for treatment of muscular dystrophy, which comprises administering to a patient with muscular dystrophy the pharmaceutical composition of claim 7 or claim 8.

* * * * *

```
SEQUENCE LISTING

<160> NUMBER OF SEQ ID NOS: 128

<210> SEQ ID NO 1
<211> LENGTH: 45
<212> TYPE: DNA
<213> ORGANISM: Artificial
<220> FEATURE:
<223> OTHER INFORMATION: Synthetic Nucleic Acid

<400> SEQUENCE: 1
ggcgatttga cagatctgtt gagaaatggc ggcgttttca ttatg          45

<210> SEQ ID NO 2
<211> LENGTH: 58
<212> TYPE: DNA
<213> ORGANISM: Artificial
<220> FEATURE:
<223> OTHER INFORMATION: Synthetic Nucleic Acid

<400> SEQUENCE: 2
taatcagtgg ctaacagaag ctgaacagtt tctcagaaag acacaaattc ctgagaat    58

<210> SEQ ID NO 3
<211> LENGTH: 17
<212> TYPE: DNA
<213> ORGANISM: Artificial
<220> FEATURE:
<223> OTHER INFORMATION: Synthetic Nucleic Acid

<400> SEQUENCE: 3
ttgagaaatg gcggcgt                                          17

<210> SEQ ID NO 4
<211> LENGTH: 17
<212> TYPE: DNA
<213> ORGANISM: Artificial
<220> FEATURE:
<223> OTHER INFORMATION: Synthetic Nucleic Acid

<400> SEQUENCE: 4
tcagtggcta acagaag                                          17
```

<210> SEQ ID NO 5
<211> LENGTH: 17
<212> TYPE: DNA
<213> ORGANISM: Artificial
<220> FEATURE:
<223> OTHER INFORMATION: Synthetic Nucleic Acid

<400> SEQUENCE: 5
tctcagaaag acacaaa                                                    17

<210> SEQ ID NO 6
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 6
gtgtctttct gagccgccat ttctca                                          26

<210> SEQ ID NO 7
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 7
tctgttagcc acgccgccat tt                                              22

<210> SEQ ID NO 8
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 8
ctgttagcca ctcgccgcca tttc                                            24

<210> SEQ ID NO 9
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 9
ttgtgtcttt cttctgttag ccac                                            24

<210> SEQ ID NO 10
<211> LENGTH: 148
<212> TYPE: DNA
<213> ORGANISM: Homo sapiens

<400> SEQUENCE: 10
gcgatttgac agatctgttg agaaatggcg gcgttttcat tatgatataa agatatttaa     60
tcagtggcta acagaagctg aacagtttct cagaaagaca caaattcctg agaattggga    120
acatgctaaa tacaaatggt atcttaag                                       148

<210> SEQ ID NO 11
<211> LENGTH: 26
<212> TYPE: DNA
<213> ORGANISM: Artificial

```
<220> FEATURE:
<223> OTHER INFORMATION: Synthetic Nucleic Acid

<400> SEQUENCE: 11
ttgtgtcttt ctgtctcaac agatct                                              26

<210> SEQ ID NO 12
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 12
tgttagccac tgatctcaac agatct                                              26

<210> SEQ ID NO 13
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 13
gttcagcttc tgttctcaac agatct                                              26

<210> SEQ ID NO 14
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 14
ttgtgtcttt ctgcgccgcc atttct                                              26

<210> SEQ ID NO 15
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 15
ctgagaaact gttcgccgcc atttct                                              26

<210> SEQ ID NO 16
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 16
tctcaggaat ttgcgccgcc atttct                                              26

<210> SEQ ID NO 17
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 17
tgttagccac tgacgccgcc atttct                                              26
```

```
<210> SEQ ID NO 18
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 18
gttcagcttc tgtcgccgcc atttct                                          26

<210> SEQ ID NO 19
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 19
attctcagga atttgaacgc cgccatttct                                      30

<210> SEQ ID NO 20
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 20
atttgtgtct ttctgtttct caacagatct                                      30

<210> SEQ ID NO 21
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 21
attctcagga atttgttct caaca                                            25

<210> SEQ ID NO 22
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 22
atttgtgtct ttctgaacgc cgccatttct                                      30

<210> SEQ ID NO 23
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 23
tctcaggaat tgtctcaac agatct                                           26

<210> SEQ ID NO 24
<211> LENGTH: 26
<212> TYPE: DNA
<213> ORGANISM: Artificial
<220> FEATURE:
<223> OTHER INFORMATION: Synthetic Nucleic Acid
```

-continued

<400> SEQUENCE: 24
ttgtgtcttt ctgaacgccg ccattt                                    26

<210> SEQ ID NO 25
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 25
ttgtgtcttt ctgccgccat ttctca                                    26

<210> SEQ ID NO 26
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 26
gtgtctttct gagcgccgcc atttct                                    26

<210> SEQ ID NO 27
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 27
ctgagaaact gtttctcaac agatct                                    26

<210> SEQ ID NO 28
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 28
atttgtgtct ttcccgccat ttctca                                    26

<210> SEQ ID NO 29
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 29
gtgtctttct gagaacgccg ccattt                                    26

<210> SEQ ID NO 30
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 30
atttgtgtct ttcaacgccg ccattt                                    26

```
<210> SEQ ID NO 31
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 31
ttgtgtcttt ctcgccgcca tttc                                          24

<210> SEQ ID NO 32
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 32
cgccgccatt tctttgtgtc tttctg                                        26

<210> SEQ ID NO 33
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 33
tgtgtctttc tgccgccatt tc                                            22

<210> SEQ ID NO 34
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 34
tgtgtctttc ccgccatttc                                               20

<210> SEQ ID NO 35
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 35
ttagccactg attccgccat ttctca                                        26

<210> SEQ ID NO 36
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 36
atttgtgtct ttccgccgcc atttct                                        26

<210> SEQ ID NO 37
<211> LENGTH: 26
<212> TYPE: DNA
<213> ORGANISM: Artificial
<220> FEATURE:
<223> OTHER INFORMATION: Synthetic Nucleic Acid
```

```
<400> SEQUENCE: 37
tctgttagcc actcgccgcc atttct                                              26

<210> SEQ ID NO 38
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 38
tgttagccac tgaccgccat ttctca                                              26

<210> SEQ ID NO 39
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 39
tctgttagcc actccgccat ttctca                                              26

<210> SEQ ID NO 40
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 40
ttagccactg attcgccgcc atttct                                              26

<210> SEQ ID NO 41
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 41
tgttagccac tgaaacgccg ccattt                                              26

<210> SEQ ID NO 42
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 42
tctgttagcc actaacgccg ccattt                                              26

<210> SEQ ID NO 43
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 43
ttagccactg attaacgccg ccattt                                              26
```

```
<210> SEQ ID NO 44
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 44
ttgtgtcttt ctgtgttagc cactga                                              26

<210> SEQ ID NO 45
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 45
tgttcagctt ctgtgttagc cactga                                              26

<210> SEQ ID NO 46
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 46
ttagccactg cgccgccatt                                                     20

<210> SEQ ID NO 47
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 47
ctgttagcca cgccgccatt                                                     20

<210> SEQ ID NO 48
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 48
tgttcagctt tagccactga                                                     20

<210> SEQ ID NO 49
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 49
ctgttagcca ccgccatttc                                                     20

<210> SEQ ID NO 50
<211> LENGTH: 26
<212> TYPE: DNA
<213> ORGANISM: Artificial
<220> FEATURE:
<223> OTHER INFORMATION: Synthetic Nucleic Acid
```

```
<400> SEQUENCE: 50
ttgtgtcttt ctggccattt ctcaac                                          26

<210> SEQ ID NO 51
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 51
ctgttagcca ctgcataatg aaaac                                           25

<210> SEQ ID NO 52
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 52
ttctgttagc caaaaacgcc gcca                                            24

<210> SEQ ID NO 53
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 53
ttagccactg acgccgccat tt                                              22

<210> SEQ ID NO 54
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 54
ctgttagcca cgccgccatt tc                                              22

<210> SEQ ID NO 55
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 55
actgttcagc gccactgatt                                                 20

<210> SEQ ID NO 56
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 56
aactgttcag ctttagccac tgatta                                          26
```

<210> SEQ ID NO 57
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 57
ctgagaaact gtttgttagc cactga                                              26

<210> SEQ ID NO 58
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 58
aacgccgcca tttgtgtctt tc                                                  22

<210> SEQ ID NO 59
<211> LENGTH: 28
<212> TYPE: DNA
<213> ORGANISM: Artificial
<220> FEATURE:
<223> OTHER INFORMATION: Synthetic Nucleic Acid

<400> SEQUENCE: 59
tgtgtctttc tgttagccat ttctcaac                                            28

<210> SEQ ID NO 60
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 60
cgccgccatt tcttgtgtct ttct                                                24

<210> SEQ ID NO 61
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 61
ccgccatttc tcattgtgtc tttctg                                              26

<210> SEQ ID NO 62
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 62
ccgccatttc tcatgttagc cactga                                              26

<210> SEQ ID NO 63
<211> LENGTH: 26
<212> TYPE: DNA
<213> ORGANISM: Artificial
<220> FEATURE:
<223> OTHER INFORMATION: Synthetic Nucleic Acid

```
<400> SEQUENCE: 63
ctttctgaga aactgttagc cactga                                              26

<210> SEQ ID NO 64
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 64
gccactgacc tctcagcttc tgtta                                               25

<210> SEQ ID NO 65
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 65
aacgccgcca tttatttgtg tctttc                                              26

<210> SEQ ID NO 66
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 66
aaacgccgcc atttgtgtct ttctga                                              26

<210> SEQ ID NO 67
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 67
ctttctgtta gccactgaac                                                     20

<210> SEQ ID NO 68
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 68
cgccgccatt tcttttctga gaaact                                              26

<210> SEQ ID NO 69
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 69
aacgccgcca tttctgagaa actgtt                                              26
```

```
<210> SEQ ID NO 70
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 70
cccagcttct gttagccact gacc                                            24

<210> SEQ ID NO 71
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 71
cttgcttctg ttagccactg accc                                            24

<210> SEQ ID NO 72
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 72
cgccgccatt tctgagaaac t                                               21

<210> SEQ ID NO 73
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 73
ccgccatttc tcagtgtctt tctgag                                          26

<210> SEQ ID NO 74
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 74
tgttagccac tgattgtgtc tttctg                                          26

<210> SEQ ID NO 75
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 75
atttgtgtct ttctgttagc cactga                                          26

<210> SEQ ID NO 76
<211> LENGTH: 22
<212> TYPE: DNA
<213> ORGANISM: Artificial
<220> FEATURE:
<223> OTHER INFORMATION: Synthetic Nucleic Acid
```

<400> SEQUENCE: 76
gtctttctga gcgccatttc tc					22

<210> SEQ ID NO 77
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 77
ttgtgtcttt cctgttagcc ac					22

<210> SEQ ID NO 78
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 78
tgtctttctg agccgccatt tctc					24

<210> SEQ ID NO 79
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 79
aaactgttca gcttctgtca aatcgc					26

<210> SEQ ID NO 80
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 80
acgccgccat ttctcaggaa tttgtg					26

<210> SEQ ID NO 81
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 81
ctgttcagct ccactgatta					20

<210> SEQ ID NO 82
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 82
actgttcagc ccactgatta					20

-continued

<210> SEQ ID NO 83
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 83
tgtgtctttc tcgccgccat tt					22

<210> SEQ ID NO 84
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 84
tgtctttctg acgccatttc tc					22

<210> SEQ ID NO 85
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 85
cgccgccatt tctttgtgtc tttc					24

<210> SEQ ID NO 86
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 86
cgccgccatt tttgtgtctt tc					22

<210> SEQ ID NO 87
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 87
ctgttcagct tgttagccac					20

<210> SEQ ID NO 88
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 88
ttctgagaaa ctgttagcca c					21

<210> SEQ ID NO 89
<211> LENGTH: 18
<212> TYPE: DNA
<213> ORGANISM: Artificial
<220> FEATURE:
<223> OTHER INFORMATION: Synthetic Nucleic Acid

```
<400> SEQUENCE: 89
ctgttcagcc actgatta                                              18

<210> SEQ ID NO 90
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 90
ctgagaaact tgttagccac                                            20

<210> SEQ ID NO 91
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 91
tgtctttctg accgccattt ct                                         22

<210> SEQ ID NO 92
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 92
ctttctgaga acgccatttc tc                                         22

<210> SEQ ID NO 93
<211> LENGTH: 19
<212> TYPE: DNA
<213> ORGANISM: Artificial
<220> FEATURE:
<223> OTHER INFORMATION: Synthetic Nucleic Acid

<400> SEQUENCE: 93
ctttctgaga aacgccgcc                                             19

<210> SEQ ID NO 94
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 94
tgtctttctg ttagccattt ctc                                        23

<210> SEQ ID NO 95
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 95
ctttctgtta gccatttctc                                            20
```

<210> SEQ ID NO 96
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 96
ctttctgaga gccatttctc                                         20

<210> SEQ ID NO 97
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 97
ctgttagcca ctccgccatt tc                                      22

<210> SEQ ID NO 98
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 98
ctgtgtcttt ctgttagcca c                                       21

<210> SEQ ID NO 99
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 99
ctgttcagcg ccactgatta c                                       21

<210> SEQ ID NO 100
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 100
ctttctgaga aacgccgcca tttc                                    24

<210> SEQ ID NO 101
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 101
tgtctttctg agccgccatt tctca                                   25

<210> SEQ ID NO 102
<211> LENGTH: 21
<212> TYPE: DNA
<213> ORGANISM: Artificial
<220> FEATURE:
<223> OTHER INFORMATION: Synthetic Nucleic Acid

```
<400> SEQUENCE: 102
ctttctgaga accgccattt c                                              21

<210> SEQ ID NO 103
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 103
tgttagccac tgtgtcaaat cgcc                                           24

<210> SEQ ID NO 104
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 104
tgtctttctg agtgtcaaat cgcc                                           24

<210> SEQ ID NO 105
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 105
ccgccatttc tctgtcaaat cgcc                                           24

<210> SEQ ID NO 106
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 106
gtgtctttct gagccgccat ttctc                                          25

<210> SEQ ID NO 107
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 107
gtgtctttct gaccgccatt tctca                                          25

<210> SEQ ID NO 108
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 108
gtgtctttct gaccgccatt tctc                                           24
```

```
<210> SEQ ID NO 109
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 109
ttcagcttct gtcaaatcgc c                                                21

<210> SEQ ID NO 110
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 110
tgttagccac tgtcaaatcg cc                                               22

<210> SEQ ID NO 111
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 111
tgtctttctg agtcaaatcg cc                                               22

<210> SEQ ID NO 112
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 112
cgccatttct cgtcaaatcg cc                                               22

<210> SEQ ID NO 113
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 113
gtgtctttct gccgccattt ctc                                              23

<210> SEQ ID NO 114
<211> LENGTH: 12
<212> TYPE: DNA
<213> ORGANISM: Artificial
<220> FEATURE:
<223> OTHER INFORMATION: Synthetic Nucleic Acid

<400> SEQUENCE: 114
ccgccatttc tc                                                          12

<210> SEQ ID NO 115
<211> LENGTH: 11
<212> TYPE: DNA
<213> ORGANISM: Artificial
<220> FEATURE:
<223> OTHER INFORMATION: Synthetic Nucleic Acid
```

```
<400> SEQUENCE: 115
tctgttagcc a                                                              11

<210> SEQ ID NO 116
<211> LENGTH: 11
<212> TYPE: DNA
<213> ORGANISM: Artificial
<220> FEATURE:
<223> OTHER INFORMATION: Synthetic Nucleic Acid

<400> SEQUENCE: 116
cgccgccatt t                                                              11

<210> SEQ ID NO 117
<211> LENGTH: 12
<212> TYPE: DNA
<213> ORGANISM: Artificial
<220> FEATURE:
<223> OTHER INFORMATION: Synthetic Nucleic Acid

<400> SEQUENCE: 117
ttgtgtcttt ct                                                             12

<210> SEQ ID NO 118
<211> LENGTH: 12
<212> TYPE: DNA
<213> ORGANISM: Artificial
<220> FEATURE:
<223> OTHER INFORMATION: Synthetic Nucleic Acid

<400> SEQUENCE: 118
tctgttagcc ac                                                             12

<210> SEQ ID NO 119
<211> LENGTH: 13
<212> TYPE: DNA
<213> ORGANISM: Artificial
<220> FEATURE:
<223> OTHER INFORMATION: Synthetic Nucleic Acid

<400> SEQUENCE: 119
gtgtctttct gag                                                            13

<210> SEQ ID NO 120
<211> LENGTH: 13
<212> TYPE: DNA
<213> ORGANISM: Artificial
<220> FEATURE:
<223> OTHER INFORMATION: Synthetic Nucleic Acid

<400> SEQUENCE: 120
ccgccatttc tca                                                            13

<210> SEQ ID NO 121
<211> LENGTH: 12
<212> TYPE: DNA
<213> ORGANISM: Artificial
<220> FEATURE:
<223> OTHER INFORMATION: Synthetic Nucleic Acid

<400> SEQUENCE: 121
ctgttagcca ct                                                             12
```

<210> SEQ ID NO 122
<211> LENGTH: 12
<212> TYPE: DNA
<213> ORGANISM: Artificial
<220> FEATURE:
<223> OTHER INFORMATION: Synthetic Nucleic Acid

<400> SEQUENCE: 122
cgccgccatt tc                                                          12

<210> SEQ ID NO 123
<211> LENGTH: 10
<212> TYPE: DNA
<213> ORGANISM: Artificial
<220> FEATURE:
<223> OTHER INFORMATION: Synthetic Nucleic Acid

<400> SEQUENCE: 123
gccactgatt                                                             10

<210> SEQ ID NO 124
<211> LENGTH: 10
<212> TYPE: DNA
<213> ORGANISM: Artificial
<220> FEATURE:
<223> OTHER INFORMATION: Synthetic Nucleic Acid

<400> SEQUENCE: 124
actgttcagc                                                             10

<210> SEQ ID NO 125
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 125
gctcaggtcg gattgacatt                                                  20

<210> SEQ ID NO 126
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 126
gggcaactct tccaccagta                                                  20

<210> SEQ ID NO 127
<211> LENGTH: 963
<212> TYPE: DNA
<213> ORGANISM: Homo sapiens
<220> FEATURE:
<221> NAME/KEY: CDS
<222> LOCATION: (1)..(963)

<400> SEQUENCE: 127 atg gag cta ctg tcg cca ccg ctc cgc gac gta gac ctg acg gcc ccc        48
Met Glu Leu Leu Ser Pro Pro Leu Arg Asp Val Asp Leu Thr Ala Pro
1               5                   10                  15 gac ggc tct ctc tgc tcc ttt gcc aca acg gac gac ttc tat gac gac        96
Asp Gly Ser Leu Cys Ser Phe Ala Thr Thr Asp Asp Phe Tyr Asp Asp
                20                  25                  30

| | |
|---|---|
| ccg tgt ttc gac tcc ccg gac ctg cgc ttc ttc gaa gac ctg gac ccg<br>Pro Cys Phe Asp Ser Pro Asp Leu Arg Phe Phe Glu Asp Leu Asp Pro<br>35 40 45 | 144 |
| cgc ctg atg cac gtg ggc gcg ctc ctg aaa ccc gaa gag cac tcg cac<br>Arg Leu Met His Val Gly Ala Leu Leu Lys Pro Glu Glu His Ser His<br>50 55 60 | 192 |
| ttc ccc gcg gcg gtg cac ccg gcc ccg ggc gca cgt gag gac gag cat<br>Phe Pro Ala Ala Val His Pro Ala Pro Gly Ala Arg Glu Asp Glu His<br>65 70 75 80 | 240 |
| gtg cgc gcg ccc agc ggg cac cac cag gcg ggc cgc tgc cta ctg tgg<br>Val Arg Ala Pro Ser Gly His His Gln Ala Gly Arg Cys Leu Leu Trp<br>85 90 95 | 288 |
| gcc tgc aag gcg tgc aag cgc aag acc acc aac gcc gac cgc cgc aag<br>Ala Cys Lys Ala Cys Lys Arg Lys Thr Thr Asn Ala Asp Arg Arg Lys<br>100 105 110 | 336 |
| gcc gcc acc atg cgc gag cgg cgc cgc ctg agc aaa gta aat gag gcc<br>Ala Ala Thr Met Arg Glu Arg Arg Arg Leu Ser Lys Val Asn Glu Ala<br>115 120 125 | 384 |
| ttt gag aca ctc aag cgc tgc acg tcg agc aat cca aac cag cgg ttg<br>Phe Glu Thr Leu Lys Arg Cys Thr Ser Ser Asn Pro Asn Gln Arg Leu<br>130 135 140 | 432 |
| ccc aag gtg gag atc ctg cgc aac gcc atc cgc tat atc gag ggc ctg<br>Pro Lys Val Glu Ile Leu Arg Asn Ala Ile Arg Tyr Ile Glu Gly Leu<br>145 150 155 160 | 480 |
| cag gct ctg ctg cgc gac cag gac gcc gcg ccc cct ggc gcc gca gcc<br>Gln Ala Leu Leu Arg Asp Gln Asp Ala Ala Pro Pro Gly Ala Ala Ala<br>165 170 175 | 528 |
| gcc ttc tat gcg ccg ggc ccg ctg ccc ccg ggc cgc ggc ggc gag cac<br>Ala Phe Tyr Ala Pro Gly Pro Leu Pro Pro Gly Arg Gly Gly Glu His<br>180 185 190 | 576 |
| tac agc ggc gac tcc gac gcg tcc agc ccg cgc tcc aac tgc tcc gac<br>Tyr Ser Gly Asp Ser Asp Ala Ser Ser Pro Arg Ser Asn Cys Ser Asp<br>195 200 205 | 624 |
| ggc atg atg gac tac agc ggc ccc ccg agc ggc gcc cgg cgg cgg aac<br>Gly Met Met Asp Tyr Ser Gly Pro Pro Ser Gly Ala Arg Arg Arg Asn<br>210 215 220 | 672 |
| tgc tac gaa ggc gcc tac tac aac gag gcg ccc agc gaa ccc agg ccc<br>Cys Tyr Glu Gly Ala Tyr Tyr Asn Glu Ala Pro Ser Glu Pro Arg Pro<br>225 230 235 240 | 720 |
| ggg aag agt gcg gcg gtg tcg agc cta gac tgc ctg tcc agc atc gtg<br>Gly Lys Ser Ala Ala Val Ser Ser Leu Asp Cys Leu Ser Ser Ile Val<br>245 250 255 | 768 |
| gag cgc atc tcc acc gag agc cct gcg gcg ccc gcc ctc ctg ctg gcg<br>Glu Arg Ile Ser Thr Glu Ser Pro Ala Ala Pro Ala Leu Leu Leu Ala<br>260 265 270 | 816 |
| gac gtg cct tct gag tcg cct ccg cgc agg caa gag gct gcc gcc ccc<br>Asp Val Pro Ser Glu Ser Pro Pro Arg Arg Gln Glu Ala Ala Ala Pro<br>275 280 285 | 864 |
| agc gag gga gag agc agc ggc gac ccc acc cag tca ccg gac gcc gcc<br>Ser Glu Gly Glu Ser Ser Gly Asp Pro Thr Gln Ser Pro Asp Ala Ala<br>290 295 300 | 912 |
| ccg cag tgc cct gcg ggt gcg aac ccc aac ccg ata tac cag gtg ctc<br>Pro Gln Cys Pro Ala Gly Ala Asn Pro Asn Pro Ile Tyr Gln Val Leu<br>305 310 315 320 | 960 |
| tga | 963 |

<210> SEQ ID NO 128
<211> LENGTH: 320
<212> TYPE: PRT
<213> ORGANISM: Homo sapiens -continued

```
<400> SEQUENCE: 128

Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Met His Val Gly Ala Leu Leu Lys Pro Glu Glu His Ser His
    50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
                100                 105                 110

Ala Ala Thr Met Arg Glu Arg Arg Arg Leu Ser Lys Val Asn Glu Ala
            115                 120                 125

Phe Glu Thr Leu Lys Arg Cys Thr Ser Ser Asn Pro Asn Gln Arg Leu
        130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Ala Phe Tyr Ala Pro Gly Pro Leu Pro Pro Gly Arg Gly Gly Glu His
            180                 185                 190

Tyr Ser Gly Asp Ser Asp Ala Ser Ser Pro Arg Ser Asn Cys Ser Asp
        195                 200                 205

Gly Met Met Asp Tyr Ser Gly Pro Pro Ser Gly Ala Arg Arg Arg Asn
        210                 215                 220

Cys Tyr Glu Gly Ala Tyr Tyr Asn Glu Ala Pro Ser Glu Pro Arg Pro
225                 230                 235                 240

Gly Lys Ser Ala Ala Val Ser Ser Leu Asp Cys Leu Ser Ser Ile Val
                245                 250                 255

Glu Arg Ile Ser Thr Glu Ser Pro Ala Ala Pro Ala Leu Leu Leu Ala
            260                 265                 270

Asp Val Pro Ser Glu Ser Pro Pro Arg Arg Gln Glu Ala Ala Ala Pro
        275                 280                 285

Ser Glu Gly Glu Ser Ser Gly Asp Pro Thr Gln Ser Pro Asp Ala Ala
        290                 295                 300

Pro Gln Cys Pro Ala Gly Ala Asn Pro Asn Pro Ile Tyr Gln Val Leu
305                 310                 315                 320
```